United States Patent [19]
Heijboer et al.

[11] 4,160,829
[45] Jul. 10, 1979

[54] ANTIBACTERIAL 1,2,4-OXADIAZOLYLACETAMIDO CEPHALOSPORINS

[75] Inventors: Robert Heijboer, Waddinxveen; Antoon van Harrewijn, Delft; Peter W. Henniger, Leiden, all of Netherlands

[73] Assignee: Gist-Brocades N.V., Delft, Netherlands

[21] Appl. No.: 795,024

[22] Filed: May 9, 1977

Related U.S. Application Data

[63] Continuation of Ser. No. 571,203, Apr. 24, 1975, abandoned, which is a continuation-in-part of Ser. No. 425,798, Dec. 18, 1973, abandoned.

[30] Foreign Application Priority Data

Dec. 22, 1972 [GB] United Kingdom ............... 59524/72

[51] Int. Cl.$^2$ ................. A61K 31/545; C07D 501/56; C07D 499/46; C07D 271/06
[52] U.S. Cl. ................................ 424/246; 260/239.1; 260/307 G; 424/271; 544/27; 544/28; 544/22
[58] Field of Search .................... 544/27, 28; 424/246

[56] References Cited

U.S. PATENT DOCUMENTS

| 3,516,997 | 6/1970 | Takano et al. ..................... 544/27 |
| 3,646,024 | 2/1972 | Holdredge ..................... 544/28 X |
| 3,821,207 | 6/1974 | Chow et al. ..................... 544/27 |
| 3,929,782 | 12/1975 | Breuer ..................... 544/27 |
| 3,960,849 | 6/1976 | Breuer ..................... 544/27 X |
| 3,991,067 | 11/1976 | Gregory et al. ............. 260/293.67 |

FOREIGN PATENT DOCUMENTS 1946638 9/1970 Fed. Rep. of Germany.

OTHER PUBLICATIONS

Merckx, Chemical Abstracts, vol. 44, 4577f (1948).

Primary Examiner—Donald G. Daus
Assistant Examiner—Diana G. Rivers
Attorney, Agent, or Firm—Hammond & Littell

[57] ABSTRACT 1,2,4-Oxadiazolylacetic acid derivatives. The derivatives include penicillin and cephalosporin amides which have antibiotic properties.

6 Claims, No Drawings

ANTIBACTERIAL 1,2,4-OXADIAZOLYLACETAMIDO CEPHALOSPORINS

PRIOR APPLICATION

The present application is a continuation of copending application Ser. No. 571,203 filed Apr. 24, 1975, now abandoned, which in turn is a continuation-in-part of our copending, commonly assigned U.S. patent application Ser. No. 425,798, filed Dec. 18, 1973 now abandoned.

OBJECTS OF THE INVENTION

It is an object of the invention to provide the novel acid products of formulae I, II and III.

It is another object of the invention to provide novel derivatives of the acid products of formulae I, II or III.

It is a further object of the invention to provide processes for the preparation of compounds of formulae I, II and III and their derivatives.

It is also an object of the invention to provide novel therapeutic compositions and to provide a novel method of combatting bacteria.

These and other objects and advantages of the invention will become obvious from the following detailed description.

THE INVENTION

The novel 1,2,4-oxadiazolylacetic acid compounds of the invention have a formula selected from the group consisting of

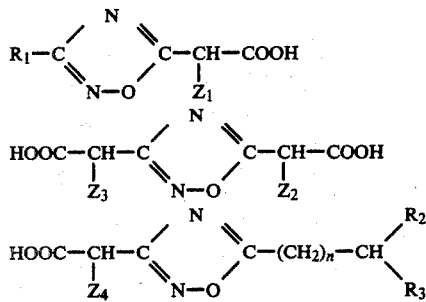

wherein $R_1$ is selected from the group consisting of lower alkyl optionally substituted in a primary or secondary position in relation to the carbon atom in the ring with fluorine, chlorine, hydroxy or lower alkoxy, cycloalkyl optionally substituted with lower alkyl, hydroxy or lower alkoxy, adamantyl, phenyl optionally substituted with at most 3-members of the group consisting of fluorine, chlorine, lower alkyl, hydroxy or lower alkoxy, mononuclear heterocyclic 5-membered group optionally substituted with one or more lower alkyl, or phenyl lower alkyl optionally substituted on the phenyl with hydroxy, lower alkyl, lower alkoxy, chlorine or fluorine, $Z_1$ is selected from the group consisting of hydrogen, lower alkyl, aralkyl, cycloalkyl and phenyl optionally substituted with hydroxy, chlorine, fluorine, lower alkyl or lower alkoxy, and lower alkyl substituted with a mononuclear heterocyclic 5-membered group, $Z_2$ is selected from the group consisting of hydrogen, lower alkyl, phenyl, cycloalkyl, aryl lower alkyl, carboxy esterified with lower alkyl, phenyl, cycloalkyl or aralkyl and N-mono or disubstituted carbamoyl, $Z_3$ is selected from the group consisting of hydrogen, phenyl optionally substituted with at most three members selected from hydroxy, chlorine, fluorine, lower alkyl or lower alkoxy, N-disubstituted carbamoyl and carboxy esterified with lower alkyl, phenyl, cycloalkyl or aralkyl, n is 0,1,2 or 3, $R_2$ is selected from the group consisting of hydrogen and lower alkyl, $R_3$ is selected from the group consisting of hydrogen, lower alkyl, cycloalkyl, phenyl, aralkyl, COOE and carbamoyl optionally substituted with 1 or 2 lower alkyl or lower alkenyl, 1 phenyl, 1 cycloalkyl, 1 or 2 aryl lower alkyl and 1 or 2 cycloalkyl lower alkyl with the phenyl or cycloalkyl being optionally substituted with at most one chlorine, fluorine, hydroxy, lower alkyl or lower alkoxy, E is selected from the group consisting of hydrogen or a salt forming group (when n is $\geq 1$), lower alkyl, benzyl and phenyl and $R_2$ and $R_3$ taken together with the carbon atom to which they are attached are cycloalkyl optionally substituted with fluorine, chlorine, hydroxy, lower alkyl or lower alkoxy and $Z_4$ is selected from the group consisting of hydrogen and aryl optionally substituted with chlorine, fluorine, hydroxy, lower alkyl and lower alkoxy.

The term lower alkyl or lower alkoxy means at most 6 carbon atoms such as methyl, ethyl, propyl, isopropyl, butyl, sec. butyl and tert.-butyl and the term cycloalkyl means a carbocyclic ring of 5 to 8 carbon atoms such as cyclopentyl, cyclohexyl, etc. The mononuclear heterocyclic 5-membered group may be furyl, thienyl, isoxazolyl, isothiazolyl or oxadiazolyl.

The compounds of formulae I, II and III may be prepared by the use of several methods known per se starting from the basic substituted oxadiazole nuclei and the basic substituted 1,2,4-oxadiazole derivatives may be prepared by the application of any of a large number of preparation methods. Illustrative processs are described in, for example, F. Eloy, Fortschr, Chem. Forsch., Vol. 4, p. 807–876 (1965); P. Rajagopalan, Tetrahedron Letters No. 5, p. 311–312 (1969); and F. Eloy et al, Bull Soc. Chim. Belg. 72, p. 719–724 (1963). The substituted 1,2,4-oxadiazolylacetic acids are preferably prepared according to the following routes.

Type I

The group of the 3-substituted-1,2,4-oxadiazol-5-ylacetic acids wherein, for example, $R_1$ is a 2,6-dichlorophenyl, 2,4,6-trimethylphenyl or 2-chloro-6-fluorophenyl, tert.-alkyl such as tert.-butyl, or adamantyl and wherein $Z_1$ is hydrogen, or lower alkyl, cycloalkyl, aralkyl (e.g. benzyl) or aryl group may be prepared by the cyclo addition of stable and reactive nitrile oxides with imidates of various nitriles to 1,2,4-oxadiazoles according to the reaction scheme:

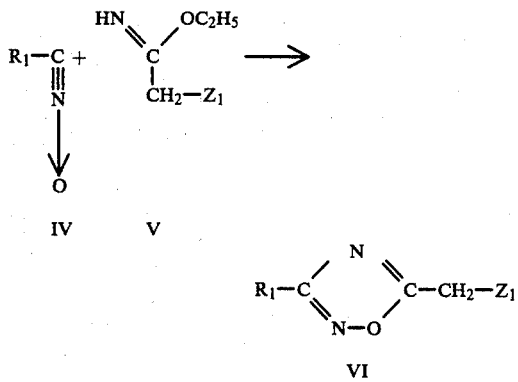

Such a process is described by e.g. P. Rajagopalan in Tetrahedron Letters No. 5, p. 312–312 wherein $R_1$ and $Z_1$ have the significances just mentioned followed by metallation of the methylene (i.e. —$CH_2$—) group of the compound of formula VI, and replacement of the metal atom or component by a carboxyl group, e.g. by the action of carbon dioxide (hereinafter for the sake of brevity such a replacement is called "carbonatation"). The reaction between the imidates and the nitrile oxides is preferably carried out under anhydrous conditions by mixing the two reagents together with cooling, stirring the reaction mixture for about one hour at room temperature, followed by removing excess imidate by evaporation in vacuo. A few crystallizations of the product yield the desired pure 1,2,4-oxadiazole compound.

The starting imidates may be prepared by methods known per se, for example, as described in Organic Synthesis, Coll. Vol. 1, p. 5–6 and Glickmann et al., J.A.C.S. (1945) Vol. 67, p. 1020.

The group of 3-substituted-1,2,4-oxadiazol-5-yl-acetic acids wherein for example, $R_1$ is lower alkyl, cycloalkyl and phenyl substituted with chlorine, fluorine, hydroxy, lower alkyl or lower alkoxy, or a heterocyclic group, such as 2- or 3-thienyl, 4- or 5-isoxazolyl or 4-isothiazolyl, and $Z_1$ is as hereinbefore defined, may be prepared by conversion of nitriles of the formula $$R_1\text{—CN} \qquad\qquad \text{VII}$$

wherein $R_1$ has the meaning indicated above, into the corresponding amidoximes of the formula

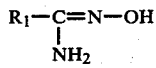

$$\text{VIII}$$

by methods known per se, followed by O-acylation with, for example, said anhydrides, ring closure of the intermediates to compounds of formula VI, followed by metallation and carbonatation.

This preparation route for the compounds of formula VI is known per se from, for example, Eloy, Fortschr. Chem. Forsch. Vol. 4, p. 814. For instance, the compounds are prepared by heating the corresponding O-acylated amidoxime until temperatures between 120° and 170° C., preferably about 150° C., are reached, followed by distillation giving a mixture consisting of water and the desired 1,2,4-oxadiazole compound. The distillate is saturated by addition of potassium carbonate to give a two layer system. The upper layer is removed, dried over calcium chloride, washed with small amounts of ether and redistilled.

The metallation of the methylene group and the subsequent carbonatation may be carried out by methods known per se as described in, for example, Houben-Weyl, Methoden der Organischen Chemie, 4th Edition (1970), Vol. 13/1, p. 93–114, 173–174, 296–350. Introduction of, for example, a lithium atom or sodium atom may be carried out using, for example, butyl lithium-TMEDA, butyl lithium-DABCO, lithium diisopropylamine, lithium isopropyl cyclohexylamine, lithium N,N-dimethylacetamide, lithium bistrimethylsilyacetamide, 2-lithium-1,3-dithiane and 2-lithium-1,3,5-trithiane, sodium hydride, sodamide, sodium methanolate, naphthyl sodium, phenyl sodium, in inert solvents such as pentane, hexane, toluene, diethyl ether, tetrahydrofuran or 1,2-dimethoxyethane and at very low temperatures, e.g. −60° C. and lower.

Replacement of the metal atom or of the metal component by a carboxyl group may be carried out, for example, by adding a solution of the organo metal compound to fresh, solid carbon dioxide on which a layer of dry diethyl ether or tetrahydrofuran is optionally present or by the introduction of gaseous carbon dioxide over or through a solution of the organo metal compound.

The starting amidoxime may be prepared by methods known per se, for example, as described in Lenaers et al Helv. Chim. Acta, Vol. 45 (1962) p. 441–446 (and references indicated therein), and Hurd, Inorganic Synthesis, Vol. 1, p. 89.

Type II

The substituted 1,2,4-oxadiazol-3,5-yl-diacetic acids of formula II may be prepared from the compounds of the formula

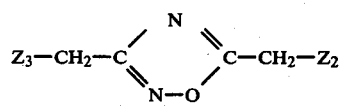

$$\text{IX}$$

wherein $Z_2$ and $Z_3$ are as hereinbefore defined, by double metallation and subsequent double carbonatation.

The compounds of formula IX may be prepared for example by the conversion of nitriles into the corresponding amidoximes, followed by O-acylation with, for example, acid anhydrides and ring closure of the intermediates.

Type III

The 5-substituted-1,2,4-oxadiazol-3-yl-acetic acid compounds wherein $R_2$ is a straight-chain lower alkyl, preferably methyl, optionally substituted by a branched-chain alkyl group, cycloalkyl, phenyl or an unsaturated heterocyclic group (e.g. according to the formula —$CH_2$—$R_4$), and $Z_4$ is hydrogen may be prepared by double metallation of compounds of, for example, the formula

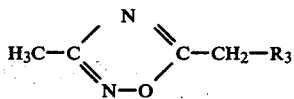

$$\text{X}$$

wherein $R_3$ is as hereinbefore defined, followed by double carbonatation and mono-decarboxylation of the substituent on the 5-position of the oxadiazole nucleus. The compounds of formula X may be prepared according to, for example, the two preferred reaction routes for the oxadiazole ring formation as depicted under Type I.

In several cases, 5-substituents may be introduced by e.g. selective reaction of the 5-acetic acid group of the corresponding bis acetic acids with isocyanates resulting in $R_2$ substituents of the type

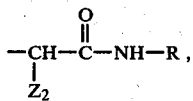

wherein R is the residue which originates from the isocyanate.

The compounds of formulae I, II and III as well as the intermediate organo metal precursors therefore, may be used as starting materials for the preparation of other novel products and form another feature of the invention.

As starting materials, there may be used the acids of formulae I, II and III as such, or active derivatives of these acids, such as various types of anhydrides, including mixed anhydrides, acid chlorides and activated esters.

As final derivatives, there may be prepared:

(A) Esters of the formulae

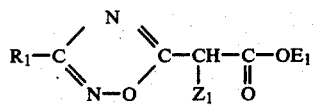
XII wherein $R_1$ and $Z_1$ have the same significances as above in formula I, and $E_1$ is lower alkyl, cycloalkyl, benzyl, benzhydryl or phenacyl; or

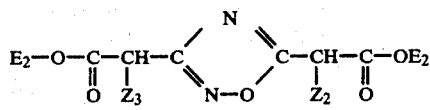
XIII wherein $Z_2$ and $Z_3$ are as hereinbefore defined and $E_2$ is lower alkyl, cycloalkyl, aralkyl, phenyl, phenacyl or benzhydryl, the phenyl residues being optionally substituted with halogen, optionally esterified carboxy, lower alkoxy, lower alkylthio, or $E_r$ is lower alkyl, lower alkoxy and lower alkoxy lower alkyl carbonyl; or

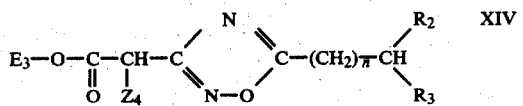
XIV wherein n, $R_2$, $R_3$ and $R_4$ have the same significances as above in formula III, and $E_3$ is lower alkyl, cycloalkyl, aralkyl, phenyl, phenacyl or benzhydryl, the phenyl residues being optionally substituted with halogen, optionally esterified carboxy, lower alkoxy, lower akylthio, or $E_3$ is lower alkyl lower alkoxy, lower alkoxy lower alkyl carbonyl.

The conversion of compounds of formulae I, II and III into the corresponding esters can be carried out by methods known per se and in the case of the less stable acids I and II the reaction conditions are adapted to the sensitivity of the rather reactive acetic acid group involved. The esters of formulae XII and XIV may be also prepared by reacting the intermediate organometal precursors (as used for the preparation of the acids) and preferably the lithium containing precursors, with chloroformic acid esters having the corresponding ester residue.

(B) Amides

Primary, secondary and tertiary amides may be prepared from reactive intermediates such as acid chlorides and anhydrides derived from the acids of formulae I, II and III by application of known methods or by reaction of these acids with phosphazo intermediates prepared in situ from amines and phosphorous trichloride. A great variety of secondary amides can also be prepared by two methods of fairly wide applicability and which both involve a wide variety of isocyanates as the reactive agents.

In the first of these two methods, the α-metallated 1,2,4-oxadiazoles, such as are used in the preparation of oxadiazolylacetic acids of formulae I and II, of the formulae

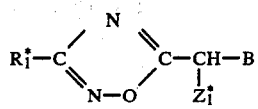
XV or

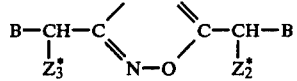
XVI wherein $R_1^*$, $Z_1^*$, $Z_2^*$ and $Z_3^*$ are as hereinbefore defined for $R_1$, $Z_1$, $Z_2$ and $Z_3$ respectively or represent groups which may be easily converted into those groups within the definition of $R_1$, $Z_1$, $Z_2$ and $Z_3$ respectively and which may be influenced or may react under the reaction conditions and wherein B represents a metal atom $Me^I$ or a group $Me^{II}$-Hal, the roman figure indicating the metal valence and Hal representing a halogen, preferably chlorine or bromine, are reacted with isocyanates under suitable conditions. Suitable sunbstituting metal atoms or metal containing groups are lithium, sodium and magnesium chloride or magnesium bromide, lithium being preferred.

According to a preferred method, a lithium atom is introduced by H-Li exchange employing reagents such as n-butyl lithium. In general, moderate to very good yields are obtained when starting from metallated (e.g. lithium or sodium-containing) species wherein at least two substituents such as phenyl, unsaturated heterocyclic radicals or other groups such as carboalkoxy are present, which are capable of stabilizing the generated carbanion at low temperatures and which are bound directly to the metallated carbon atom.

According to the second preparation route for secondary amides, the 1,2,4-oxadiazolylacetic acids are reacted with various isocyanates in suitably selected solvents (e.g. 3,5-dimethyl-1,2,4-oxadiazole) and preferably in the presence of particular catalysts. This preparation method extends the possibilities of the first method insofar that, in this case, species of formulae I, II and III also produce moderate to very good yields of amide, so that compounds of the formula XVII C

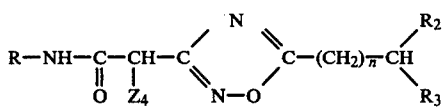

wherein R is the residue which originates from the isocyanate, also can be obtained in addition to the amide derivatives of the formulae

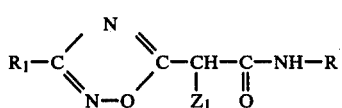
XVIIA

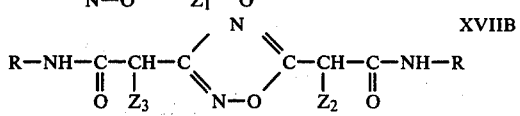
XVIIB

In compounds of formula II, the acetic acid group in the 5-position of the oxadiazole nucleus appears to be much more reactive than the acetic acid group in the 3-position thus often furnishing the possibility for an almost selective reaction of the acetic acid group in position 5 when $Z_2$ and $Z_3$ are suitably selected with an isocyanate in an appropriate solvent under anhydrous conditions, under an inert gas atmosphere and in the presence of small amounts of a suitable not strongly basic catalyst.

The conditions for the use of various types of suitable catalysts are already known from South African patent specification No. 71/7432.

(C)

A great variety of salts may be prepared from the 1,2,4-oxadiazolylacetic acids according to the invention by methods known per se. It will be appreciated that in the esters and amides, as prepared from the starting acids and organo-metal compounds of formulae I, II, III, XV and XVI according to the depicted and aforesaid routes, the substituents present in these compounds can be transformed into other groups (e.g. by removal of the protecting groups) or that other substituents which do not interfere with the structure of these prepared compounds can be introduced later on by methods known per se.

A special feature of the invention is formed by new penicillanic and cephalosporanic acid derivatives, by processes for the preparation and by pharmaceutical compositions containing them. These new penicillanic acid and cephalosporanic acid derivatives of the invention are compounds of the formulae (a) 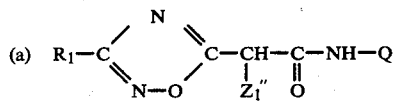 XVIII in which Q is selected from the group consisting of

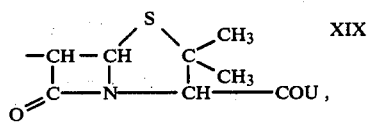 XIX

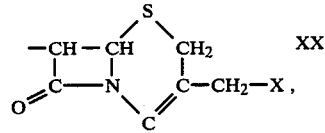 XX

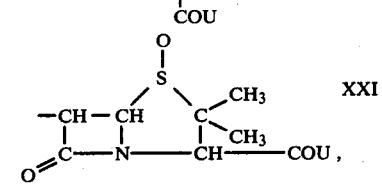 XXI

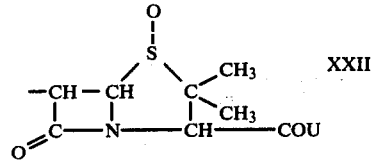 XXII and

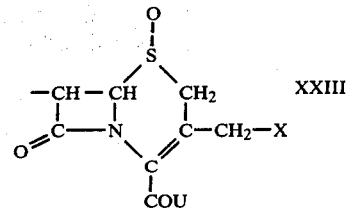 XXIII wherein U is an amido group such as saccharyl, succinimido or phthalimido or a group OE′ in which E′ is hydrogen, a salt forming cation such as alkali metal, alkaline earth metal and amine cation, an ester residue such as lower alkyl optionally substituted with lower alkanoyloxy which can also be substituted, a silyl, a phenacyl, a benzyl, a benzhydryl, trichloroethyl or tert.-butyl group; X is hydrogen, hydroxy, lower alkanoyloxy (preferably acetoxy) or the residue of a nucleophilic agent such as a halogen, an azido, cyano, a carbamoyloxy, an optionally substituted mononuclear heterocyclic group containing a sulfur or nitrogen atom (e.g. pyridinyl); a group —S—Q′ wherein Q′ represents an optionally lower alkyl substituted diazolyl, triezolyl, tetrazolyl, thiazolyl, thiadiazolyl, thiatriazolyl, oxazolyl, oxadiazolyl, benzimidazolyl, imidazolyl, benzoxazolyl, triazolo-pyridinyl or purinyl group or X represents an amino group when Q represents a group of the formula XX; $R_1$ is as hereinbefore defined with respect to formula I but also may be carboxymethyl and $Z_1''$ represents, combined with the above indicated definition for $R_1$, hydrogen, lower alkyl optionally substituted with chlorine or fluorine, lower alkoxy, cycloalkyl, phenyl which is itself optionally substituted with at most three of the substituents as hereinbefore mentioned, or $Z_1''$ is a carboxy group esterified with lower alkyl, phenyl, cycloalkyl or aralkyl, the said phenyl radicals optionally being substituted with at most one of the substituents as hereinbefore mentioned, or $Z_1''$ is carbamoyl optionally N-substituted with one or two lower alkyl groups, one phenyl, one mononuclear five-membered heterocyclic group, one cycloalkyl group, one or two aryl lower alkyl or cycloalkyl lower-alkyl groups, the phenyl and cycloalkyl groups optionally being substituted with at most one of the substituents as mentioned hereinbefore, or $Z_1''$ is carbamoyl having its nitrogen atom as a member of a heterocyclic ring (e.g. morpholino), and wherein $Z_1''$ is hydrogen in combination with $R_1$ representing an acetic acid residue. The term "lower" as applied herein to alkanoyloxy groups means that the group contains at most six carbon atoms.

(b) 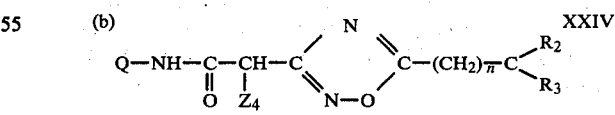 XXIV wherein Q is as hereinbefore defined, and $R_2$, $R_3$, n and $Z_4$ are hereinbefore defined with respect to formula III.

A preferred group of compounds of the invention is that of formula XVIII wherein X is acetoxy, azido, 1-methyltetrazol-5-yl-mercapto or 5-methyl-1,3,4-thiadiazol-2-yl mercapto, wherein $R_1$ is lower alkyl, adamantyl, halomethyl, hydroxymethyl, carboxymethyl, lower alkoxymethyl, benzyl or phenyl optionally carrying one, two or three substituents selected from chlorine and lower alkyl or a single nitro, and more particularly R₁ is methyl, ethyl, methoxymethyl, 2,6-dichlorophenyl, 2,4,6-trimethylphenyl or carboxymethyl, $Z_1''$ is hydrogen, lower alkyl, an optionally substituted phenyl group having substituents as hereinbefore mentioned, an esterified carboxy group, or a carbamoyl group, and alkali metal, alkaline earth metal and non toxic, pharmaceutically acceptable amine salts thereof.

Another preferred group of compounds is that of formula XXIV wherein X is as defined in the preceding preferred group and wherein the group

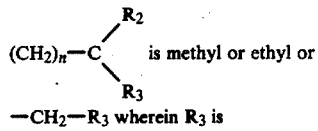 is methyl or ethyl or

—CH₂—R₃ wherein R₃ is wherein R₃ is branched alkyl, cycloalkyl, phenyl, lower alkoxy carbonyl, a N-monosubstituted carbamoyl or an unsaturated heterocyclic, and wherein Z₄ has the same significance as hereinbefore defined, and alkali metal, alkaline earth metal and non-toxic, pharmaceutically acceptable amine salts thereof.

Among the preferred representatives of the compounds of formulae XVIII and XXIV are 7-[α-methyl(3-methyl-1,2,4-oxadiazol-5-yl) acetamido]-3-acetoxymethyl-3-cephem-4-carboxylic acid,
7-[α-methyl)3-ethyl-1,2,4-oxadiazol-5-yl) acetamido]-3-acetoxymethyl-3-cephem-4-carboxylic acid,
7[(3-ethyl-1,2,4-oxadiazol-5-yl) acetamido]-3-acetoxymethyl-3-cephem-4-carboxylic acid,
7-[α-methyl(3-methyl-1,2,4-oxadiazol-5-yl) acetamido]-3-[1-methyl-tetrazol-5-yl-mercaptomethyl]-3-cephem-4-carboxylic acid,
7-[α-methyl(3-methyl-1,2,4-oxadiazol-5-yl)acetamido]-3-[5-methyl-1,3,4-thiadiazol-2-yl-mercaptomethyl]-3-cephem-4-carboxylic acid,
7-[5-methyl-1,2,4-oxadiazol-3-yl-acetamido]-3-[5-methyl-1,3,4-thiadiazol-2-yl-mercaptomethyl]-3-cephem-4-carboxylic acid,
7-[(3-hydroxymethyl-1,2,4-oxadiazol-5-yl-acetamido]-3[1-methyl-tetrazol-5-yl-mercaptomethyl]-3-cephem-4-carboxylic acid,
7[(3-hydroxymethyl-1,2,4-oxadiazol-5-yl-acetamido]-3-[5-methyl-1,3,4-thiadiazol-2-yl-mercaptomethyl]-3-cephem-4-carboxylic acid,
7[(3-methoxymethyl-1,2,4-oxadiazol-5-yl)acetamido]-3-[5-methyl-1,3,4-thiadiazol-2-yl-mercaptomethyl]-3-cephem-4-carboxylic acid,
7-[(3-ethyl-1,2,4-oxadiazol-5-yl)acetamido]-3-[1-methyl-tetrazol-5 -yl-mercaptomethyl]-3-cephem-4-carboxylic acid,
7-[α-methyl (3-ethyl-1,2,4-oxadiazol-5-yl) acetamido]-3-[1-methyl-tetrazol-5-yl-mercaptomethyl]-3-cephem-4-carboxylic acid,
7-[α-methyl(3-ethyl-1,2,4-oxadiazol-5-yl)acetamido]-3-[5-methyl-1,3,4-thiadiazol-2-yl-mercaptomethyl]-3-cephem-4-carboxylic acid,
7-[(5-ethyl-1,2,4-oxadiazol-3yl)acetamido]-3-acetoxymethyl-3-cephem-4-carboxylic acid,
7-[(5-ethyl-1,2,4-oxadiazol-3-yl)acetamido]-3-[1-methyl-tetrazol-5-yl-mercaptomethyl]3-cephem-4-carboxylic acid,
7-[(-3-carboxymethyl-1,2,4-oxadiazol-5-yl)-acetamido]-3-acetoxymethyl-3-cephem-4-carboxylic acid,
7-[(3-methoxymethyl-1,2,4-oxadiazol-5-yl)-acetamido]-3-acetoxymethyl-3-cephem-4-carboxylic acid,
7-[(3-methoxymethyl-1,2,4-oxadiazol-5-yl) acetamido]-3-[1-methyl-tetrazol-5-yl-mercaptomethyl]-3-cephem-4-carboxylic acid,
6-[(3-methyl-1,2,4-oxadiazol-5-yl)acetamido]penicillanic acid,
6-[(3-ethyl-1,2,4-oxadiazol-5-yl)-acetamido]-penicillanic acid,
6-[α-methyl-(3-methyl-1,2,4-oxadiazol-5-yl)-acetamido]-penicillanic acid,
6-[α-methyl-(3-ethyl-1,2,4-oxadiazol-5-yl)-acetamido]-penicillanic acid,
6-{[3-(2,6-dichlorophenyl)-1,2,4-oxadiazol-5-yl]acetamido}-penicillanic acid,
6[(5-methyl-1,2,4-oxadiazol-3-yl)-acetamido]-penicillanic acid,
6[(3-methoxymethyl-1,2,4-oxadiazol-5-yl)-acetamido]-penicillanic acid,
7[(5-benzyl-1,2,4-oxadiazol-3-yl-)acetamido]cephalosporanic acid,
7-[3-methyl-1,2,4-oxadiazol-5-yl-acetamido]-cephalosporanic acid, 7-[3-carboxymethyl-1,2,4-oxadiazol-5-yl-acetamido]-cephalosporanic acid, 7-[3-hydroxymethyl-1,2,4-oxadiazol-5-yl-acetamido]-cephalosporanic acid, 7-[3-methyl-1,2,4-oxadiazol-5-yl-acetamido]-3-azidomethyl-3-cephem-4-carboxylic acid, 7-[3-methyl-1,2,4-oxadiazol-5-yl-acetamido]-3-[1-methyl-tetrazol-5-yl-mercapto-methyl]-3-cephem-4-carboxylic acid, 7-[3-carboxymethyl-1,2,4,-oxadiazol-5-yl-acetamido]-3-[1-methyl-tetrazol-5-yl-mercaptomethyl]-3-cephem-4-carboxylic acid, 7-[3-methyl-1,2,4-oxadiazol-5-yl-acetamido]-3-[5-methyl-1,3,4-thiadiazol-2-yl-mercaptomethyl]-3-cephem-4-carboxylic acid, 7-[5-methyl-1,2,4-oxadiazol-3-yl-acetamido]-3-acetoxymethyl-3-cephem-4-carboxylic acid and 7-[5-methyl-1,2,4-oxadiazol-3-yl-acetamido]-3-[1-methyl-tetrazol-5-yl-mercaptomethyl]-3-cephem-4-carboxylic acid and their non-toxic, pharmaceutically acceptable salts and esters.

The therapeutically useful compounds of the invention can be prepared by several different methods, each of which is an application of a method known per se in the art for the preparation of penicillins and cephalosporins. According to a feature of the invention, the compounds of formulae XVIII and XXIV are prepared by reacting a salt, ester or amide of a 6-aminopenicillanic or 7-aminocephalosporanic acid compound of the formula

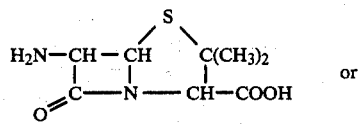 XXV or

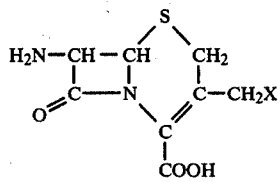 XXVI

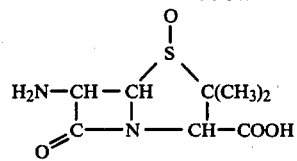 XXVII

-continued

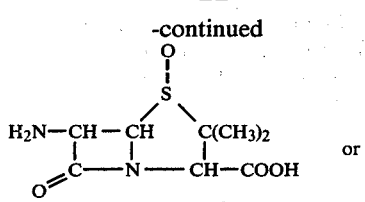
XXVIII or

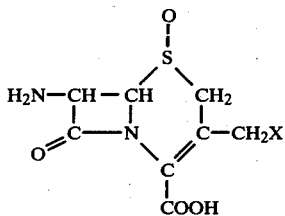
XXIX wherein X is as hereinbefore defined and with the substituent X when a hydroxy or an amino group preferably protected, with an active ester such as 2,4-dinitrophenyl ester, p-nitrophenyl ester or N-hydroxysuccinimido ester of an acid of the formula

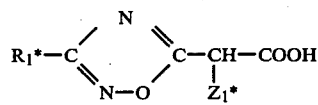
XXX wherein $R_1^*$ and $Z_1^*$ are as hereinbefore defined for $R_1$ and $Z_1''$ or are groups which may be easily converted into those within the definition of $R_1$ and $Z_1''$ and which may be influenced or may react also under the reaction conditions employed (e.g. protected amino, hydroxy and carboxy groups); or

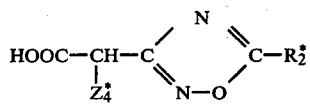
XXXI wherein $R_2^*$ and $Z_4^*$ are as hereinbefore defined for $R_2$ and $Z_4$ or are groups which may be easily converted into those within the definition of $R_2$ and $Z_4$ and which may be influenced or may react also under the reaction conditions, optionally followed by further substitution of the compounds so obtained or conversion of the present substituents into different ones by methods known per se.

Instead of the active esters derived from the acids of formulae XXX and XXXI, other functional derivatives of these acids suitable as acylating agents for a primary amino group may be used. Such derivatives include, for example, the corresponding carboxylic chlorides, bromides, acid anhydrides including mixed anhydrides prepared from stronger acids such as lower aliphatic monoesters of carbonic acid, of alkyl and aryl sulfonic acids and of more sterically hindered acids such as diphenylacetic acid. Moreover, an acid azide or active thioester (e.g. with thiophenol or thioacetic acid) of the acids may be used. Alternatively, the free acids of formulae XXX and XXXI may be coupled with the 6-aminopenicillanic or 7-aminocephalosporanic acid compound by the use of a carbodiimide reagent. Instead of the active esters, such as 2,4-dinitrophenyl and p-nitrophenyl esters, a corresponding azolide, i.e. an amide of the corresponding acid whose amide nitrogen is a member of a quasi-aromatic five-membered ring containing at least two nitrogen atoms such as imidazole, pyrazole, the thiazoles, benzimidazole, benzotriazole and their substituted derivatives, can be employed. The methods for carrying out these reactions to produce a penicillin or a cephalosporin and the methods used to isolate the compounds so produced are well known to the art for similar compounds (c.f. British Pat. Nos. 932,644, 957,570, 959,054, 952,519, 932,530, 967,108 and 967,890).

The ester, salt or amide of the product obtained by the aforesaid process may be converted by methods known per se into the corresponding penicillanic or cephalosporanic acid derivatives. For example, when a silyl (e.g. trialkylsilyl) ester of the starting materials of formulae XXV to XXIX is employed as reactant, the esterifying group can be readily hydrolyzed to yield the corresponding acid compound of formulae XVIII and XXIV.

Another method of the invention for preparing the compounds of formulae XVIII and XXIV comprises reacting an acid of formulae XXX and XXXI and of the formula

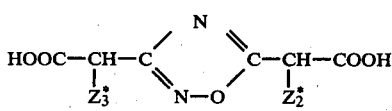
XXXII wherein $Z_2^*$ and $Z_3^*$ are as hereinbefore defined for $Z_2$ and $Z_3$ or are groups which may be easily converted into those groups within the definition of $Z_2$ and $Z_3$ and which may be influenced or may react under the reaction conditions, with a 6-isocyanatopenicillanic acid or 7-isocyanatocephalosporanic acid compound of the formula $O=C=N-Y$, wherein Y is the radical of the formulae XIX or XX having atoms or groups protecting the carboxy group and optional hydroxy or amino group when present, i.e. when X is formula XX is hydroxy or amino. Preferably, the group protecting the carboxy radical or hydroxy radical when present in the 6-isocyanatopenicillanic or 7-isocyanatocephalosporanic reactant is a di- or trialkylsilyl group which can readily be removed from the resultant product by hydrolysis.

The reaction between a carboxylic acid of formulae XXX, XXXI and XXXII and an isocyanate of formula $O=C=N-Y$ is preferably carried out in an inert organic solvent medium such as toluene, dichloromethane benzonitrile or 3,5-dimethyl-1,2,4-oxadiazole. A small amount of an organic base, for example, a substituted imidazole such as N-vinylimidazole, N-methylbenzimidazole or N-isopropylbenzimidazole, may serve as catalyst. These and other conditions for the use of various types of suitable catalysts are described in South African Patent Specification No. 71/7432. The reaction proceeds according to the reaction scheme depicted below for e.g. penicillanic acid derivatives.

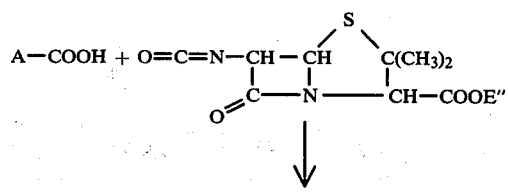

-continued

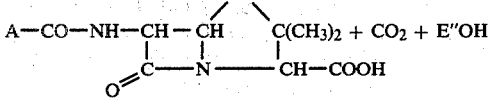

wherein E" is a group protecting the carboxy group during the reaction and is removed after the reaction for example by hydrolysis, hydrogenation or a substitution reaction with basic or nucleophilic agents.

In another method for preparing the penicillanic and cephalosporanic acid derivatives of formulae XVIII and XXIV, a 6-isocyanatopenicillanic or 7-isocyanatocephalosporanic acid compound O=C=N—Y wherein Y is as hereinbefore defined having the carboxy group, and hydroxy or amino group when present, suitably protected is reacted with an organometal compound of the formula A-Me$^I$, A-Me$^{II}$-Hal or A-Me$^{II}$-A, wherein A is a group of the formula

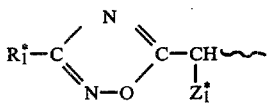 XXXIII wherein $R_1^*$ and $Z_1^*$ are as hereinbefore defined or

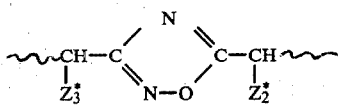 XXXIV wherein $Z_3^*$ and $Z_2^*$ are as hereinbefore defined, Me is a metal atom, e.g. lithium, sodium or magnesium, the numbeal I or II indicating its valency, and Hal is a halogen, preferably chlorine or bromine, atom, followed by hydrolyzing the intermediate product obtained to remove the metal ion, and any hydrolyzable group protecting the carboxy (or hydroxy) group. The reaction is carried out in an anhydrous organic solvent medium under conditions favoring a reaction of the Grignard, Reformatsky or analogous type. A similar reaction method is known from British Patent Specification No. 1,268,536 and South African Patent Specification No. 70/8521.

The isocyanate starting materials of the formula O=C=N—Y wherein Y is as hereinbefore defined can be prepared by reacting phosgene with a penicillanic or cephalosporanic acid derivative as is known from British Patent Specification No. 1,268,536 and South African Patent Specification No. 70/8521.

Another method for the preparation of the compounds of formulae XVIII and XXIV comprises reacting an acid of the formulae XXX, XXXI and XXXII with an in situ prepared phosphazo compound as obtained by the reaction of phosphorous trichloride and an amine salt (preferably a triethylamine salt) of a compound of the formulae XXV, XXVI, XXVII, XXVIII and XXIX. The reaction is preferably carried out at temperatures of about 30° C. and lower in the presence of an exactly predetermined excess of the used amine and under anhydrous conditions.

Preferably, the ratio between the molar amounts of 6-aminopenicillanic acid or 7-aminocephalosporanic acid and its derivatives, triethylamine and phosphorous trichloride is 2:3:1 and dichloromethane is used as reaction medium. This reaction type appeared to be suitably applied in the case wherein very sensitive substituted acetic acid derivatives are used as optionally present reactive substituents appeared not to be attacked or influenced.

According to a further method, the cephalosporanic acid derivatives of formulae XVIII and XXIV wherein Q is the group of formula XX and wherein X initially is hydrogen may be prepared by a ring enlargement reaction from the corresponding penicillanic acid sulfoxide derivatives when Q represents a group of the formulae XXI and XXII, i.e. by heating the penicillanic acid sulfoxide derivative up to 140° C. in the presence of a catalyst and preferably a water-removing agent. These preparative methods are known from Belgian Pat. Nos. 747,118, 747,119, 747,120, and 763,104, and U.S. Pat. Nos. 3,275,626, 3,591,585 and 3,632,850.

The compounds of formulae XVIII and XXIV wherein Q is one of the radicals of the formulae XXI, XXII and XXIII may be also prepared from the corresponding compounds wherein Q is one of the radicals of formulae XIX and XX by suitable oxidation methods. For example, the R-sulfoxides of the corresponding penicillins or cephalosporins may be selectively prepared by using in situ prepared singlet oxygen or by the acylation of the selectively prepared intermediate R-sulfoxides of 6-aminopenicillanic acid and 7-aminocephalosporanic acid and derivatives.

By the term "methods known per se" as used in this specification is meant methods heretofore used or described in the literature.

The new penicillanic and cephalosporanic acid derivatives of formulae XVIII and XXIV wherein Q is the radical of formulae XIX, XX, XXII and XXIII, have antibiotic properties which make them useful as medicines for human beings and animals, alone or mixed with other known antibiotics. Some of these new compounds of formulae XVIII and XXIV have activities comparable with those of known β-lactam containing antibiotics and they have special activities against gram positive microorganisms such as *Bacillus subtilis, Staphylococcus aureus, Streptococcus haemolyticus* and *faecalis* and *Diplococcus pneumoniae*, and have, moreover, a good activity against penicillin resistant Staphylococci. Especially effective are the compounds in which $R_1$ and the group

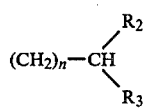

are methyl, ethyl, methoxymethyl, mesithyl, benzyl and 2,6-dichlorophenyl group, Q is a group of formulae XIX and XX and $Z_1$ and $Z_4$ are hydrogen or methyl, and salts of such compounds. They are also active against gram negative microorganisms such as *Brucella melitensis, Pasteurella multocida, Proteus rettgeri* and *Salmonella dublin*.

The aforesaid antibiotic compounds according to the invention are preferably employed for therapeutic purposes in the form of a non-toxic, pharmaceutically acceptable salt such as the sodium, potassium or calcium salt. Other salts that may be used include the non-toxic, pharmaceutically acceptable, suitably crystalline salts with organic bases such as amines, for example trialkylamines, procaine and dibenzylamine.

In the treatment of bacterial infections, the antibiotic compounds of this invention can be administered topically, orally or parenterally in accordance with conventional procedures for administration of antibiotics. They are administered in dosage units containing an effective amount of the active ingredient in combination with suitable physiologically acceptable carriers or excipients. The dosage units can be in the form of liquid preparations such as solutions, suspensions, dispersions or emulsions or in a solid form such as powders, tablets and capsules.

Accordingly, the invention includes within its scope antibacterial compositions comprising an effective amount of a new penicillanic or cephalosporanic acid derivative of formulae XVIII and XXIV, or a non-toxic, pharmaceutically acceptable salt thereof in association with a physiologically acceptable carrier or excipient. Such therapeutic compositions can also include one or more therapeutically active ingredients in addition to a compound of the invention. The term "effective amount" as used herein in relation to the described compounds means an amount which is sufficient to destroy or inhibit the growth of susceptible microorganisms when administered in the usual manner, in other words an amount which is sufficient to control the growth of bacteria. The magnitude of an effective amount can be easily determined by those skilled in the art through standard procedures for determining the relative activity of anti-bacterial agents when utilized against susceptible microorganisms via the various available routes of administration.

Suitable carriers and excipients may be any convenient physiologically acceptable ingredient which serves to facilitate administration of the therapeutically active compound. Carriers may provide some ancillary function such as that of a diluent, flavor masking agent, binding agent, action-delaying agent or stabilizer. Examples of carriers include water which can contain gelatin, acacia, alginate, dextran, polyvinylpyrrolidine or sodium carboxymethyl cellulose, aqueous ethanol, syrup, isotonic saline, isotonic glucose, starch, lactose, or any other such material commonly used in pharmaceutical and veterinary antibacterial compositions.

Another aspect of the invention includes a method for inhibiting the growth of bacteria by applying to the habitat of the bacteria or contacting bacteria with an effective amount of the antibacterial compounds described herein. For example, the method can be applied to the treatment of bacterial infections in animals by administering to the host an effective amount of an antibacterial compound of the invention.

To make the penicillanic acid or cephalosporanic acid derivatives of formulae XVIII and XXIV more suitable for absorption in the body while their antibiotic activity is maintained, the conversion of the compounds of formulae XVIII and XXIV wherein U is —OH into special esters may be necessary. Preferred ester residues are, for instance, those of the type: —CH$_2$—O—C-O—W wherein W is an unsubstituted or substituted straight or branched-chain alkyl radical of 1 to 8 carbon atoms, the substituents being selected from lower alkoxy, lower alkythio, halo lower alkyl, phenyl, cycloalkyl, nitro, amino, guanidino, carboxy, carbalkoxy, hydroxy groups and halogen atoms. The novel penicillanic acid and cephalosporanic acid derivatives of formulae XVIII and XXIV may also be used as growth promotors for ruminant animals such as cattle. They are also very useful in in vitro application such as for desinfecting compositions (e.g. dairy barns) at a concentration of about 0.1 to 1% by weight of such compositions dissolved or suspended in a suitable inert carrier for application by washing or spraying.

Moreover, some of the 3-substituted 1,2,4-oxadiazol-5-yl-acetic acids of formula I and especially 3-benzyl-1,2,4-oxadiazol-5-yl-acetic acid appeared to show an antiphlogistic activity.

The other derivatives according to the invention prepared by means of the preparation routes which are known per se, are those of the formulae

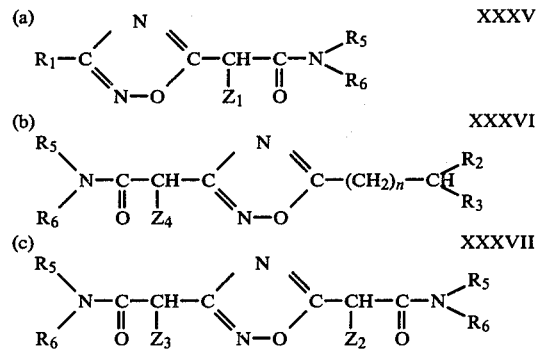

wherein $R_1$, $R_2$, $R_3$, n, $Z_1$, $Z_2$, $Z_3$ and $Z_4$ are as hereinbefore defined, $R_5$ represents a hydrogen atom, a lower alkyl group, an aryl lower alkyl or a cycloalkyl lower alkyl group, and $R_6$ represents a hydrogen atom or a lower alkyl, phenyl, a mononuclear five- or six-membered heterocyclyl, cycloalkyl, an aryl lower alkyl or cycloalkyl lower alkyl group, the phenyl and cycloalkyl groups optionally being substituted with at most one of the substituents as hereinbefore mentioned, or wherein $R_6$ represents an amino group optionally substituted with a lower alkylcarbonyl, arylcarbonyl, mononuclear heterocyclic carbonyl or lower alkoxycarbonyl, or wherein $R_5$ and $R_6$ together with the nitrogen atom to which they are attached represent a five- to seven-membered mononuclear heterocyclic ring, such as morpholino or piperidino.

Members of the classes of the final ester and amide derivatives of formulae XII, XIII, XIV, and XXXV, XXXVI and XXXVII respectively, which have been tested have also showed a central depressive activity and may be used as a.o. anticonvulsants, muscle relaxants and tremor antagonists. Moreover, members of the classes of amide derivatives of formulae XXXV, XXXVI and XXXVII which have been tested have showed activities against some types of fungi such as against Trichophyton and Microsporum strains.

In the following examples there are described several preferred embodiments to illustrate the invention. However, it should be understood that the invention is not intended to be limited to the specific embodiments.

EXAMPLE 1

3-methyl-1,2,4-oxadiazol-5-yl-acetic acid

A solution of 4.0 g (40.8 mmol) of 3,5-dimethyl-1,2,4-oxadiazole and of 6.0 ml of N,N,N',N'-tetramethylethylenediamine (TMEDA) in 100 ml of dry toluene was prepared in a 250 ml three-necked glass vessel equipped with a thermometer, a gas inlet tube through which dry nitrogen was introduced continuously and a pressure equalized dropping funnel. The magnetically stirred solution was cooled to −75° C. with an acetone-carbon dioxide bath and by means of the dropping funnel, a solution of approximately 40 mmol of n-butyllithium in 20 ml of n-hexane was added slowly to keep the reaction mixture below −65° C. Afterwards the reaction mixture was stirred for another 60 minutes at −55° to −60° C. Subsequently, the reaction mixture was transferred with a bent ground glass tube to a second vessel containing powdered carbon dioxide covered with a layer of dry diethyl ether and after standing a few hours, the carbon dioxide had practically disappeared from the mixture. 100 ml of water were added, followed by addition of 1 N hydrochloric acid with stirring until a pH of 8 was attained. The layers were separated and the organic layer was discarded and the aqueous layer was shaken twice with 25 ml of diethyl ether. The pH of the aqueous layer was brought to 2.0 with 1 N hydrochloric acid and seven extractions with about 25 ml portions of ethyl acetate at pH 2.0 resulted in almost complete removal of the desired product from the aqueous layer. The extracts were combined, dried over anhydrous magnesium sulfate, and filtered and the filtrate was concentrated in vacuo to a small volume until a crystalline white precipitate appeared. Thin-layer chromatography showed that the supernatant liquid still contained a considerable amount of the desired product and no by-products and the solvent was then completely removed in vacuo. The practically colorless residue was dried to constant weight to obtain 4.2 g (72% yield) of the product with a purity of at least 96% estimated by TLC and PMR spectrum. Recrystallization of the product was effected by dissolution in a minimum volume of chloroform, followed by slow addition of petroleum ether (b.p. 80°–110° C.) until a turbidity appear to obtain 3.6 g of 3-methyl-1,2,4-oxadiazol-5-yl-acetic acid with a melting point of about 95° C. (slow decarboxylation sets in at about 90° C.).

$pK_a$-value (determined in water): 3.64

Analysis: $C_5H_6N_2O_3$: Calculated: %C 42.26, %H 4.26, %N 19.71, %O 33.77. Found: %C 42.24, %H 4.28, %N 19.60, %O 33.88.

Partial analysis of the IR spectrum (KBr-disc, values in cm$^{-1}$): ±3450, 1740, 1720, 1590, 1360, 1220. Thin-layer chromatograph: Silica plate, eluent is a 10:2:1:0.2 mixture (by volume) of diethyl ether, ethanol, water and formic acid and drying by blowing warm air over the plate. Yellow colored spot (Rf-value=about 0.7) after 5 minutes in cylinder containing iodine crystals. Bluish spot after spray with 1% starch solution in water.

Partial interpretation of the mass spectrum: Since the compound decarboxylates easily, its molecular weight was indicated by a rather weak molecular ion peak (M/e=142). The product of decarboxylation, 3,5-dimethyl-1,2,4-oxadiazole, was represented by M/e=98. M/e=85, 59 and 57 presumably representing the fragments N—$CH_2COOH$, $CH_2COOH$ and $CH_3CNO$ present further proof for the structure.

The PMR spectrum of a solution of 3-methyl-1,2,4-oxadiazol-5-yl-acetic acid in CDCl$_3$ (60 Mc, δ-values in ppm, tetramethylsilane as internal reference) showed signals at: 2.43 (s,3H), 4.06 (S, 2H), 9.2 (s, about 1H).

EXAMPLE 2

3-(2,6-dichlorophenyl)-1,2,4-oxadiazol-5-yl-acetic acid

A solution of an approximately equivalent amount of n-butyl lithium in 22.2 ml of n-hexane was added dropwise to a solution of 10 g of 3-(2,6-dichlorophenyl)-5-methyl-1,2,4-oxadiazole (m.p. 83°–85° C.) and 6.4 ml of TMEDA in 140 ml of dry toluene using the procedure of Example 1 over a period of about 30 minutes. The reaction temperature was −55° to −60° C. After stirring the reaction mixture for another hour at about −60° C. the mixture was added to powdered carbon dioxide covered with dry diethyl ether. After standing a few hours, water and dilute hydrochloric acid were added until a pH of 8.0 was reached. The layers were separated, and the organic layer was extracted with 50 ml of water. The organic layer was discarded and the combined aqueous layers of about 300 ml were washed twice with 100 ml of diethyl ether. Then, the aqueous layer was extracted three times with 100 ml portions of diethyl ether at a pH of 2.0 These extracts were combined, washed twice with a small amount of ice-water and completely evaporated in vacuo. The solid residue was stirred up first with n-heptane and then with a small volume of toluene. After extensive drying in the desiccator, the final product of 3-(2,6-dichlorophenyl)-1,2,4-oxadiazol-5-yl-acetic acid weighed 7.6 g (63% yield) and had a m.p. of 124.5°–125.5° C.

PMR (60 Mc, CDCl$_3$), tetramethylsilane as internal reference, δ-values in ppm) $CH_2$: 4.09 (s, 2H), $C_6H_3$: 7.45 (almost a singlet, 3H).

EXAMPLE 3

3-(2,4,6-trimethylphenyl)-1,2,4-oxadiazol-5-yl-acetic acid

Starting from 3-(2,4,6-trimethylphenyl)-5-methyl-1,2,4-oxadiazole with a m.p. of 20°–30° C., 3-(2,4,6-trimethylphenyl)-1,2,4-oxadiazol-5-yl-acetic acid was prepared by the method of Example 2. A powerful mechanical stirrer was used in the reaction involving n-butyl lithium to obtain a 55.7% yield of 3-(2,4,6-trimethylphenyl)-1,2,4-oxadiazol-5-yl-acetic acid with a m.p. of 106°–108° C. IR (KBr-disc, values in cm$^{-1}$): ±3450, 1740, 1720, 1608, 1590 and shoulder 1580, 1365 and 1240.

PMR (60 Mc, CDCl$_3$, tetramethylsilane as internal reference, δ-values in ppm): 2.13 (s, 6H), 2.30 (s, 3H), 4.07 (s, 2H), 6.92 (s, 2H).

EXAMPLE 4

5-methyl-1,2,4-oxadiazol-3-yl-acetic acid 80 g (0.816 M) of 3,5-dimethyl-1,2,4-oxadiazole and 240 ml of (1.6 M) of TMEDA were dissolved in 2050 ml of dry toluene and after the solution was cooled to −70° C., there was gradual addition of 800 ml of an about 20% solution of n-butyl lithium in n-hexane (about 1.6–1.9 M). The rate of the addition was adjusted so that the reaction temperature varied between −60° and −65° C. and most of the addition time of about 70 minutes was taken up by the addition of the first equivalent of n-butyl lithium. The reaction mixture was then stirred for 60 minutes at −70° C. Subsequently, the reaction mixture was poured slowly into a mixture of finely powdered carbon dioxide and dry diethyl ether. After standing about 3 hours, 1 liter of water was added to the mixture of solid and liquid and the contents of the vessel were transferred to a separating funnel. The aqueous layer was collected and, as the solid was only partly dissolved, 250 ml of water was added to the mixture of salt and organic solvent. The mixture was shaken again and the aqueous layer added to the first extract. This was repeated till all the solid was dissolved in water. The organic layer was discarded and the alkaline aqueous layer was washed three times with diethyl ether. Then, concentrated phosphoric acid was added until a pH of 2.0 was reached, and the solution in water was concentrated in vacuo at 60° C. to a volume of about 2 liters. During these operations, the mixture of 3-methyl-1,2,4-oxadiazol-5-yl-acetic acid and 1,2,4-oxadiazol-3,5-diacetic acid (contaminated with much smaller amounts of two or three unidentified by-products) was already partly decarboxylated to 3,5-dimethyl-oxadiazole and 5-methyl-1,2,4-oxadiazol-3-yl-acetic acid. Decarboxylation was completed by heating the acidic solution for one hour on a steam-bath and the greater part of the desired product was extracted with three 300 ml portions of ethyl acetate. The remainder was obtained by continuous extraction with diethyl ether for 16 hours and the collected organic layers were completely evaporated. The residue was dissolved in about 600 ml of diethyl ether and the solution was treated with activated carbon, filtered and completely evaporated. The 54.6 g of partly solid residue was submitted to column chromatography (length 38 cm, diameter 5.7 cm) over silica with diethyl ether mainly to remove valeric acid. A fraction of 1.6 g of over 90% pure product and a quantity of 37.4 g of over 95% pure product were obtained. The latter amount was recrystallized from toluene/n-heptane to obtain 34.2 g (29% yield) of 5-methyl-1,2,4-oxadiazol-3-yl-acetic acid of at least 97% purity (estimated by TLC and PMR spectrum) with a m.p. of 101°–103° C. (final melting point-)—above 70° C. sublimation, melting and resolidification.

$pK_a$-value (determined in water): about 3.4.

Thin layer chromatography: Same system as used in Example 1 Rf-value=about 0.25. The oxadiazol-3-yl-acetic acid is much less sensitive to the detection system than its isomer.

Analysis of the PMR spectrum of a solution of 5-methyl-1,2,4-oxadiazol-3-yl-acetic acid in $CDCl_3$ and one droplet of $d_6$-DMSO (60 Mc,δ-values in ppm, tetramethylsilane as internal reference): 2.58 (s, 3H), 3.78 (s, 2H), 10 (s, about 1H).

Partial analysis of the IR spectrum (KBr-disc, values in cm$^{-1}$): ±3450, 1740 and 1720, 1595, 1430, 1415, 1395, 1380, 1225.

Analogously, other 1,2,4-oxadiazol-3-yl-acetic acids were obtained. 5.8 g (34% yield) of 5-benzyl-1,2,4-oxadiazol-3-yl-acetic acid with a m.p. of 109°–111.5° C. was obtained starting from 13 g of 3-methyl-5-benzyl-1,2,4-oxadiazole. During the reaction, 2 equivalents of n-butyl lithium dissolved in n-hexane were added slowly to the solution of the oxadiazole and 2 equivalents of TMEDA in toluene at −75° to −80° C. The resulting reaction of mixture was stirred during 6 hours at −78° C. and subsequently poured out onto finely powdered carbon dioxide. The reaction product was poured out in about 600 ml of water whereupon the pH was adjusted to 7.0. The layers were separated and the organic layer was once washed with water. The solution in water was purified by continuous extraction with diethyl ether at pH 8.0 for 5 hours, acidified to pH 5.2 and subsequently concentrated in vacuo at about 45° C. to a volume of about 300 ml. The pH was adjusted to 7.0, followed by vacuum filtration. The pH was adjusted to 1.8, whereupon continuous extraction with dichloromethane was applied for 16 hours. Solvent was removed and the residue was dissolved in a minimal volume of water, followed by extraction with a 1:1 mixture of diethyl ether and ethyl acetate at pH 1.8. The final extract was evaporated in vacuo and the residue was crystallized from diethyl ether. As indicated above, the primary product (α-(5)-phenyl-1,2,4-oxadiazol-3,5-diyl-bisacetic acid) was subject to selective decarboxylation under relatively mild conditions. However, it was experienced that it also can be obtained by means of extractions at room temperature followed by purification by column chromatography, etc. (see Remarks of Example 39).

IR (KBr-disc, values in cm$^{-1}$): ±3400, 1725, 1580, 1495, 1460, 1410, 1380, 1330, 1225, 1190, 960, 940, 840, 820, 780, 730, 710.

PMR ($CDCl_3$ and a trace of $d_6$-DMSO, 60 Mc, TMS,δ-values in ppm): 3.75 (s, 2H), 4.21 (s, 2H), 7.3 (s, 5H), about 8.9 (s, 1H).

28 g (21% yield) of 5-ethyl-1,2,4-oxadiazol-3-yl-acetic acid with a m.p. of 58°–60° C. were obtained starting from 89.6 g of 3-methyl-5-ethyl-1,2,4-oxadiazol, after incomplete, in situ decarboxylation of the primary product, α(5)-methyl-1,2,4-oxadiazol-3,5-diyl-bisacetic acid which was a relatively stable compound. The reaction conditions were analogous to the above conditions, but the addition of the solution of n-butyl lithium was extended to an eight hour period. Subsequently, the vessel was closed and kept over night at −78° C. After the reaction with solid carbon dioxide, the reaction mixture was neutralized as usual. After separation of the layers, the organic layer was discarded, the water-layer acidified to pH 2.0 and heated for 3.5 hours on the steam-bath. The pH was brought to 8.0 whereupon the solution in water was concentrated in vacuo to about half of its volume. Precipitated salts were removed by filtration and the filtrate at a pH 8.0 was subjected to continuous extraction with diethyl ether for 5 hours. Subsequently, the pH was brought to 5.0, followed by continuous extraction with n-pentane for 30 hours. The solution in water was acidified to a pH of 2.5, saturated with sodium chloride and was extracted 5 times with equal volumes of acetone. These extracts were combined and activated carbon was added, whereupon half of the volume was removed by distillation at atmospheric pressure. After filtration, the filtrate was evaporated and the residue was submitted to column chromatography over silica with n-hexane/chloroform. The pure fractions were combined and evaporated in vacuo. The residual oil was dissolved in a small volume of ether, the solution filtered and evaporated to dryness and the colorless oil slowly solidified upon standing.

IR (ibidem): ±3500 and ±2600, 3000, ±2960, 1730, 1580, 1465, 1425, 1380, 1360, 1300, 1210–1230, 1190, 900, 825, 805, 725.

PMR ($CDCl_3$, 60 Mc, TMS, δ-values in ppm): 1.40 (t, J=7.5 cps, 3H); 2.92 (q, J=7.5 cps, 2H); 3.84 (s,2H), about 8.6 (s, 1H).

EXAMPLE 5 methyl 3-methyl-1,2,4-oxadiazol-5-yl-acetate

A solution of an excess of diazomethane in diethyl ether was added to a stirred, cold (about 2° C.) solution of 14 g of 3-methyl-1,2,4-oxadiazol-5-yl-acetic acid in 500 ml of diethyl ether. After the initially vigorous evolution of nitrogen was finished, the solution was concentrated on the steam bath to about 250 ml. The solution was washed three times with 100 ml of water and the wash waters were combined, adjusted to a pH of 9.0 and were extracted with diethyl ether to obtain the part of the product which dissolved in water during the washings. The combined ethereal extracts were filtered through a water repelling paper filter and then were evaporated in vacuo. After keeping the residue for 1 hour at 8 mm the residual oil weighed 14.8 g. The yellow oil was distilled at 0.4–0.5 mm and the collected fraction with a boiling point 70°–71° C. to obtain 12.3 g of methyl 3-methyl-1,2,4-oxadiazol-5-yl-acetate with a refractive index $n_D^{25} = 1.4472$.

PMR (60 Mc, CDCl$_3$, TMS as internal reference, δ-values in ppm): 2.38 (s, 3H), 3.76 (s, 3H), 3.99 (s, 2H).

IR (NaCl windows, values in cm$^{-1}$): 3020, 2985, 2870, 1760 and 1600.

EXAMPLE 6 sodium DL-6-{[α-phenyl-3-methyl-1,2,4-oxadiazol-5-yl-]-acetamido}-penicillanate A solution of about 9 ml of n-butyl lithium in a mixture of 4.5 ml of n-hexane and 4.5 ml of toluene was added dropwise at −95° to −90° C. to a solution of 1.74 g (10 mmol) of 3-methyl-5-benzyl-1,2,4-oxadiazole in 20 ml of dry tetrahydrofuran and the resulting yellow liquid reaction mixture was additionally stirred for 30 minutes at −90° C. Then a solution of 2.6 g (8.3 mmol) of trimethylsilyl 6-isocyanato-penicillanate in 10 ml of tetrahydrofuran was slowly added dropwise with the reaction temperature remaining slightly below −90° C. After 30 minutes stirring at −90° C., 1.2 ml of trimethyl chlorosilane were added by means of a pipette and the resulting, still clear solution was stirred for a few minutes at about −80° C. and then was poured out into 25 ml of ice-water. A dilute sodium hydroxide solution was added until pH 7.0 was reached. The layers were separated, the organic layer was discarded and the aqueous layer was shaken twice with 30 ml of diethyl ether. The aqueous layer was acidified to pH 4.5, followed by three extractions with 20 ml of diethyl ether. Three more extractions were carried out at pH 5 with 20 ml of ethyl acetate each time. The acidic organic layers were combined, washed twice with a small volume of ice-water, dried over anhydrous magnesium sulfate, filtered and concentrated in vacuo to about 5 ml. A slight excess of sodium α-ethylcaproate dissolved in a small volume of acetone was added in the cold. The resulting solution was treated with an excess of diethyl ether which caused precipitation of an almost colorless solid and the solid was collected by filtration and was repeatedly washed with cold, dry diethyl ether to obtain 760 mg of sodium DL-6-[α-phenyl-3-methyl-1,2,4-oxadiazol-5-yl]-acetamido-penicillanate slightly contaminated with sodium α-ethylcaproate, and contained about 2 moles of water. The D/L-ratio was about 1:1.

Analysis of the PMR spectrum of a solution of the final penicillanate product in a d$_6$-dimethylsulfoxide (2 micro drops DCO$_2$D added, 60 Mc, δ-values in ppm, 2,2-dimethylsilapentane-5-sulfonate as internal reference): 1.46, 1.52, 1.56 and 1.62 (about 6H); 2.34 (s, 3H), 4.22 (2 singlets, δν=1.2 cps, 1H), ±5.5 (q-like, 2H), 5.67 (partially deuterated, broadened singlet): ±7.4 (5H), about 9.15.

EXAMPLE 7

7-[(3-benzyl-1,2,4-oxadiazol-5-yl)-acetamido]-desacetoxycephalosporanic acid 1.5 ml (10 mmol) of TMEDA were added to a solution of 1.74 g (10 mmol) of 3-benzyl-5-methyl-1,2,4-oxadiazole in a mixture of 20 ml of dry toluene and 5 ml of dry tetrahydrofuran after which the solution was cooled to −100° C. Next, a solution of about 10 mmol of n-butyl lithium in 5 ml of n-hexane was added dropwise at −100° to −105° C. and this was followed by additional stirring for 1 hour at −100° ±5° C. A solution of 2.81 g (9 mmol) of trimethylsilyl 7-isocyanato-desacetoxycephalosporanate in a mixture of 20 ml of toluene and 5 ml of tetrahydrofuran was added dropwise at temperatures below −95° C. and the resulting reaction mixture was stirred for 90 minutes at −95° C., and then, over about 15 minutes, the temperature was slowly raised to −85° C. Subsequently, the reaction mixture was poured into a well stirred mixture of 25 ml of ice-water and 25 ml of ethyl acetate and dilute hydrochloric acid was added simultaneously in order to maintain the pH close to 4. After a few minutes stirring, the pH was raised to 7.0 and the layers were separated. The organic layer was discarded and the aqueous layer was extracted twice with 80 ml of ethyl acetate at pH 6.5 and pH 6.0 respectively, resulting in the removal of a by-product and a small amount of the desired product. The greater part of the desired product was removed from the aqueous layer by six extractions with 40 ml of ethyl acetate at pH values gradually decreasing from 6.0 to 4.5. These extracts were combined, washed twice with a small volume of ice-water, treated with activated carbon, dried over anhydrous magnesium sulfate, filtered and completely evaporated in vacuo. The residue was triturated with diethyl ether, vacuum filtered, washed with cold ether and dried in vacuo to obtain 1.0 g (25% yield) of 7-[(3-benzyl-1,2,4-oxadiazol-5-yl)-acetamido]-desacetoxycephalosporanic acid in the form of a colorless solid. The purity of the final desacetoxycephalosporanic acid product was estimated to be 90–95% (according to TLC and PMR spectrum).

IR (KBr-disc, values in cm$^{-1}$): ±3500 and ±2600, 3280, 1780, 1720, 1670, 1590, 1550, 1495.

PMR (60 Mc, d$_6$-DMSO, 2,2-dimethyl-silapentane-5-sulfonate, δ-values in ppm): 2.06 (s, 3H), 3.5 (q, $J_{AB} \approx 17.5$ cps, 2H), 4.06 (s) and 4.10 (s) together 4H, ±5.1 (d, J=4.6 cps, 1H), ±5.6 (q, J=4.6 cps, J'≈8.0 cps, 1H), 7.35 (s, 5H), 9.3 (d, J'≈8.0 cps, 0.8H).

EXAMPLE 8

N-phenyl-3-(2,4,6-trimethylphenyl)-1,2,4-oxadiazol-5-yl-acetamide

STEP A: An acid chloride-like reactive intermediate of 3-(2,4,6-trimethylphenyl)-1,2,4-oxadiazol-5-yl-acetic acid A solution of 250 mg (1 mmol) of 3-(2,4,6-trimethylphenyl)-1,2,4-oxadiazol-5-yl-acetic acid, 0.005 ml of dimethylformamide and 0.11 ml of pure thionyl chloride in 5 ml of carbon tetrachloride was refluxed under anhydrous conditions for 1 hour while several samples were taken at different time intervals. Carbon tetrachloride was removed by blowing dry nitrogen over the samples and then, the residues were dissolved in anhydrous chloroform and IR spectra taken to examine the progress of the reaction. It became clear that the reaction mixture should not be refluxed more than 10 minutes (3–5 minutes is sufficient). The prepared reactive intermediate is not the acid chloride as such, but instead a reactive intermediate. This reactive intermediate nevertheless gave the expected amides in modest yields when reacted with amines. The empirically found changes in the IR spectra are as follows. The relevant features of a solution of the starting acid in chloroform are a monomeric OH at 3500, dimeric OH at 3000–3200 approximately, monomeric C=O (shoulder) at ±1760 and dimeric C=O at 1730 cm$^{-1}$. After 3 minutes reflux, both OH bands and the C=O band at 1760 cm$^{-1}$ were completely vanished. There remained one sharp and intensive absorption at 1740 cm$^{-1}$ representing the reactive compound. Reflux times of more than approximately 10 minutes resulted in breakdown of the absorption at 1740 and the appearance of at least four other absorptions between 1660 and 1800 cm$^{-1}$, one of them (at 1790) possibly representing the true acid chloride.

STEP B:
3-(2,4,6-trimethylphenyl)-1,2,4-oxadiazol-5-yl-acetanilide 1 mmol of the starting compound was treated as indicated above with 0.11 ml of thionyl chloride in 5 ml of carbon tetrachloride in the presence of about 0.005 ml of dimethylformamide. The mixture was refluxed for 3 minutes and then 0.3 ml of aniline was added followed by 5 minutes reflux. The mixture was evaporated in vacuo and 35 ml of toluene and 25 ml of water were added to the residue followed by dilute hydrochloric acid until a pH of 1.5 was reached. After separation of the layers, the organic layer was washed with 20 ml of 4 N hydrochloric acid and subsequently with 25 ml of water. The organic layer was evaporated to dryness and the residue was dissolved in ethanol. The solution was treated with activated carbon and the resulting colorless solution in ethanol was again evaporated. The colorless, crystalline residue was washed with n-heptane and dried in vacuo to obtain N-phenyl-3-(2,4,6-trimethylphenyl)-1,2,4-oxadiazol-5-yl-acetamide. The IR and PMR spectra confirmed the structure.

PMR (60 Mc, CDCl$_3$+d$_6$-DMSO, TMS as internal reference, δ-values in ppm): 2.16 (s, 6H), 2.31 (s, 3H), 4.18 (s, 2H), about 5.1 (broad, about 1H), 6.91 (s) and about 6.8 to 7.8 (multiplet) together 7H.

IR (KBr, values in cm$^{-1}$): 3300, 1660, 1600, 1580, 1545, 1355 and 1240.

EXAMPLE 9
7-{[3-(2,4,6-trimethylphenyl)-1,2,4-oxadiazol-5-yl]-acetamido}-cephalosporanic acid.

A mixture of a major amount of N,O-bis-trimethylsilyl-7-ACA and a minor amount of trimethylsilyl 7-amino-cephalosporanate was prepared in the usual manner from 967 mg (3.66 mmol) of 7-amino-cephalosporanic acid (7-ACA) suspended in 20 ml of ethyl acetate by addition consecutively of 1.02 ml (7.32 mmol) of triethylamine and 0.92 ml (7.32 mmol) of trimethylchlorosilane at 5° C., followed by 30 minutes additional stirring at 30° C. 0.43 ml (3.66 mmol) of quinoline was added to the obtained reaction mixture.

In the meantime, 900 mg (3.66 mmol) of 3-(2,4,6-trimethylphenyl)-1,2,4-oxadiazol-5-yl-acetic acid were converted to the reactive intermediate by the procedure of Example 8A. Using 15 ml of dry carbon tetrachloride, 0.4 ml of thionyl chloride and about 0.02 ml of dimethylformamide. After 5 minutes refluxing, the purple solution was completely evaporated in vacuo and the residue was dissolved in 6 ml of dry ethyl acetate. The resulting solution was added quickly to the first solution after that solution had regained room-temperature (about 20° C.). The addition of the "acid chloride" caused a temperature rise of about 5° C. and the reaction mixture was stirred for 30 minutes at 30° C.

The reaction mixture was poured into 175 ml of ice-water and the pH was adjusted to 7.0. The layers were separated, the organic layer was discarded and the aqueous layer was washed twice with 50 ml of portions of diethyl ether. The aqueous layer was brought to pH 3.7 and then was extracted four times with 25 ml portions of ethyl acetate. The obtained extracts were combined, washed with a small volume of ice-water, treated with activated carbon, filtered, dried over anhydrous magnesium sulfate and again vacuum filtered. Complete evaporation of the almost colorless filtrate and extensive drying of the residue in vacuo gave 650 mg of solid 7-{[3-(2,4,6-trimethylphenyl)-1,2,4-oxadiazol-5-yl]-acetamido}-cephalosporanic acid. This, according to thin-layer chromatography not completely pure, crude product was purified by means of column chromatography. However, the IR spectra of crude and pure product were scarely different.

IR (KBr-disc, values in cm$^{-1}$): ±3500 and ±2600, 3280, 1780, 1735, 1700, 1660, 1610, 1575, 1540, 1380 and/or 1355 and 1230 (very intensive).

EXAMPLE 10
7-[(3-methyl-1,2,4-oxadiazol-5-yl)-acetamido]-cephalosporanic acid While continuously maintaining dry conditions by passing dry nitrogen over the surface of the liquid reaction mixture, a solution of 10 mmol of trimethylsilyl 7-isocyanato-cephalosporanate in 19 ml of toluene was added quickly to a solution of 1.42 g (10 mmol) of crude (92–95% purity) and possibly slightly wet 3-methyl-1,2,4-oxadiazol-5-yl-acetic acid in 25 ml of dry dichloromethane. The solution also contained 0.05 ml of N-vinyl-imidazole as catalyst and a relatively fast reaction was evident from the rapid evolution of carbon dioxide and from a quickly formed precipitate which gradually dissolved during the further course of the reaction. The precipitate is the sparingly soluble mixed anhydride formed by addition of the carboxylic acid to the isocyanate. Decomposition of the labile mixed anhydride chiefly to the soluble trimethylsilyl ester of the desired cephalosporin and carbon dioxide was directed and assisted by the catalyst.

Evolution of carbon dioxide was substantially ceased after 4 hours stirring at room temperature and dichloromethane was removed from the solution by concentration in vacuo. The remaining solution was slowly poured into a well stirred mixture of 50 ml of ice-water and 50 ml of ethyl acetate while simultaneously dilute sodium hydroxide was added to maintain the pH at 7.0. The layers were separated and the organic layer discarded. The aqueous layer was repeatedly extracted with ethyl acetate beginning at pH 5.5, followed by extractions at pH 5.0, 4.5, 4.0, 3.5 and finally at pH 3.0 to effect a separation between the desired product and the relatively minor amount of the by-product N,N'-dicephalosporanyl urea. The extracts of pH 5.5 to 4.5 containing only small amounts of the desired product and the aqueous-layer of pH 3.0 still containing some of it were discarded. The extracts of pH 4.0 to 3.0 were combined, washed with a small volume of ice-water, dried over anhydrous magnesium sulfate, filtered, and completely evaporated in vacuo. The residue was triturated with diethyl ether, vacuum filtered and washed with diethyl ether. After extensive drying in vacuo the final, crystalline solid 7-[(3-methyl-1,2,4-oxadiazol-5-yl)-acetamido]-cephalosporanic acid weighed 2.3 g (about 58% yield). Since it contained a maximum of 5 mol % of the urea, purity of the final product was over 90% by weight (according to TLC and PMR spectrum).

IR (KBr-disc, values in cm$^{-1}$): ±3500 and ±2600, 3285, 1780, 1740, shoulders at ±1720 and 1710, 1390 and/or 1350, 1230.

PMR (60 Mc, d$_6$-DMSO, 2,2-dimethyl-silapentane-5-sulfonate as internal reference, δ-values in ppm): 2.05 (s, 3H), 2.34 (s, 3H), 3.6 (broad s, 2H), 4.05 (s, 2H), 4.87 (q, $J_{AB}$=12.7 cps) and ±5.2 (d, J=4.7 cps) together 3H, ±5.7 (q, J=4.7 and J'=8.2 cps, 1H), ±9.3 (d, J'=8.2 cps, about 0.8H).

EXAMPLE 11

The following penicillins, cephalosporins and desacetoxy-cehalosporins were prepared by the method of Example 10 starting with the appropriate 1,2,4-oxadiazole acetic acid and the trimethylsilyl ester of 6-isocyanato-penicillanic acid (6-IPA) or of 7-isocyanato-cephalosporanic acid or of 7-isocyanato-desacetoxycephalosporanic (7-I(D)CA):

A. 6-{[3-(2,6-dichlorophenyl)-1,2,4-oxadiazol-5-yl]-acetamido}penicillanic acid;
B. Sodium 6-[(3-methyl-1,2,4-oxadiazol-5-yl)-acetamido]-penicillanate H$_2$O;
C. 7-{[3-(2,6-dichlorophenyl)-1,2,4-oxadiazol-5-yl]-acetamido}cephalosporanic acid;
D. 7-[(5-methyl-1,2,4-oxadiazol-3-yl)-acetamido]-cephalosporanic acid;
E. 7-{[3-(2,6-dichlorophenyl)-1,2,4-oxadiazol-5-yl]-acetamido}desacetoxycephalosporanic acid;
F. 7-[(3-methyl-1,2,4-oxadiazol-5-yl)-acetamido]-desacetoxycephalosporanic acid;
G. Sodium 6-[(3-ethyl-1,2,4-oxadiazol-5-yl)-acetamido]-penicillanate H$_2$O;
H. DL-6[α-methyl-(3-methyl-1,2,4-oxadiazol-5-yl)-acetamido]-penicillanic acid;
I. DL-7-[α-methyl-(3-methyl-1,2,4-oxadiazol-5-yl)-acetamido]-cephalosporanic acid;
K. DL-7-[α-methyl-(3-ethyl-1,2,4-oxadiazol-5-yl)-acetamido]-cephalosporanic acid;
L. 7-[(3-ethyl-1,2,4-oxadiazol-5-yl)-acetamido]-cephalosporanic acid, and
M. Sodium 6-[α-methyl-(3-ethyl-1,2,4-oxadiazol-5-yl)-acetamido]-penicillanate H$_2$O.

With the few exceptions indicated below, all reactions were performed at room temperature (about 20° C.), with equimolar amounts of isocyanate and carboxylic acid and with 5–10 mol % of the catalyst, N-vinylimidazole. The trimethylsilyl esters of 6-IPA and 7-I(D)CA were employed in the solid, over 90% pure state. Trimethylsilyl 7-isocyanato-cephalosporanate was used in the form of good quality, stable toluene solutions of determined content.

For each example, there is given the reaction medium, the approximate reaction time, some indications of the purity of the final product, the yield and the IR (KBr-disc, values in cm$^{-1}$) and/or the PMR spectrum (60 Mc, d$_6$-DMSO, 2,2-dimethyl-silapentene-5-sulfonate as internal reference, δ-values in ppm). Isolation procedures were similar to that of Example 10, but of course adapted to the individual compound. Yields were obtained in all cases in the first run and the yield figures therefore have no absolute value.

A. Dichloromethane; 2 hours; isocyanate in 10 mol % excess; slightly yellow crystals; purity at least 95%; yield 90% (based on the acid, 80% based on isocyanate).

IR: ±3500 and ±2600, 3300, 1780, ±1730, 1680, 1580, 1560, ±1540, 1430, 1380, 800 and 785.

PMR: 1.5 and 1.65 (2 singlets, 6H), 4.3 (coinciding singlets, 3H), ±5.6 (multiplet, 2H), 7.7 (narrow split patt., 3H), and 9.25 (d, J≈8.5 cps, 0.8H).

B. Dichloromethane; 2 hours; colorless crystalline solid; purity over 90%; yield 52%.

IR: ±3350, ±3400–3600, 1780, 1690, 1620, ±1570, 1400, 1380 sh, 1350 sh, 1330 and 1250.

PMR: 1.51 and 1.62 (2 singlets, 6H), 2.35 (s, 3H), 4.07 (s, 2H), 4.2 (coinciding singlets, ±3H), 5.45 (centre of multiplet, 2H), 9.1 (d, J≈8.5 cps, 0.8H).

C. Dichloromethane-toluene mixture; 6 hours; purity about 90% yield 43%.

IR: ±3500 and ±2600, 3300, 1780, 1735, shoulders at ±1720 and 1700, 1680, 1580, 1560, ±1540, 1435, 1410 sh, 1380, 1350, 1230 (very intensive), 795 and 785.

PMR: 2.07 (s, 3H), 3.6 (broad s, 2H), 3.76, 4.29 (s, 2H), 4.92 (q, $J_{AB}$=12.7 cps) and ±5.2 (d, J=4.7 cps) together 3H, ±5.75 (q, J=4.7 and J'=8.0 cps, 1H), 7.7 (narrow split. patt., 3H) and 9.45 (d, J'=8.0 cps, 0.8H).

D. Dichloromethane-toluene-tetrahydrofuran mixture; 7 hours; purity over 90%; yield 10%.

IR: ±3500 and ±2600, 3290, 1780, 1735, 1715, 1660, 1690, 1550, 1430, 1385, 1370 and 1240.

PMR: 2.05 (s, 3H); 2.58 (s, 3H), 3.6 (broad s, 2H), 3.76, 4.90 (q, $J_{AB}$=12.7 cps) and ±5.15 (d, J=4.7 cps) together 3H, ±5.7 (q, J=4.7 and J'=8.0 cps, 1H), and 9.2 (d, J'=8.0 cps, 0.8H).

E. Dichloromethane; 6 hours; catalysts: N-vinylimidazole and a trace of 4-methoxy-pyridine-N-oxide.1-H$_2$O; purity over 95%; yield over 90% (based on acid, over 80% on isocyanate, which was used in 10% excess).

IR: ±3500 and ±2600, 3300, 1778, ±1700 (broad, intensive), 1580, 1560, 1540, 1440, 1410 sh, 1380 sh, 1360, ±1240, 800 and 790 sh.

PMR: 2.08 (s, 3H), 3.5 (q, $J_{AB}$≈17.5 cps, 2H), 4.29 (s, 2H), ±5.15 (d, J=4.5 cps, 1H), ±5.65 (q, J=4.5 and J'=8.0 cps, 1H), 7.7 (narrow split.patt., 3H) and 9.4 (d, J'=8.0 cps, 0.9H).

F. Dichloromethane; 2 hours; purity at least 95%; yield 68%.

IR: ±3500 and ±2600, 3300, 1785, 1720, 1665, 1635, 1595, 1550, 1435, 1400, 1370 (strong), 1345 and 1240.

PMR: 2.06 (s, 3H), 2.34 (s, 3H), 3.5 (q, $J_{AB}$≈18 cps, 2H), 4.06 (s, 2H), ±5.1 (d, J=4.5 cps, 1H), ±5.6 (q, J=4.5 and J'=8.0 cps, 1H) and 9.3 (J'=8.0 cps, 0.9H).

G. Dichloromethane; 5 hours; colorless crystalline solid; purity at least 90%; yield 60%.

IR: ±3450; ±3300, 1780, 1685, 1600, 1580 and 1560.

PMR: 1.25 (t, J=7.5 cps, 3H), 1.51 and 1.61 (2 singlets, 6H), 2.7 (q, J=7.5 cps, 2H), 3.98, 4.03 (s) and 4.08 (s) together about 5H, 5.45 (centre of multiplet, 2H) and 9.1 (d, J~8.5 cps, 0.9H).

H. Dichloromethane; 2 hours; slightly colored solid; purity about 90%; yield 15%.

PMR: about 1.4 to 1.7 (6 lines, 9H), 2.34 (s, 3H), 4.08 (2 singlets, δν=1.3 cps, 1H), 4.33 (q, J=7.5 cps, 1H), about 5.2 to 5.6 (multiplet, 2H), and 9.1 (2 overlapping doublets, 0.8H).

I. Dichloromethane-toluene mixture; 9 hours; slightly colored solid; purity about 90%; yield 40%.

IR: ±3500 and ±2600, 3290, 1780, 1740, shoulders at 1720 and 1700, 1660, 1580, 1550, 1230 (very intensive).

PMR: 1.48, 1.50 and 1.62 (2 doublets, δν=1.2 cps, J=7.2 cps, 3H), 2.06 (s, 3H), 2.35 (s, 3H), (3.6 broad s, 2H), 4.25 (2 quarters, δν≈1.2 cps, J=7.2 cps, 1H), 4.90 (q, J$_{AB}$=12.6 cps) and ±5.2 (2 doublets, δν≈1.0 cps, J=4.8 cps) together 3H, ±5.65 (2 multiplets, 1H), 9.35 (2 doublets, δν≈4 cps, J'≈8 cps, 0.8H).

K. Dichloromethane-toluene mixture; 10 hours; colorless solid; purity over 90%; yield 45%.

IR: ±3500, ±2600, 3300, 1785, 1745, shoulders at 1725 and 1705, 1660, 1585, 1560 and 1235 (very intensive).

PMR: 1.4 (t, J=7.5 cps, 3H), 1.55 (2 doublets, δν≈1.6 cps, J=7.2 cps, 3H), 2.06 (s, 3H), 2.75 (q, J=7.5 cps, 2H), 4.25 (2 quartets, δν≈1.2 cps, J=7.2 cps, 1H), 3.6 (broad s, 2H), 4.90 (q, J$_{AB}$=12.6 cps), ±5.15 (2 doublets δν≈1.0 cps, J=4.8 cps) together 3H, ±5.7 (2 multiplets, 1H) and 9.35 (2 doublets, δν≈3.5 cps, J'≈8 cps, 0.8H).

L. Dichloromethane-toluene mixture; 9 hours; crystalline solid; purity about 95%; yield 60%.

IR: ±3500 and ±2600, 3300, 1780, 1740, shoulders at 1720 and 1705, 1665, 1590, 1550 and ±1240 (very intensive).

PMR: 1.25 (t, J=7.5 cps, 3H), 2.06 (s, 3H), 2.75 (q, J=7.5 cps, 2H), 3.6 (broad s, 2H), 4.07 (s, 2H), 4.90 (q, J$_{AB}$=12.8 cps) and ±5.15 (d, J=4.7 cps) together 3H, ±5.75 (q, J=4.7 cps and J'=8.0 cps, 1H) and 9.35 (d, J'=8.0 cps, 0.8H).

M. Dichloromethane; 4 hours; crystalline solid; purity about 95%; yield 30%.

IR: ±3500, ±3350, 1785 and 1775, 1680, ±1600, 1580 and ±1550.

PMR: 1.25 (t, J=7.5 cps, 3H), about 1.4 to 1.7 (6 lines, 9H); 2.75 (q, J=7.5 cps, 2H), 4.09 (2 singlets, δν=1.7 cps, 1H), 4.34 (q. J=7.2 cps, 1H), about 5.2 to 5.6 (multiplet, 2H) and 9.1 (2 doublets, 0.8H).

EXAMPLE 12

The following substituted 1,2,4-oxadiazol-5-yl-acetic acids were prepared by the method of Examples 1 and 2 by reaction of a slight excess of 3,5-disubstituted-1,2,4-oxadiazole with the 1:1 complex of n-butyl lithium with TMEDA in a toluene/n-hexane mixture (or alternatively with n-butyl lithium in a tetrahydrofuran/n-hexane mixture) followed by the reaction of the intermediate product with solid carbon dioxide.

A. 3-benzyl-1,2,4-oxadiazol-5-yl-acetic acid
B. 3-ethyl-1,2,4-oxadiazol-5-yl-acetic acid
C. α-methyl-3-methyl-1,2,4-oxadiazol-5-yl-acetic acid
D. α-methyl-3-ethyl-1,2,4-oxadiazol-5-yl-acetic acid
E. 3-methoxymethyl-1,2,4-oxadiazol-5-yl-acetic acid.

For each product, there is given below the initial 1,2,4-oxadiazole, the lithiation method, solvent mixture, the reaction temperature and the approximate reaction time of the lithiation, some indications of the purity of the final product, the melting point in case of solid final products and the IR (KBr-disc, values in cm$^{-1}$) and/or the PMR spectrum (60 Mc, CDCl$_3$, tetramethylsilane as internal reference, δ-values in ppm). Yield figures have no definite value as they were derived from the first or from the second experiment.

A. 3-benzyl-5-methyl-1,2,4-oxadiazole (6.95 g); n-butyl lithium/THF-hexane; below −80° C., 80 minutes. Yield (crude 4.3 g. After crystallization from toluene (at 60° C. dissolved) 3.6 g (41%). m.p.: 106°-109° C. (with slow decarboxylation).

Purity over 96%.

IR: ±3430, 1730, 1585, ±1600 sh, 1498, 1420, 1390, 1365, 1300, 1248, 1230, 1215, 1165, 720 and 705.

PMR: 3.87 (s, 2H), 4.06 (s, 2H), 7.27 (s, 5H), ~9.8 (s, about 1H).

B. 3-ethyl-5-methyl-1,2,4-oxadiazole (22.4 g); n-butyl lithium; TMEDA/toluene-hexane; −70° to −80° C.; 2 hours; Yield 16 g (50%); purity over 96%; m.p. 86°-90° C. (with slow decarboxylation); crystallization (not necessary) possible by dissolution in a minimum amount of a 2:1 mixture of carbon tetrachloride and chloroform at about 45° C. followed by slow addition of hexane.

IR: ±3440, 1730, 1715 and 1580.

PMR: 1.35 (t, J=7.5 cps, 3H), 2.8 (q, J=7.5 cps, 2H), 4.04 (s, 2H), ~10.4 (about 1H).

C. 3-methyl-5-ethyl-1,2,4-oxadiazole (22.4 g); n-butyl lithium; TMEDA/toluene-hexane; −70° to −80° C.; 1.5 hours; Yield 7 g (22%); Purity over 96%; m.p.: 64.5°-65° C. (slow decarboxylation sets in at 57° C.).

IR: ±3450, ±1730, 1600.

PMR: 1.70 (d, J=7.5 cps, 3H), 2.41 (s, 3H), 4.16 (q, J=7.5 cps, 1H), ~9.6 (s, about 1H).

D. 3,5-diethyl-1,2,4oxadiazole (24.2 g); n-butyl lithium; TMEDA/toluene-hexane; −70° to −80° C.; 3 hours; Yield 18.1 g (about 53%); Purity about 95% (contains a small amount of valeric acid); m.p.; 30°-32° C.

IR: ±3500, ±2600, ±1740, 1580.

PMR: 1.35 (t, J=7.5 cps, 3H), 1.70 (d, J=7.5 cps, 3H), 2.75 (q, J=7.5 cps, 2H), 4.6 (q, J=7.5 cps, 1H), and ~9.4 (s, about 1H).

E. 3-methoxymethyl-5-methyl-1,2,4-oxadiazole (40 g); n-butyl lithium; TMEDA/toluene-hexane; −75° to −80° C.; 150 minutes; Yield 31.5 g (about 58%); Purity over 96%; melting and extensive decarboxylation between about 50° and 75° C.

IR: ±3450, 1725, 1590, 1410, 1395, 1360, 1335, 1325, 1240, 1210 (sh), 1195, 1170, 1005.

PMR: 3.45 (s, 2H), 4.07 (s, 2H), 4.59 (s, 2H), and 10.65 (s, about 1H).

EXAMPLE 13

Sodium 6-[(5-methyl-1,2,4-oxadiazol-3-yl)-acetamido]-penicillanate 1.42 g (10 mmol) of 5-methyl-1,2,4-oxadiazol-3-yl-acetic acid was added to 20 ml of dry carbon tetrachloride and at room temperature, 1 ml of thionyl chloride and 2 drops of dimethylformamide were added to the suspension. The mixture was gently refluxed for 10 minutes to obtain a clear solution and a complete coversion of the substituted acetic acid into its acid chloride.

At the same time, a suspension of 2.15 g (10 mmol) of 6-amino-penicillanic acid in 30 ml of dry ethyl acetate was reacted with 2.8 ml (20 mmol) of triethylamine and 2.5 ml (20 mmol) of trimethylchlorosilane and then was stirred for 30 minutes at room temperature. First, 1.2 ml (10 mmol) of quinoline and then the solution of the acid chloride in carbon tetrachloride were added to this mixture and the fast addition of the dissolved acid chloride resulted in a rise of about 10° C. in temperature to about 30° C. The reaction mixture was additionally stirred for 30 minutes and subsequentlly poured into 50 ml of ice-water. The pH was adjusted to 7.0 and the layers separated. The organic layer was discarded and the aqueous layer was extracted once with 30 ml of diethyl ether. In order to obtain the desired penicillin, the aqueous layer was extracted six times at pH 3.0 with a 1:1 mixture of diethyl ether and ethyl acetate. The organic layers were combined, washed twice with a small volume of ice-water, treated with activated carbon, dried over anhydrous magnesium sulfate, filtered and concentrated in vacuo to a volume of about 20 ml. 40 ml of diethyl ether were added, and then a solution of sodium α-ethylcaproate in ethyl acetate was added till no further precipitation occurred. The solid precipitate was collected on a vacuum filter, repeatedly washed with a 2:1 mixture of diethyl ether and ethyl acetate and finally with diethyl ether alone. After extensive drying in vacuo, the final product of sodium 6-[(5-methyl-1,2,4-oxadiazol-3-yl)-acetamido]-penicillanate weighed 2.5 g.

Its structure and good state of purity was confirmed by IR and PMR spectra. According to the PMR spectrum, the final product contained 1 mole of water per mole of penicillin.

IR: (KBr-disc, values in cm$^{-1}$): ±3400, 1775, 1685, 1610, 1590, ±1540, 1390.

PMR: (60 Mc, d$_6$-dimethylsulfoxide, 2,2-dimethylsilapentane-5-sulfonate reference, δ-values in ppm): 1.51 and 1.62 (2 singlets, 6H), 2.58 (s, 3H), 3.78 (s, 2H), 4.02 (s, 1H), 5.45 (centre of multiplet, 2H) and 8.9 (d, J≈8.5 cps, 0.9H).

EXAMPLE 14 methyl (α-phenyl)-3-methyl-1,2,4-oxadiazol-5-yl-acetate

A solution of 14 g (80 mmol) of 3-methyl-5-benzyl-1,2,4-oxadiazole and 14 ml of TMEDA in 140 ml of toluene was cooled to −65° C. and a solution of about 75 mmol of n-butyl lithium in 80 ml of an 1:1 mixture of n-hexane and toluene was added dropwise. The rate of addition was adjusted to a reaction temperature between −60° and −70° C. and the reaction mixture was stirred additionally for 2.5 hours at −75° C. and then was poured onto finely divided solid carbon dioxide. Approximately 3 hours later, 120 ml of water and 120 ml of diethyl ether were added and the resulting two layer system was treated with dilute hydrochloric acid until the vigorously stirred mixture had attained a pH of 8.0. The layers were separated and the organic layer was discarded. The aqueous layer was purified by three extractions with 30 ml portions of diethyl ether at pH 8.0. The aqueous layer was mixed with 80 ml of ethyl acetate, cooled below 0° C. and acidifed to pH 3.0 with a dilute hydrochloric acid. The layers were separated and the aqueous layer was once more extracted with 80 ml of ethyl acetate. The organic extracts were combined, washed once with a small volume of ice-water and shaken with anhydrous magnesium sulfate for a few minutes. The salt was filtered off in the cold and the resulting colorless solution was treated carefully with a simultaneously prepared solution of diazomethane in diethyl ether (prepared in the usual way from 25.6 g of N-nitroso-N-methyl-p-toluenesulfonamide). The solution of diazomethane in ether was directly distilled into the solution of the carboxylic acid in ethyl acetate and the reaction was continued until no further discoloration of the reaction mixture was noticed. The resulting solution was directly decolorized with a small amount of acetic acid, was washed three times with a small volume of neutral water, dried over anhydrous magnesium sulfate, filtered and evaporated completely in vacuo to obtain 10 g of residual oil. This crude product was only slightly contaminated by the starting material and the pure methyl (α-phenyl)-3-methyl-1,2,4-oxadiazol-5-yl-acetate was obtained by distillation in vacuo in a yield of 6 g with a boiling point of 135° C. at 0.8 mm Hg and a refractive index $n_d^{20.3} = 1.5230$.

IR: (KBr-disc, values in cm$^{-1}$): 1750, 1580, 1498, 1435, 1390, 1340, 1270, 1220, 1160, 1010, 740 and 650.

PMR: (60 Mc, CDCl$_3$, TMS, δ-values in ppm): 2.37 (s, 3H), 3.77 (s, 3H), 5.26 (s, 1H), about 7.4 (narrow multiplet, 5H).

EXAMPLE 15

5-methyl-1,2,4-oxadiazol-3-yl-acetamide

A mixture of 6.5 g of 5-methyl-1,2,4-oxadiazol-3-yl-acetic acid, 0.21 ml of dimethylformamide, 4.6 ml of thionyl chloride and 100 ml of carbon tetrachloride was refluxed gently for 12 minutes and the resulting brownish solution was added over 10 minutes to 100 ml of 25% ammonium hydroxide. During the addition, the well stirred reaction mixture was cooled with an ice-salt mixture and then the reaction mixture was stirred at room temperature for 1 hour. 20% hydrochloric acid was added until a pH of 8.0 was reached and the layers were separated. The aqueous layer was extracted once with 10 ml of carbon tetrachloride and the combined organic layers were washed once with 10 ml of water. The organic layer was discarded and the combined aqueous layers were evaporated in vacuo. The residue was submitted to continuous extraction with acetone for 16 hours to obtain 7 g of a semi-solid brownish product. The greater part of this product was dissolved in dry ethyl acetate and this solution was again evaporated to dryness. The residue was dissolved in ethanol and the solution was treated with activated carbon and again evaporated. The solid residue was dissolved in hot acetone followed by the addition of n-hexane until the solution became turbid. After standing several hours at room temperature and finally at 0° C., the crystals were vacuum filtered, were washed with a cold 9:1 mixture of n-hexane and acetone, and dried in vacuo to obtain 4.8 g (72% yield) of slightly colored 5-methyl-1,2,4-oxadiazol-3-yl-acetamide with a m.p. of 112°–114° C.

IR: (KBr-disc, values in cm$^{-1}$): 3380 and 3320, 1680, 1630, 1590, 1420, 1380, 1270, 1185 and 895.

PMR: (60 Mc, d$_6$-dimethylsulfoxide, 2,2-dimethylsilapentane-5-sulfonate, δ-values in ppm): 2.58 (s, 3H), 3.60 (s, 2H), 7.1 and 7.6 (centres of broad absorptions, about 2H).

EXAMPLE 16 methyl-5-methyl-1,2,4-oxadiazol-3-yl-acetate

Using the procedure of Example 10, 10 g of crude 5-methyl-1,2,4-oxadiazol-3-yl acetic acid were reacted with diazomethane to obtain 5.9 of methyl-5-methyl-1,2,4-oxadiazol-3-yl-acetate with a b.p. of 70°–72° C. at 0.6–0.7 mm and a refractive index $n_D = 1.4495$.

IR: (NaCl windows, values in cm$^{-1}$): 3020, 2980, 2865, 1750, 1595.

PMR: (60 Mc, CDCl$_3$, TMS, δ-values in ppm): 2.59 (s, 3H), 3.73 (s, 3H), 3.80 (s, 2H).

EXAMPLE 17 cyclohexyl 5-methyl-1,2,4-oxadiazol-3-yl-acetate 8 g (56.3 mmol) of 5-methyl-1,2,4-oxadiazol-3-yl-acetic acid were suspended in 8 g (80 mmol) of re-distilled, dry cyclohexanol and 8 g (52.2 mmol) of phosphorous oxychloride were added dropwise under anhydrous conditions over about 7 minutes to the mixture. During the addition, the mixture was heated on a steam bath and heating was continued for 45 minutes. After the reaction mixture had cooled to room temperature, 75 ml of ice-water and 50 ml of diethyl ether were added and the mixture was stirred until a clear two-layer system was obtained. The flask was placed in an ice-salt bath and solid potassium hydroxide was added until a pH of 10.5 was reached. The layers were separated and the aqueous layer was extracted three times with 40 ml portions of diethyl ether. The four ethereal extracts were combined, washed once with a small volume of ice-water and subsequently concentrated in vacuo. The 10 g of residue was distilled in vacuo to obtain 7.9 g (62% yield) of cyclohexyl 5-methyl-1,2,4-oxadiazol-3-yl-acetate with a b.p. of 120°–121° C. at 0.9–1.0 mm and a refractive index $n_D^{25} = 1.4715$.

IR: (NaCl windows, values in cm$^{-1}$): 2960 and 2880, 1740 and 1595.

PMR: (60 Mc, CDCl$_3$, TMS, δ-values in ppm): about 1.05 to 2.2 (broad, 10H), 2.58 (s, 3H), 3.75 (s, 2H) and about 4.85 (broad, 1H).

In the same way Cyclopentyl 5-ethyl-1,2,4-oxadiazol-3-yl-acetate was prepared with a b.p. of 108° C. at 0.5 mm Hg and a refractive index $n_D^{25} = 1.469$ in 43% yield, from 5-ethyl-1,2,4-oxadiazol-3-yl-acetic acid and cyclopentanol:

IR (NaCl windows, values in cm$^{-1}$): 3000, 2915 (sh), 1755, 1600, 1430, 1400, 1350, 1280, 1220–1240, 1185, 1060, 1000.

PMR: (CDCl$_3$, 60 Mc, TMS, δ-values in ppm): 1.39 (t, J=7.5 cps) and from about 1.5 to 2.2 together 11H, 2.91 (q, J=7.5 cps, 2H), 3.76 (s, 2H), about 5.25 (centre of multiplet, 1H).

EXAMPLE 18

7-[(5-methyl-1,2,4-oxadiazol-3-yl)-acetamido]-3-azidomethyl-3-cephem-4-carboxylic acid A mixture of 0.71 g (5 mmol) of 5-methyl-1,2,4-oxadiazol-3-yl-acetic acid, 0.5 ml of thionyl chloride, 1 drop of dimethylformamide and 10 ml of dry carbon tetrachloride was refluxed gently for 13 minutes. Using anhydrous conditions, the solvent was removed in vacuo and the colored residue was dissolved in 10 ml of dry ethyl acetate.

In the meantime, 1.39 ml of triethylamine and 1.26 ml of trimethyl-chlorosilane were added successively to a suspension of 1.225 g (4.8 mmol) of 7-amino-3-azidomethyl-3-cephem-4-carboxylic acid [Willner, Journal of Antibiotics, Vol. 25 (No. 1), p. 64 (Jan. 1972)] in 12.5 ml of ethyl acetate. The mixture was stirred for 45 minutes at room temperature and after cooling to 0° C., there were added successively 0.66 ml of quinoline and the prepared solution of the acid chloride in ethyl acetate. After 5 minutes, the ice-bath was removed and the reaction mixture was then stirred for 60 minutes at room temperature. The reaction mixture was poured into a well stirred ice-cold mixture of 50 ml of water and 40 ml of ethyl acetate at a pH of 2. The pH was brought to 7 and the layers were separated. The organic layer was discarded and the aqueous layer was extracted once with 50 ml of ethyl acetate. The aqueous layer was once again extracted with 50 ml of ethyl acetate at pH 6.0 and then extracted six times with 50 ml volumes of ethyl acetate successively at pH 5.0, 4.0 (2 times), 3.5 (2 times) and 1.0. These extracts were combined, centrifuged to remove some non-soluble solid material, washed twice with a small volume of ice-water, treated with activated carbon, dried over anhydrous magnesium sulfate, filtered and evaporated completely in vacuo. The residue was triturated with diethyl ether, vacuum filtered, washed with diethyl ether and dried in vacuo to constant weight to obtain 1.17 g (64% yield) of 7-[(5-methyl-1,2,4-oxadiazol-3-yl)-acetamido]-3-azidomethyl-3-cephem-4-carboxylic acid. The final product consisted of about 90% of the desired compound and about 10% of the corresponding Δ$^2$-cephem derivative.

IR: (KBr-disc, values in cm$^{-1}$): ±3450 and ±2600, 3305, 2135, 1790, 1710, 1660, 1585 and 1540.

PMR: (d$_6$-dimethylsulfoxide, 60 Mc, 2,2-dimethyl-silapentane-5-sulfonate, δ-values in ppm): 2.58 (s, 3H), 3.3 to 3.95 (q, J$_{AB}$ 18.3 cps), 3.76 (s) and about 3.8 to 4.6 (q, J$_{AB}$=13.1 cps) together 6H, ±5.15 (d, J=4.7 cps, 1H), ±5.75 (q, J=4.7 cps, J'=8.3 cps, 1H) and 9.3 (d, J'=8.3 cps, 0.9H).

EXAMPLE 19

R-sulfoxide of 7-[(5-methyl-1,2,4-oxadiazol-3-yl)-acetamido]-3-azidomethyl-3-cephem-4-carboxylic acid A solution of 730 mg (2 mmol) of 7-[(5-methyl-1,2,4-oxadiazol-3-yl)-acetamido]-3-azidomethyl-3-cephem-4-carboxylic acid (prepared as in Example 18) in 20 ml of anhydrous tetrahydrofuran (THF) was cooled to −75° C. A solution of 400 mg (2.5 mmol) of N,N-dichlorourethane (Cl$_2$NCO$_2$C$_2$H$_5$) in 7.5 ml of anhydrous THF was added to this solution at −70° to −75° C. The resulting reaction mixture was stirred for 1 hour at −70° to −75° C. and subsequently was poured into a well stirred mixture of 300 ml of ice-water and 200 ml of ethyl acetate. The layers were separated at a pH of 1.7, and the aqueous layer was extracted three times more with 200 ml volumes of ethyl acetate. The four ethyl acetate layers were combined and twice washed with 100 ml volumes of a saturated aqueous solution of sodium chloride. Since the original aqueous layer still contained the desired product according to thin-layer chromatography, it was combined with the 200 ml of water used for washing the organic layer. The combined aqueous layers were acidified to a pH of 1.7 and then was extracted twice with 100 ml volumes of n-butanol. The butanol extracts were combined, washed with a small volume of ice-water and evaporated to dryness in vacuo to obtain a first crop of 110 mg of product.

The ethyl acetate layer was mixed with 100 ml of water, and then sodium bicarbonate was added to give a pH of 7.5. The layers were separated and the ethyl acetate layer was extracted twice more with 50 ml volumes of water. The ethyl acetate layer was discarded, and the three aqueous layers were combined, mixed with 500 ml of ethyl acetate and acidified to pH 1.7. The layers were separated and the aqueous layer was extracted twice more at pH 1.7 with 100 ml volumes of ethyl acetate and once with 100 ml of ethyl acetate at pH 1.0. The aqueous layer was discarded and the combined ethyl acetate layers were dried over anhydrous magnesium sulfate, filtered and concentrated in vacuo to small volume whereupon the second crop of 148 mg was precipitated by addition of n-hexane. IR-spectra of the two crops were virtually identical for a yield of 258 mg (35%) of R-sulfoxide of 7-[(5-methyl-1,2,4-oxadiazol-3-yl)-acetamido]-3-azidomethyl-3-cephem-4-carboxylic acid.

IR: (KBr-disc, values in cm$^{-1}$): ±3450, ±3300, 2550, 2130, 1790, 1720, 1680, ±1655 (sh), 1590, ±1540, ±1040.

PMR: (d$_6$-DMSO, 60 Mc, δ-values in ppm, DSS as reference): 2.58 (s, 3H), 3.75 (s) and 4.0 (centre of about 0.8 ppm wide AB-q, J≈16.5 cps) and 4.2 (centre of about 0.55 wide AB-q, J≈13.5 cps) together 6H, 4.85 (d, J=4.6 cps, 1H), 5.7 (q, J=4.6 cps and J'≈8.0 cps, 1H), 9.7 (d, J'≈8.0 cps, about 0.8H).

EXAMPLE 20

N-{(5-methyl)-isoxazol-3-yl}-3-methyl-1,2,4-oxadiazol-5-ylacetamide

The method employed below is in essence outlined in "Houben-Weyl, Methoden der Organischen Chemie", Band 11/2, p. 5 and 6. 7.8 g (0.055 mol) of 3-methyl-1,2,4-oxadiazol-5-yl-acetic acid were dissolved in 80 ml of a dry solvent mixture consisting of equal volume parts of dioxane and toluene. 6.9 g (0.07 mol) of 5-methyl-3-amino-isoxazole dissolved in 50 ml of the same mixture of dioxane and toluene and 4.2 g (0.031 mol) of phosphorous trichloride (PCl$_3$) were successively added thereto. After the addition of PCl$_3$, the mixture became lukewarm and a deposit of a heavy yellowish oil was noticed. Within a very short time, crystallization of the oil took place and the mixture was heated for 5 minutes at 90° C. on the steam-bath. Afterwards, the mixture was additionally stirred for 60 minutes at room temperature and then was evaporated in vacuo. The residue was suspended in 80 ml of water and the acidic suspension (pH of 1.5) was heated for 60 minutes on the steam-bath to decarboxylate remnants of the oxadiazolyl-acetic acid. The suspension was cooled and was continuously extracted with dichloromethane for 16 hours. The obtained extract was cooled to room temperature and the resulting mixture of crystals and solution were completely evaporated. The crystalline residue was dissolved in a slight excess of dichloromethane and the resulting solution was slowly cooled to room temperature, and then successively to 3° C., −15° C. and finally to −70° C. The crystals were quickly vacuum filtered, washed with dichloromethane at −70° C. and finally with n-heptane. After drying in vacuo, the N-{(5-methyl)-isoxazol-3-yl}-3-methyl-1,2,4-oxadiazol-5-yl-acetamide weighed 10.45 g (85.7% yield based on 3-methyl-1,2,4-oxadiazol-5-yl-acetic acid) and had a m.p. of 191°-193° C.

IR: (KBr-disc, values in cm$^{-1}$): 3240, 3290, 1715, 1650, 1605, 1585, 1500, 1450, 1365, 1280, 1220, 1045, 940, 900, 750 and 650.

PMR: (about 4:1 mixture of CDCl$_3$ and d$_6$-DMSO, 60 Mc, δ-values in ppm, TMS as reference): (s) and narrow d together at 2.4 (6H), 4.1 (s, 2H), 6.58 (narrow q, 1H), 10.5 (slightly broad s, 1H).

EXAMPLE 21

3-methyl-1,2,4-oxadiazol-5-yl-acetamide

The employed method is an adaptation of the method outlined in "Houben-Weyl, Methoden der Organischen Chemie", Band 11/2, p. 5 and 6. 8 g (0.056 M) of 3-methyl-1,2,4-oxadiazol-5-yl-acetic acid were dissolved at room temperature in 150 ml of a dry solvent mixture consisting of equal volume parts of dioxane and toluene and at room temperature, 3.5 g of dry, gaseous ammonia were introduced into the solution which resulted in the precipitation of the ammonium salt of the oxadiazolyl-acetic acid in the form of a white thick slush. While gaseous ammonia was introduced slowly below the surface of the vigorously stirred mixture, a solution of 4 g (0.029 mol) of phosphorous trichloride in 50 ml of the same solvent mixture of dioxane and toluene was introduced over a period of 10 minutes. During the addition, the mixture became lukewarm and attained a yellowish color. Then, the reaction mixture was heated at about 90° C. on the steam-bath for 5 minutes and the reaction mixture was stirred for 60 minutes at room temperature and then completely evaporated in vacuo. The residue was dissolved in 75 ml of water, and the resulting acidic solution (pH 2.0) was heated for 60 minutes on the steam-bath. The solution was cooled to room temperature, was saturated with sodium chloride and then continuously extracted for 16 hours with dichloromethane. The obtained extract was completely evaporated resulting in a crystalline residue which resisted several recrystallization attempts from various solvents. Therefore, the residue was filtered through a short silica column with diethyl ether. Ether was removed and the residue was recrystallized from a 9:1 mixture of diethyl ether and dichloromethane employing step-wise cooling of the solution from room temperature down to −70° C. (crystals washed with very cold diethyl ether) to obtain 5.1 g (64.5% yield) of 3-methyl-1,2,4-oxadiazol-5-yl-acetamide with a m.p. of 77°-77.5° C.

IR: (KBr-disc, values in cm$^{-1}$): 3180, ±3240, 1685, ±1635, 1595, 1445 (s), 1425, 1400, 1360, 1315, 1270, 1260, 1180, 1060, 890, 730 and 685.

PMR: (CDCl$_3$ and a trace of d$_6$DMSO, 60 Mc, δ-values in ppm, TMS as reference): 2.40 (s, 3H), 3.88 (s, 2H), ±6.6 and ±7.2 (centres of 2 broad abs., about 2H).

EXAMPLE 22

3-methyl-1,2,4-oxadiazol-5-yl-acetmorpholide

The employed method is an adaptation of the method outlined in "Houben-Weyl, Methoden der Organischen Chemie", Band 11/2, p. 5 and 6. To a mechanically stirred solution of 7.8 g (0.055 mol) of 3-methyl-1,2,4-oxadiazol-5-yl-acetic acid in a dry mixture of 50 ml of dioxane and toluene, which was prepared at room temperature, 12.3 g (0.014 mol) of freshly distilled morpholine were added. After a few minutes stirring, a thick precipitation of the morpholine salt of the oxadiazolyl-acetic acid took place and 4.2 g (0.031 mol) of phosphorous trichloride were added all at once to the vigorously stirred suspension resulting in a thick yellow slush and in a considerable rise of temperature. Shortly after the addition of PCl$_3$, the reaction mixture was heated for 5 minutes at about 90° C. on the steam-bath and then was stirred for 60 minutes at room temperature. The reaction mixture was completely evaporated in vacuo and the residue was dissolved in 75 ml of water. The solution at pH 1.5 was heated for 60 minutes on the steam-bath, and then was saturated with sodium chloride at room temperature. The solution in water was continuously extracted with dichloromethane for 16 hours and the obtained extract was evaporated. The residue first was crystallized from carbon tetrachloride and then from toluene, and then the hot solution was treated with activated carbon. The resulting colorless crystalline product was dried in vacuo to obtain 8.1 g (69.5% yield) of 3-methyl-1,2,4-oxadiazol-5-yl-acetmorpholide with a m.p. of 79°-80.5° C.

Elementary analysis: C$_9$H$_{13}$N$_3$O$_3$: Calculated: %C 51.18, %H 6.16, %N 19.90, O% 22.76. Found: %C 51.15, %H 6.10, %N 19.91, %O 22.84.

IR: (KBr-disc, values in cm$^{-1}$): 1650, 1595, 1450, 1395, 1240, 1130, 1045, 865, 2980, 2940, 2865, 1470 (sh), 1420, 1370 (sh), 1350, 1310, 1290, 1280, 1180, 1080, 1030 (sh), 985, 920, 900, 840 (sh), 770, 715, 680.

PMR: (CDCl₃, 220 Mc, δ-values in ppm, TMS as reference): 2.41 (s, 3H), 3.54 (centre of 3 or 4 lines, 2H), from 3.62 to 3.75 (at least 9 lines, 6H), 4.02 (s, 2H)

EXAMPLE 23

N'-(fur-2-yl-carbonyl)-3-methyl-1,2,4-oxadiazol-5-yl-acethydrazide

The employed method is an adaptation of the method outlined in "Houben-Weyl, Methoden der Organischen Chemie", Band 11/2, p. 5 and 6. Under anhydrous conditions and with powerful mechanical stirring, 5 g (0.063 mol) of pyridine and 6.3 g (0.05 mol) of fur-2-yl-carbonyl-hydrazide were added at room temperature successively to a solution of 6 g (0.042 mol) of 3-methyl-1,2,4-oxadiazol-5-yl-acetic acid in a mixture of 50 ml of dry dioxane and 50 ml of toluene. To the resulting clear solution was added all at once 3.4 g (0.025 mol) of phosphorous trichloride and a heavy, yellow oil appeared which solidified quickly. Subsequently, the reaction mixture was heated for 5 minutes at about 90° C. on the steam-bath followed by stirring at room temperature for 60 minutes. The reaction mixture was evaporated in vacuo and the residue was suspended in 75 ml of water. The acidic suspension at pH 2 was heated for 60 minutes on the steam-bath which resulted in a clear yellow solution. After cooling the solution to room temperature, crystallization of a yellowish solid took place and this product was isolated by vacuum filtration and was washed with ice-water. The product weighed 7.2 g and was recrystallized from acetone with step-wise cooling down to about −20° C. to obtain 5.1 g (about 46% yield) of a slight yellow crystalline solid of about 95% purity (according to TLC and PMR) of N-(fur-2-yl-carbonyl)-3-methyl-1,2,4-oxadiazol-5-yl-acethydrazide, m.p. of 169°–171° C.

IR: (KBr-disc, values in cm⁻¹): ±3180, 1700 and 1675, 1620, ±1590, ±1570, ±1510, 1480, 1435, 1205, 945 and 790.

PMR: (d₆-DMSO, 60 Mc, δ-values in ppm, DSS as reference): 2.36 (s, 3H), 4.04 (s, 2H), 6.65 (q, J=3.6 and J'=1.7 cps, 1H), 7.25 (q, J=3.6 and J"=0.7 cps, 1H), 7.9 (q, J'=1.7 and J"=0.7 cps, 1H), 10.35 (s, about 1.8H).

EXAMPLE 24

N'-(ethoxycarbonyl)-5-methyl-1,2,4-oxadiazol-3-yl-acethydrazide

The employed method is an adaptation of the method outlined in "Houben-Weyl, Methoden der Organischen Chemie", Band 11/2, p. 5 and 6. Under anhydrous conditions and with vigorous mechanical stirring, 6.7 ml (0.079 mol) of pyridine, 5.9 g (0.056 mol) of ethoxycarbonyl-hydrazide and 2.58 ml (0.03 mol) of phosphorous trichloride were successively added to a solution of 8.0 g (0.056 mol) of 5-methyl-1,2,4-oxidiazol-3-yl-acetic acid in a mixture of 50 ml of dioxane and 50 ml of toluene at room temperature. The resulting mixture was stirred at room temperature for 90 minutes and then was evaporated to dryness in vacuo. The residue was dissolved in 50 ml of iced water and the pH of the solution (0.8) was raised to 3.0, followed by continued extraction with dichloromethane for 16 hours. The resulting solution in dichloromethane was evaporated to dryness resulting in 13 g of a partially crystalline residue. The residue was triturated with n-hexane and was then collected by vacuum filtration. The slightly yellow crystalline product of 12.2 g was crystallized from a toluene-ethanol mixture cooled to 5° C. A first crop of pure product weighed 9.4 g (73.2% yield) and had a m.p. of 122°–123° C. The filtrate from the first crystallization was completely evaporated in vacuo and the residue was dissolved in a mixture of dichloromethane and diethyl ether. Upon cooling this solution to −30° C. a part of the product crystallized and the crystals were recovered by vacuum filtration at low temperature and were washed with cold diethyl ether to obtain 1.0 g (7.8% yield) of N'-(ethoxycarbonyl)-5-methyl-1,2,4-oxadiazol-3-yl-acethydrazide with a m.p. of 121.5°–123.5° C. for a total yield of 10.4 g (81% yield).

From its behavior on melting and from its IR and PMR spectra, it is deduced that the compound exists in at least two tautomeric forms.

IR spectra (values in cm⁻¹):

First crop: KBr-disc: 3320 and 3250 (equally intensive), 3065, 2985, 2945, 1738 and 1660 (equally extensive), ±1640 (sh), 1595, 1560, 1495, 1450 (sh), 1415, 1395, 1360, 1305, 1270 (sh), 1255;

Second crop: KBr-disc: 3310 (sh), 3210 (very intensive), 3060, 2985, 1760 (sh), 1735 and 1710, 1660 (sh), ±1630 (very intensive), 1590, 1560 (sh) 1500, 1475, 1445 (sh), 1418, 1395, 1360, 1340, 1300 (sh), 1280, 1255.

IR spectra of solutions in CHCl₃ were identical: 3400, about 3280 (broad), 1750, 1710, 1650 (sh), 1590, 1480, 1390, 1370, PMR spectra of the compound dissolved in d₆-DMSO (60 Mc, δ-values in ppm, DSS as internal reference also) showed the presence of tautomers: 1.18 (t, J=7.0 cps, 3H), 2.57 (s, 3H), 3.63 (somewhat broad s, 2H), about 4.05 (center of complicated absorption containing one major quartet (J=7.0 cps), 2H), about 9.0 (broad s, about 0.75H), about 9.3 (broad s, about 0.15H) and 9.8 (somewhat broad s, about 0.75H).

EXAMPLE 25

4-bromophenyl 3-methyl-1,2,4-oxadiazol-5-yl-acetate

Under anhydrous conditions, 6 g (0.042 mol) of 3-methyl-1,2,4-oxadiazol-5-yl-acetic acid, 7.3 g (0.043 mol) of 4-bromophenyl and 3.6 ml (0.042 mol) of pyridine were dissolved in a mixture of 25 ml of dioxane and 25 ml of toluene and after 2 ml (0.024 mol) of phosphorous trichloride were added, the stirred mixture became luke-warm. The mixture was stirred over night at room temperature and the supernatant liquid was decanted from the precipitate. The precipitate was twice washed with 10 ml portions of a 1:1 mixture of dioxane and toluene and the wash liquids were added to the decanted solution whereupon the solvent was completely evaporated in vacuo. The slightly moist crystalline residue weighed 12.3 g and was dissolved in 150 ml of diethyl ether. This solution was washed three times with a total of 75 ml of water and then was evaporated to dryness. The residue of 10.8 g was dissolved in a boiling mixture of diethyl ether and n-pentane whereupon the solution was gradually cooled down to −18° C. The precipitated crystals were collected by filtration, washed with a cold mixture of diethyl ether and pentane of about 1:1 and finally dried in vacuo to obtain 8.0 g (64.5% yield) of 4-bromophenyl 3-methyl-1,2,4-oxadiazol-5-yl-acetate melting at 73°–74° C.

IR (KBr-disc, values in cm⁻¹): 1745, 1585, 1480, 1440, 1400, 1370, 1335, 1290, 1210, 1180 (sh), 1165, 840, 770, 705, 680.

PMR: (CDCl₃, 60 Mc, δ-values in ppm, TMS as internal reference): 2.41 (s, 3H), 4.16 (s, 2H), about 6.85 to 7.65 (typical AA'BB' splitting pattern, 4H).

EXAMPLE 26

Sec.-butyl 3-methyl-1,2,4-oxadiazol-5-yl-acetate

Using the procedure of Example 17, 12 g of phosphorous oxychloride were slowly added to a mixture of 12 g of 3-methyl-1,2,4-oxadiazol-5-yl-acetic acid and 8.9 g of dry sec.-butanol and the rate of addition was adjusted to a reaction temperature of 65°±5° C. The resulting reaction mixture was stirred for 90 minutes at 65° C., and then treated as in Example 17. The product was distilled at 68° C. and 1.5 mm Hg to obtain 6.1 g (35% yield) of sec.-butyl 3-methyl-1,2,4-oxadiazol-5-yl-acetate. The purity of the final product was about 95% (according to TLC and PMR spectrum) and it had a refractive index $n_D^{25} = 1.438$.

IR: (NaCl windows, values in cm⁻¹): 3000, 2960, 2900, 1745, 1600. PMR: (60 Mc, CDCl₃, TMS, δ-values in ppm): 0.9 (triplet like, J=7.0 cps, 3H), 1.25 (d, J=6.3 cps, 3H), about 1.55 (quintet like, 2H), 2.40 (s, 3H), 3.93 (s, 2H), 4.93 (regular sextet, J=6.2 cps, 1H).

EXAMPLE 27

Benzyl 3-methyl-1,2,4-oxadiazol-5-yl-acetate

Using the procedure of Example 17, 8 g of phosphorous oxychloride were slowly added to a mixture of 8 g of 3-methyl-1,2,4-oxadiazol-5-yl-acetic acid and 6.2 g of dry benzyl alcohol with the rate of addition adjusted to a reaction temperature of 40°-45° C. The resulting reaction mixture was stirred for 5 hours at 40° C. and then was treated in the usual manner. The obtained yellow oil was submitted to column chromatography over silica employing as eluents n-hexane and 3:1 hexane-toluene-, 1:1-toluene-hexane, 3:1 toluene-hexane mixture, toluene and finally a 3:1 toluene-diethyl ether mixture. The finally obtained colorless oil was 6.1 g (47% yield) of benzyl 3-methyl-1,2,4-oxadiazol-5-yl-acetate with a purity of about 95% (according to TLC and PMR spectrum) and a refractive index $n_D^{25} = 1.518$.

IR (NaCl windows, values in cm⁻¹): 1745, 1590, 1500, 1395, 1355, 1200, 750, 700.

PMR (60 Mc, CDCl₃ TMS, δ-values in ppm): 2.35 (s, 3H), 3.93 (s, 2H), 5.17 (s, 2H), 4.3 (5H).

EXAMPLE 28

N-(2-chloro-phenyl)-3-methyl-1,2,4-oxadiazol-5-yl-acetamide

Using the procedure of Example 20, 1.65 ml of dry pyridine and 1.33 ml of 2-chloro-aniline were added successively to a solution of 2.0 g of 3-methyl-1,2,4-oxadiazol-5-yl-acetic acid in a mixture of 13 ml of dioxane and 13 ml of toluene and the precipitation of a viscous oil was observed. The reaction mixture was stirred for 90 minutes at room temperature and then was evaporated to dryness. The residue was thoroughly stirred with 10 ml of iced water, whereupon dichloromethane was added. The pH of the resulting, clear two-layer system was 0.8 and the pH was raised to 3.0 and the layers separated. The water layer was extracted 4 times with 25 ml volumes of dichloromethane and the 5 extracts were combined, washed once with a small volume of iced water, dried over anhydrous magnesium sulfate, filtered and evaporated. The residue was crystallized from carbon tetrachloride to obtain 2.7 g (77% yield) of pure N-(2-chloro-phenyl)-3-methyl-1,2,4-oxadiazol-5-yl-acetamide with a m.p. of 118.5°-119.5° C.

IR (KBr-disc, values in cm⁻¹): 3260, 1660, 1590, 1535, 1480, 1440, 1295, 890, 870, 750, 680. PMR: (60 Mc, CDCl₃, TMS, δ-values in ppm): 2.45 (s, 3H), 4.08 (s, 2H), about 6.85 to 7.5 (multiplet, 3H), 8.32 (q, J=7.5 cps and J'=2.2 cps 1H), about 9.6 (broad s, about 1H).

EXAMPLE 29

N-monosubstituted 3-substituted 1,2,4-oxadiazol-5-yl-acetamides and N-monosubstituted 5-substituted 1,2,4-oxadiazol-3-yl-acetamides As an illustration of the wide applicability of the reaction, details on reactions and the products are given for the following examples:
A. N-propyl-α-(3-ethyl-1,2,4-oxadiazol-5-yl)-propionamide
B. N-propen-3-yl-α-(3-ethyl-1,2,4-oxadiazol-5-yl)-propionamide
C. α-(3-ethyl-1,2,4-oxadiazol-5-yl)-propion-(-4-chloro)-anilide
D. N-(propen-3-yl)-3-benzyl-1,2,4-oxadiazol-5-yl-acetamide
E. 5-methyl-1,2,4-oxdiazol-3-yl-acet(-4-chloro)-anilide
F. 3-methoxymethyl-1,2,4-oxadiazol-5-yl-acet(-4-chloro)-anilide.

The reactions of isocyanates with the 1,2,4-oxadiazol-5-yl-acetic acids were performed at room temperature (about 20° C.) employing solvents like dichloromethane, toluene, chlorobenzene, 3,5-dimethyl-1,2,4-oxadiazole etc. The reactions with the 1,2,4-oxadiazol-3-yl-acetic acids are performed in much the same way, but are completed by heating the reaction mixture at about 60°-100° C. for about 15-30 minutes. Unless stated otherwise, all reactions were catalyzed by the presence of 2-5 mol % of N-vinyl-imidazole and the isocyanates used below were crude commercial samples. Therefore and for reasons like volatility of some isocyanates and occasional water traces in the employed 1,2,4-oxadiazol acetic acids, the isocyanates were employed in 10-20 mol % excess.

An extended description is given in Example A. For the other examples the starting products, the reaction medium, the approximate reaction time, some indications concerning purity and/or purification of the final products, melting points and IR- and/or PMR-spectra of the final products are indicated. The isolation procedures, involving the separation of the desired amides from the by-products of the reaction (in general only relatively small amounts of 1,3-disubstituted ureas and 1,2,4-oxadiazole-acetic acid) and the catalyst, were more or less similar to the isolation procedure given in Example A, but adapted to the individual case. Yields were obtained in the first experiment and yield figures therefore have no absolute value.

A. Employing anhydrous conditions, 17 mmol of about 90% pure α-(3-ethyl-1,2,4-oxadiazol-5-yl)-propionic acid (=3 ethyl-α-methyl-1,2,4-oxadiazol-5-yl-acetic acid) were dissolved in 40 ml of toluene and about 20.5 mmol of n-propyl-isocyanate and about 60 mg of the catalyst (a saturated solution of 4-methoxy-pyridine-1-oxide.1 H₂O in N-vinyl-imidazole) were added to the solution. While a slow stream of nitrogen was continuously passed over the surface, the reaction mixture was stirred for 5.5 hours at room temperature and the reaction mixture was evaporated in vacuo. The residue was dissolved in 100 ml of a 1:1 mixture of ethyl acetate and diethyl ether and this solution was extracted 4 times at pH 2.0 with 10 ml of water. The combined acid washings were extracted once with 10 ml of ethyl acetate and discarded. The two organic layers were combined and extracted 3 times at pH 7.0 with 10 ml of water. The combined washings were extracted once with 10 ml of ethyl acetate and discarded. The combined organic layers were treated with activated carbon, dried over anhydrous magnesium sulfate, filtered and completely evaporated in vacuo. The residue was stirred in 20 ml of n-hexane, whereupon diethyl ether was added slowly till the solid was almost completely dissolved. After filtration, the solution was gradually cooled to $-18°$ C. and the crystalline precipitate was collected by filtration, washed repeatedly with n-hexane and with very cold diethyl ether to obtain 1.7 g (about 50% yield) of N-propyl-$\alpha$-(3-ethyl-1,2,4-oxadiazol-5-yl)-propionamide with a purity of about 95% (according to TLC and PMR spectrum) and a m.p. of 52°–53° C.

PMR: (60 Mc, CDCl$_3$, TMS, $\delta$-values in ppm): 0.95 (triplet like, J$\approx$7.0 cps, 3H), complex 8H absorption area from 1.2 to 1.75 consisting of a CH$_3$-triplet at 1.35 (J'$\approx$7.5 cps, a partially hidden CH$_2$-multiplet and a CH$_3$-doublet at 1.67 (J''=7.2 cps), 2.78 (q, J'$\approx$7.5 cps, 2H), 3.2 1 quartet like, medium J$\approx$6.5 cps, 2H), 3.93 (q, J''=7.2 cps, 1H), about 6.8 (broad s, about 0.8H).

B. $\alpha$-(3-ethyl-1,2,4-oxadiazol-5-yl)-propionic acid (20 mmol of about 90% purity), allyl isocyanate (about 24 mmol), toluene, 3.5 hours, after column chromatography 2.7 g (64% yield) of pure product and a m.p. of 70°–71° C.

IR: (KB-disc, values in cm$^{-1}$): 3280, 3070, 2980, 2940, 1650, 1580, 1550, 1240, 990, 940, 890, 750, 685.

PMR: (60 Mc, CCl$_4$, TMS, $\delta$-values in ppm): 1.35 (t, J=7.5 cps, 3H), 1.61 (d, J'=7.2 cps, 3H), 2.72 (q, J=7.5 cps, 2H), about 3.65 to 4.1 (multiplet, 3H), about 4.9 to 5.35 (multiplet, 2H), about 5.5 to 6.2 (multiplet, 1H), about 7.1 (broad s, about 0.9H).

C. $\alpha$-(3-ethyl-1,2,4-oxadiazol-5-yl)-propionic acid (11.8 mmol of about 90% purity), 4-chloro-phenyl isocyanate (14 mmol), dichloromethane, about 50 mg of a saturated solution of 4-methoxy-pyridine-1-oxide.1-H$_2$O in N-vinyl-imidazole (catalyst), 4 hours, 1.85 g (about 60% yield) of an at least 95% pure product (according to TLC and PMR spectrum) with a m.p. of 130°–131° C. (after crystallization from benzene).

IR: (KBr-disc, values in cm$^{-1}$): 3260, 3190, 1675 (sh), 1655, 1585, 1540, 1490, 1400, 1250, 840, 765.

IR (chloroform, values in cm$^{-1}$): about 3400, about 3300, 1690, 1600, 1580, 1510–1550, 1495, 1395. (compound exhibits monomer-dimer feature).

PMR: (60 Mc, CDCl$_3$, TMS, $\delta$-values in ppm): 1.37 (t, J=7.5 cps, 3H), 1.74 (d, J=7.2 cps, 3H), 2.82 (q, J=7.5 cps, 2H), 4.07 (q, J=7.2 cps, 1H), 7.38 (center of AA'BB' splitting pattern, 4H), about 9.0 (broad s, about 0.9H).

D. 3-benzyl-1,2,4-oxadiazol-5-yl)-acetic acid (10 mmol), allyl isocyanate, toluene, 3.5 hours, 1.54 g (60% yield) of pure product crystallized from chloroform had a m.p. of 107.5°–108.5° C.

IR: (KBr-disc, values in cm$^{-1}$): 3290, 3100, 1655 and 1640 (sh), 1590, 1570, 1495, 1370, 1240, 1165, 1000, 735, 700.

PMR: (60 Mc, CDCl$_3$, TMS, $\delta$-values in ppm): 6H absorption area from about 3.75 to about 4.15 consisting of a CH$_2$ singlet at 3.83, a CH$_2$ singlet at 4.06 and a CH$_2$ multiplet, about 4.85 to about 5.35 (extended multiplet, 2H9, about 5.5 to 6.1 (extended multiplet, 1H), about 7.3 (C$_6$H$_5$) and about 7.1 (broad s) together about 5.8H.

E. 5-methyl-1,2,4-oxadiazol-3-yl-acetic acid (9.1 mmol), 4-chloro-phenyl isocyanate (11 mmol), chlorobenzene, about 40 mg of a saturated solution of 4-methoxy-pyridine-1-oxide.1H$_2$O in N-vinyl-imidazole, 4 hours at room temperature and 15 minutes at about 70° C., 1.56 g (60% yield) of almost pure product with a m.p. of 139°–141° C.

IR: (KBr-disc, values in cm$^{-1}$): 3255, 3195, 3130, 3075, 2950, 1660, 1610, 1590, 1545, 1495, 1450, 1400, 1260, 975, 895, 840, 760, 710, 690.

PMR: (60 Mc, CDCl$_3$, TMS, $\delta$-values in ppm): 2.66 (s, 3H), 3.85 (s, 2H), 7.35 (center of AA'BB' splitting pattern, 4H), about 8.6 (broad s, about 0.8H).

F. 3-methoxymethyl-1,2,4-oxadiazol-5-yl-acetic acid (6.5 mmol), 4-chloro-phenyl isocyanate (7.5 mmol), 3.5 hours, 1.4 g of almost pure product. After crystallization from toluene 1.15 g (63% yield) with a m.p. of 114.5°–115.5° C.

PMR: (60 Mc, CDCl$_3$, TMS, $\delta$-values in ppm): 3.49 (s, 3H), 4.06 (s, 2H), 4.61 (s, 2H), 7.35 (center of AA'BB' splitting pattern, 4H), about 8.95 (broad s, about 0.8H).

EXAMPLE 30

N,N'-bis (propen-3-yl)-1,2,4-oxadiazol-3,5-yl-bisacetamide 40 mg of N-vinyl-imidazole were added to a solution of 2 g of almost pure 1,2,4-oxadiazol-3,5-yl-bis acetic acid (10.7 mmol) in 15 ml of 3,5-dimethyl-1,2,4-oxadiazole, followed by the dropwise but fast introduction of a solution of about 12 mmol of allyl isocyanate in 10 ml of toluene. Under anhydrous conditions, the reaction mixture was stirred for 2 hours at room temperature and since a thin-layer chromatogram indicated only partial conversion of the starting product into three compounds, principally the bisamide, another solution of allyl isocyanate (about 10.5 mmol) in about 10 ml of toluene was added. After 4 hours additional stirring, the reaction mixture was mixed with 40 ml of iced water and the pH was brought to 7.0. A solid precipitate (which appeared to be a mixture of mainly bisamide and a minor amount of 1,3-bisallyl-urea) was collected by vacuum filtration. The two layers of the filtrate were separated and the organic layer was discarded. The remaining water-layer containing the urea-derivative, the not converted starting product and its three reaction products, was acidified to pH 2.0 and then extracted 15 times with 20 ml volumes of ethyl acetate resulting in complete extraction of the urea and the bisamide, but in only partial extraction of the two other reaction products. The precipitate was added to the combined extracts and the resulting solution was completely evaporated in vacuo. The residue was subjected to column chromatography over silica employing as eluents diethyl ether, mixtures of diethyl ether with increasing amounts of a 5:4 mixture of ethyl acetate and acetone and this mixture containing very small but increasing amounts of formic acid. A satisfactory separation of the urea and the bisamide was achieved, but separation of the bisamide from the 2 acidic monoamides (in order of elution N-(propen-3-yl)-1,2,4-oxadiazol-5-yl-acetamide-3-yl-acetic-acid and N-(propen-3-yl)-1,2,4-oxadiazol-3-yl-acetamide-5-yl-acetic acid) was somewhat less efficient.

1.3 g (48%) of the bisamide N,N'-bis (propen-3-yl)-1,2,4-oxadiazol-3,5-yl-bisacetamide in substantially pure state after crystallization from ethyl acetate and melting at 170°–172° C., and 0.34 g (14%) of N-(propen-3-yl)-1,2,4-oxadiazol-5-yl-acetamide-3-yl-acetic acid melting at 97°–98° C. were obtained.

IR bisamide (KBr-disc, values in cm$^{-1}$): 3300, 3185, 2930, 1645, 1590, 1565, 1415, 1380, 1245, 990, 935, 755, 710

PMR bisamide (60 Mc, d$_6$-DMSO, DSS, δ-values in ppm): 8H absorption area from about 3.5 to 4.05 consisting of a CH$_2$-singlet at 3.67, a CH$_2$-singlet at 3.95 and a multiplet (two N—CH$_2$ groups), about 4.9 to 5.4 (extended multiplet, 4H), about 5.5 to 6.2 (extended multiplet, 2H), about 8.4 (about 1.8H)

PMR by-product (ibidem): 6H absorption area from about 3.6 to 4.1 consisting of a CH$_2$-singlet at 3.61, a CH$_2$-singlet at 3.97 and a CH$_2$-multiplet, about 4.95 to 5.4 (multiplet, 2H), about 5.55 to 6.25 (multiplet, 1H), about 8.5 (about 0.8H)

In an analogous way 3-α-(4-fluorophenycarbamyl)-benzyl-1,2,4-oxadiazol-5-yl-acet(-4-fluoro)-anilide was prepared starting from 3-(α-carboxy)-benzyl-1,2,4-oxadiazol-5-yl-acetic acid and 2 equivalents of 4-fluorophenyl isocyanate in 45% yield (crystallized with approximately 1 mole of water). The product had a m.p. of 85°–87° C. (subl.)

IR: (KBr-disc, values in cm$^{-1}$): 3400–3500, about 3200–3300, 3150, 3075, 1670, 1620–1640, 1585, 1560, 1550 (sh), 1510, 1415, 1235 (sh), 1225, 1165, 845.

PMR: (about 7:1 mixture of CDCl$_3$ and d$_6$-DMSO, 60 Mc, TMS, δ-values in ppm): 4.06 (s, 2H), 5.35 (s, 1H), 6.95 (center of sextet-like absorption, apparent J-values of 8.5 and 1.3 cps, 4H), from about 7.2 to 7.7 (multiplets, 9H), 9.85 (broadened singlet) and 10.05 (ibidem) together about 1.6H, and 1,2,4-oxadiazol-3,5-diyl-bis acet(-4-chloro)-anilide was prepared starting from 1.5 g (8 mmol) of 1,2,4-oxadiazol-3,5-diyl-bisacetic acid and about 14 mmol of 4-chloro-phenyl isocyanate to obtain 1.1 g (35% yield) of the bisanilide and 0.8 g (34%) of 1,2,4-oxadiazol-3-yl-acetic acid-5-yl-(-4-chloro)-acetanilide. The bisanilide melted with decomposition at 240°–247° C. (decolorization at 220° C.) and the second product melted at 182°–184° C. 1,2,4-oxadiazol-3,5-diyl-bis acet(-4-chloro)-anilide:

IR: (KBr-disc, values in cm$^{-1}$): 3280, 3130, 3065, 1670, 1600, 1550, 1500, 1415, 1390, 1355, 1325, 1295, 1265, 1235, 1190, 1110, 905, 855, 830, 770, 720, 700.

PMR: (d$_6$-DMSO, 60 Mc, DSS, δ-values in ppm): 3.95 (s, 2H), 4.23(S,2H), about 7.5 (center of typical AA'BB' splitting pattern, 8H), 10.5 (slightly broad s) and 10.6 (ibidem) together about 1.8H.

1,2,4-oxadiazol-3-yl-acetic acid-5-yl-(-4-chloro)-acetanilide:

IR (KBr-disc, values in cm$^{-1}$): ±3500, ±2550, ±2650, 3265, 3120, 3040, 2950, 1710, 1665, 1595, 1540, 1500, 1435, 1405, 1380, 1250, 1195, 1100, 850, 755.

PMR (d$_6$-DMSO, 60 Mc, DSS, δ-values in ppm): 3.83 (s, 2H), 4.22 (s, 2H), about 7.5 (center of AA'BB' splitting pattern, 4H), 10.6 (slightly broad s, about 0.9H).

EXAMPLE 31

7-[5-(N-propen-3-yl)-carbamoylmethyl-1,2,4-oxadiazol-3-yl-acetamido]-cephalosporanic acid 0.3 ml (2.18 mmol) of triethylamine were added to a suspension of 390 mg (1.45 mmol) of 7-amino-cephalosporanic acid in 8 ml of dry dichloromethane. Employing anhydrous conditions, the mixture was stirred for about 5 minutes, whereupon 0.067 ml (0.77 mmol) of PCl$_3$ were added and the resulting suspension was stirred for about 5 minutes, followed by the introduction of 327 mg (1.5 mmol) of 5-(N-propen-3-yl)-carbamoylmethyl-1,2,4-oxadiazol-3-yl-acetic acid suspended in 4 ml of dichloromethane. The resulting yellow reaction mixture was stirred at room temperature for 16 hours and then was poured into 19 ml of iced water while a dilute sodium hydroxide solution was simultaneously added. The layers were separated at pH 6.5 and the organic layer was discarded. The water-layer was extracted at pH 6.5, 5.0 and 4.0 with 25 ml volumes of ethyl acetate. These extracts were discarded and the remaining water-layer was further extracted at pH 3.8, 2.5 and 1.5 with 25 ml volumes of ethyl acetate. These extracts were combined, washed with a small volume of iced water, dried over anhydrous magnesium sulfate, filtered and concentrated in vacuo to about 10 ml which caused precipitation of 7-[5-(N-propen-3-yl)-carbamoylmethyl-1,2,4-oxadiazol-3-yl-acetamido]-cephalosporanic acid in almost pure state in a yield of 250 mg.

IR (KBr-disc, values in cm$^{-1}$): ±3550, ±2600, 3290, 3090, 3050, 2950, 1780, 1740, 1720, 1660, 1585, 1545, 1420, 1385, 1355, 1240.

PMR (60 Mc, about 4:1 mixture of d$_6$-DMSO and DCO$_2$D, DSS, δ-values in ppm): 2.06 (s, 3H), 8H absorption area from about 3.45 to about 4.15 consisting of the S—CH$_2$ absorption at about 3.6, a CH$_2$-singlet at 3.84, a CH$_2$-singlet at 3.97 and a N—CH$_2$-multiplet; a 5H absorption area from about 4.6 to 5.4, consisting of a AB-quartet at 4.63, 4.85, 4.97 and 5.20 (J$_{AB}$≈12.8 cps), a doublet at 5.12 (J=4.8 cps) and a CH$_2$-multiplet; a 2H absorption area from 5.55 to 6.1 consisting of a multiplet and a doublet at 5.76 (J=4.8 cps). The spectrum in d$_6$-DMSO alone showed a triplet like NH absorption at 8.45 and a NH doublet (J=8.0 cps) at 9.25.

EXAMPLE 32

7-[5-benzyl-1,2,4-oxadiazol-3-yl-acetamido]-cephalosporanic acid

Using the process of Example 13, 1048 mg (4 mmol) of 5-benzyl-1,2,4-oxadiazol-3-yl-acetic acid was converted into its acid chloride using 12 ml of dry carbon tetrachloride, 0.4 ml of thionyl chloride and 2 drops of dimethylformamide. The solution was gently refluxed for 15 minutes whereupon carbon tetrachloride was removed in vacuo and the colored residue was dissolved in 5 ml of dry ethyl acetate. At the same time, a suspension of 1.088 g (4 mmol) of 7-aminocephalosporanic acid in 25 ml of dry ethyl acetate was reacted with 1.14 ml (8 mmol) of triethylamine and 1.04 ml of trimethylchlorosilane (8 mmol). After 30 minutes stirring at room temperature, 0.47 ml (4 mmol) of quinoline and the solution of the acid chloride were added dropwise. The reaction mixture was stirred for 30 minutes and subsequently treated as usual. In the isolation procedure, the desired compound was obtained by extraction with ethyl acetate at pH values decreasing from 6.0 to 4.5 to obtain 1.35 g (70% yield) of practically pure 7-[5-benzyl-1,2,4-oxadiazol-3-yl-acetamido]-cephalosporanic acid.

IR (KBr-disc, values in cm$^{-1}$): 3275, 3075, 2975, ±3550 and ±2600, 1790, 1735, ±1700 (sh), 1675, 1640 (sh), 1580, 1555, 1420, 1390, 1285, 1250, 1220, 750, 715.

PMR (60 Mc, d$_6$-DMSO, DSS, δ-values in cm$^{-1}$): 2.06 (s, 3H), ±3.4 (broadened s, 2H), 3.79 (s, 2H), 4.34 (s, 2H), 4.60 to 5.17 (AB$_q$, J=12.4 cps) and ±5.1 (d, J=4.8 cps) together 3H, ±5.7 (q, J=4.8 and J'≈8.2 cps, 1H), 7.35 (5H), ±9.2 (d, J'≈8.2 cps, about 0.8H).

EXAMPLE 33

The method described in Example 23 using the amine, the 1,2,4-oxadiazole acetic acid and phosphorous trichloride in a 2.5:1:0.58 molar ratio was found to be of wide applicability in the preparation of amides in the case of secondary amines and primary amines. This method is particularly adaptable to amines of somewhat tricky nature, for instance to those of which the preparation of isocyanates is difficult (e.g. 4-amino-pyridine, 2-amino-thiazole). The reaction conditions in the following examples were the same as in Example 23, but the isolation procedures were adapted to the individual cases. It was found that 60 minutes heating of the solution of the residue of the reaction in acid water, as in Example 23, is not necessary in general and should be omitted when delicate amides are involved. The examples given below are by no means exhaustive nor are the indicated yields decisive, since they were obtained in the first experiments.

A. 76% yield of N-(thiazol-2-yl)-3-ethyl-1,2,4-oxadiazol-5-yl-acetamide m.p.: 170.5°–171.5° C. (subl.). Isolated by extraction with ethyl acetate and crystallization from ethyl acetate.

IR (KBr-disc, values in cm$^{-1}$): 3300, 3200, 3090, 2980, 2940, ±2880, ±2760, 1680, 1600 (very intensive), ±1570 (sh), ±1550 (sh), ±1530 sh), 1420, 1385 (sh), 1370, 1350, 1300, 1280, 1260, 1200, 1180, 1160, 965, 890, ±830, 790, 750.

PMR (about 6:1 mixture of CDCl$_3$ and d$_6$-DMSO, 60 Mc, TMS, δ-values in ppm): 1.3 (t, J=7.5 cps, 3H), 2.75 (q, J=7.5 cps, 2H), 4.2 (s, 2H), ±6.9 (d, J=3.5 cps, 1H), 7.4 (d, J=3.5 cps, 1H), below 9 (very broad, about 1H).

B. 40% yield of N-(4-pyridyl)-3-methyl-1,2,4-oxadiazol-5-yl-acetamide hydrochloride m.p.: 211°–212° C. (d). Purification of solution in water by washing with dichloromethane at pH 2.0. Extracted from water by dichloromethane at pH 6.0. Since the free base did not solidify easily, the residue was dissolved in acetone, followed by addition of 4 N HCl. The isolated HCl salt was pure, but slightly wet.

IR (KBr-disc, values in cm$^{-1}$): ±3220, ±3100 (sh), ±3020 (sh), ±2950 to 2500, 1720, 1630, 1595, 1535, 1500 (sh), 1420, 1400, 1380, 1355, 1335, 1310, 1280, 1200, 1165, 840.

PMR (d$_6$-DMSO, 60 Mc, DSS, δ-values in ppm): 2.38 (s, 3H), 4.48 (s, 2H), 8.1 to 8.85 (AA'BB' splitting pattern, 4H), 12.6 (NH, slightly broad s, about 0.9H).

C. 58% yield of N-methyl-N-phenyl-3-ethyl-1,2,4-oxadiazol-5-yl-acetamide m.p.: 53° C. Since the obtained crude product did not solidify easily, it was submitted to column chromatography over silica employing as eluents n-hexane, n-hexane-toluene mixtures, toluene and finally a 3:1 mixture of toluene and diethyl ether. The compound was subsequently crystallized from toluene-heptane.

IR (KBr-disc, values in cm$^{-1}$): 3000, 2950, 1660, 1505, 1420, 1400, 1375, 1315, 1270, 1180, 1135, 785, 720.

PMR (CDCl$_3$, 60 Mc, TMS, δ-values in ppm): 1.21 (t, J=7.5 cps, 3H), 2.73 (q, J=7.5 cps, 2H), 3.33 (s, 3H), 3.76 (s, 2H), 7.1 to 7.6 (multiplet, 5H).

D. 66% yield of N,N-di(n)-butyl-3-methyl-1,2,4-oxadiazol-5-yl-acetamide oil. Almost pure, crude product (over 80% yield) purified by column chromatography over silica in the same way as described under C.

IR (NaCl windows, values in cm$^{-1}$): 2965, 2885, 1655, 1595, 1440–1480, 1400, 1360, 1305, 1230, 745.

PMR (CDCl$_3$, 60 Mc, δ-values in ppm, TMS): from about 0.7 to about 1.9 (complex splitting pattern, 14H), 2.37 (s, 3H), about 3.1 to 3.5 (multiplet, 4H), 3.96 (s, 2H).

EXAMPLE 34

7-[5-ethyl-1,2,4-oxadiazol-3-yl-acetamido]-cephalosporanic acid

Employing anhydrous conditions, a mixture of 3.1 g (20 mmol) of 5-ethyl-1,2,4-oxadiazol-3-yl-acetic acid, 2.2 ml of thionyl chloride, 2 microdrops of dimethylformamide and 60 ml of carbon tetrachloride was gently refluxed for about 20 minutes and according to an IR spectrum, complete conversion of the carboxylic acid into its acid chloride was effected. The resulting solution was evaporated in vacuo and the residue was dissolved in 20 ml of ethyl acetate. In the mean time, 5.6 ml of triethylamine were added at 10° C. to a suspension of 5.44 g (20 mmol) of crude 7-aminocephalosporanic acid in 50 ml of ethyl acetate, followed by the addition of 5.1 ml of trimethylchlorosilane. The mixture was stirred for 60 minutes at room temperature and then 2.36 ml of quinoline and the solution of the acid chloride were added dropwise. The reaction mixture was stirred for 30 minutes at room temperature and the contents of the flask were poured into 75 ml of iced water. The pH was brought to 7.0, the layers were separated and the organic layer was discarded. The desired compound was removed from the water-layer by a number of extractions with 100 ml volumes of ethyl acetate at pH values gradually lowered from pH 5.0 to 2.0. The combined extracts were washed twice with small volumes of iced water, once at pH 1.0 and once at pH 2.0. The extract was treated with activated carbon, dried over anhydrous magnesium sulfate, filtered and concentrated in vacuo to approximately 25 ml. The resulting crystalline precipitate was vacuum filtered, washed with dry ethyl acetate and carbon tetrachloride, and dried to constant weight to obtain 5.9 g (about 70% yield) of 7-[5-ethyl-1,2,4-oxadiazol-3-yl-acetamido]-cephalosporanic acid of 90–95% purity.

The combined filtrates were evaporated in vacuo resulting in 1.3 g of a slightly yellow material, which was purified by repeated trituration with diethyl ether resulting in 0.65 g of additional product. According to thin-layer chromatograms and an IR spectrum, this second crop was of about the same purity.

IR (KBr-disc, values in cm$^{-1}$): ±3550 and ±2600, 3290, 3060, 2995, 2955, 1790, 1750, 1725, 1670, 1645 (sh), 1580, 1555, 1420, 1385, 1230, 1210 (sh), 750, 720.

PMR (d$_6$-DMSO, 60 Mc, δ-values in ppm, DSS): 1.30 (t, J=7.5 cps, 3H), 2.05 (s, 3H), 2.95 (q, J=7.5 cps, 2H), 3.6 (broadened s, 2H), 3.77 (s, 2H), 4.60 to about 5.25 (AB-q, J=12.8 cps) and about 5.15 (d, J=4.8 cps) together 3H, about 5.25 (q, J=4.8 cps and J'=8.0 cps, 1H), 9.2 (d, J'=8.0 cps, about 0.8H).

By a common procedure, a solution of 5.7 g of the first crop in 250 ml of acetone was treated with a solution of an equivalent amount of sodium α-ethyl-caproate, dissolved in 12.5 ml of ethyl acetate to obtain 5.3 g of the slightly more pure sodium salt of the said cephalosporin.

PMR (about 5:2 mixture of CDCl$_3$ and d$_6$-DMSO, 60 Mc, TMS, δ-values in ppm): 3.65 (s, 3H), 3.95 (s, 2H), about 7.1 (asymmetric, broadened s, about 3H). Possibly as consequence of the presence of a slight amount of water present in the compound and/or in d$_6$-DMSO, the rather acidic C$_5$—C$_\alpha$—H is not seen separately, but is presumably exchanged so that its signal appears together with the COOH signals at low field. Additional chemical proof of its structure was obtained by conversion of the bisacetic acid to its bis-acet (4-fluoro) anilide.

EXAMPLE 40

3-hydroxymethyl-1,2,4-oxadiazol-5-yl-acetic acid

Under anhydrous conditions, a solution of approximately 1.2 mol of n-butyl lithium in n-hexane was added dropwise over 3 hours to an efficiently cooled solution of 66 g (0.58 mol) of 3-hydroxymethyl-5-methyl-1,2,4-oxadiazol and 87 ml of N,N,N',N'-tetramethyl ethylene diamine in 1200 ml of tetrahydrofuran and during the addition, the reaction temperature was not allowed to rise above −70° C. The reaction mixture was stirred for 1 hour at −70° C. and under efficient cooling, dried gaseous carbon dioxide was passed over the surface of the stirred reaction mixture for ten hours at −70° C. Subsequently, the temperature was allowed to rise gradually to −5° C. and the formed precipitate was collected by vacuum filtration and was washed with dry ethyl acetate and with n-hexane. The precipitate was dissolved slowly by adding it in small portions to a stirred icy-cold mixture of 500 ml of water and 500 ml of diethyl ether and concentrated phosphoric acid was added till the pH was 4.0. The layers were separated and the organic layer discarded. The water-layer was further acidified to a pH of 2.0 and subsequently evaporated in vacuo. Remnants of water in the residue were removed in vacuo with the help of benzene and the residue was dried in vacuo over phosphorous pentoxide for 16 hours. The syrupy product was stirred with 500 ml of acetone at about 35° C. and the acetone was decanted. This was repeated once whereupon the residue became a solid mass which was transferred to a filter and repeatedly stirred with 500 ml portions of acetone until according to thin-layer chromatograms the filtrate no longer contained the desired compound. All filtrates were combined (total of about 4000 ml) and concentrated in vacuo to a volume of about 300 ml. 600 ml of ethyl acetate were added and the resulting solution was again concentrated in vacuo to a final volume of about 250 ml. The resulting crystalline precipitate was vacuum filtered, washed with dry ethyl acetate and with carbon tetrachloride. After drying in vacuo, 41 g of 3-hydroxymethyl-1,2,4-oxadiazol-5-yl-acetic acid were obtained with melting and decomposition taking place between about 96° and 98° C. The filtrate was evaporated in vacuo and the oily residue was repeatedly stirred with small volumes of dichloromethane. The resulting solid was transferred to a filter and washed with ethyl acetate and carbon tetrachloride. After drying, the second crop of said product weighed 14.1 g and melted with extensive decomposition at 92°–96° C. According to thin-layer chromatograms, IR and PMR spectra both crops were virtually identical for a total of 45.1 g (about 55% yield) of about 96% purity.

IR (KBr-disc, values in cm$^{-1}$): 3440, 1745, 1720, 1600, 1430, 1390, 1320, 1240, 1220 (sh), 1180, 1070, 1040, 780, 735, 650.

PMR (about 6:1 mixture of CDCl$_3$ and d$_6$-DMSO, 60 Mc, TMS, δ-values in ppm): 3.95 (s, 2H), 4.66 (s, 2H), about 7.5 (broadened s, about 2H).

EXAMPLE 41

Sodium 7-[5-ethyl-1,2,4-oxadiazol-3-yl-acetamido]-3-[5-methyl-1,3,4-thiadiazol-2-yl-mercaptomethyl]-3-cephem-4-carboxylate The reaction conditions were very much the same as in Example 34 and starting from 1.55 g (10 mmol) of 5-ethyl-1,2,4-oxadiazol-3-yl-acetic acid and 3.44 g (10 mmol) of 7-amino-3-(5-methyl-1,3,4-thiadiazol-2-yl-mercaptomethyl)-3-cephem-4-carboxylic acid of about 92% purity, 2.58 g of the nearly pure sodium 7-[5-ethyl-1,2,4-oxadiazol-3-yl-acetamido]-3-[5-methyl-1,3,4-thiadiazol-2-yl-mercaptomethyl]-3-cephem-4-carboxylate were obtained. In the isolation procedure the compound was removed from water by a number of extractions with ethyl acetate between pH 5.0 and pH 3.5. The combined extracts were washed with water of pH 1.0 and 2.5, decolorized with activated carbon and completely evaporated in vacuo. The residue weighed 3.2 g (about 65%) and was dissolved in a mixture of 65 ml of acetone and 250 ml of ethanol. A concentrated solution of 6 mmol of sodium α-ethyl-caproate in ethyl acetate was added and the resulting solution was concentrated in vacuo to a volume of 50 ml. To the well stirred solution, 100 ml of diethyl ether were slowly added and the formed precipitate was collected by filtration, washed with ether and dried in vacuo to obtain sodium 7-[5-ethyl-1,2,4-oxadiazol-3-yl-acetamido]-3-[5-methyl-1,3,4-thiadiazol-2-yl-mercaptomethyl]-3-cephem-4-carboxylate.

IR (KBr-disc, values in cm$^{-1}$): ±3450, 3280, 3050, 2985, 2940, 1765, 1680, 1610, 1580, 1550, 1415, (sh), 1390, 1370.

PMR (d$_6$-DMSO, 60 Mc, DSS, δ-values in ppm): 1.28 (t, J=7.5 cps, 3H), 2.69 (s) and 2.93 (q, J=7.5 cps) together 5H, about 3.6 (2H), 3.77 (s, 2H), from about 4.25 to 4.7 (AB-q, J≈13 cps, 2H), 5.0 (d, J≈4.9 cps. 1H), 5.55 (q, J≈4.9 cps. J'≈8.2 cps, 1H), 9.2 (d, J'≈8.2 cps, about 1H).

Using the same procedure, 0.994 g (7 mmol) of 5-methyl-1,2,4-oxadiazol-3-yl-acetic acid and 1.904 g (7 mmol) of 7-amino-3-(1-methyl-tetrazol-5-yl-mercaptomethyl)-3-cephem-4-carboxylic acid (90% purity) were reacted to obtain 1.85 g (55% yield) of nearly pure 7-[5-methyl-1,2,4-oxadiazol-3-yl-acetamido]-3-[1-methyl-tetrazol-5-yl-mercaptomethyl]-3-cephem-4-carboxylic acid from which the sodium salt was prepared. In this case the ACA-derivative was not dissolved by treatment with triethylamine and trimethylchlorosilane, but by means of addition of 14 mmol of N,O-bistrimethylsilylacetamide.

IR (ibidem): ±3400(H$_2$O), 3200–3300, 1760, 1680, 1600, 1580, ±1540, ±1400(sh), 1380, 1355

PMR (ibidem): 2.58(s, 3H), about 3.45 (2H), 3.75 (s, 2H), 3.95 (s, 3H), from about 4.15 to 4.65 (AB-q, J≈13.5 cps, 2H), 5.0 (d, J≈4.8 cps, 1H), 5.55 (q, J≈4.8 cps, J'≈8.2 cps, 1H), 9.2 (d, J'≈8.2 cps, about 1H)

PHARMACOLOGICAL STUDY

Some of the penicillins and cephalosporins were tested for antibiotic activity in vitro by means of an agar serial dilution test and/or in some cases by means of a micro serial dilution test, which are respectively carried out as follows:

A. Agar serial dilution test

A stock solution of the compound at 2,000 μg/ml was prepared in a sterile suitable vehicle and two-fold dilutions were made with sterile 1/20 mol phosphate buffer pH 6.5 ($KH_2PO_4$-NaOH). 1 ml quantities of each dilution were incorporated in 19 ml brain-heart infusion agar in sterile Petri dishes and the hardened surface was inoculated with test organisms and incubated for 24 hours at 37° C.

B. Micro serial dilution test

Two drops of a stock solution of the test compound (antibiotic) in a known concentration were brought into the first hole of a test plate with 9 numbered holes with a sterile Pasteur pipette. After rinsing this pipette three times with a physiological NaCl-solution, two drops of a stock solution of the test organism in a culture medium were brought in all the holes except for hole 8. In the first hole, the solution of the tested compound had been half diluted, then by stirring the liquid in the first hole and adding two drops of this mixture to the second hole and so on until hole 8, dilutions of the test compound solution were obtained in geometrical progression. The hole 9 contained no antibiotic and served for checking the growth of the testogranism in a blank medium. The test plate was incubated at 30° C. or 37° C. for about 18 hours.

The minimal inhibitory concentration (MIC) of the test compound, which is the least amount of antibiotic that completely inhibited the growth of the test organism, was expressed in μg/ml in both cases and the MIC values of the test compounds and of Benzylpenicillin, Phenoxymethylpenicillin, Ampicillin, Cephalexin, Cephalotin, Benzylcephalosporin, Benzyldesacetoxycephalosporin as references, are shown in the following tables. The MIC values, determined by the micro serial dilution test have been placed between brackets.

Compound A—6-[(3-methoxymethyl-1,2,4-oxadiazol-5-yl)-acetamido]-penicillanic acid, Compound B—7-[α-phenyl-(3-methyl-1,2,4-oxadiazol-5-yl)-acetamido]-3-acetoxymethyl-3-cephem-4-carboxylic acid Compound C—7-[(5-benzyl-1,2,4-oxadiazol-3-yl)-acetamido]-3-acetoxymethyl-3-cephem-4-carboxylic acid Compound D—sodium-7-[(3-methyl-1,2,4-oxadiazol-5-yl)-acetamido]-3-acetoxymethyl-3-cephem-4-carboxylate Compound E—7-[α-morpholino(3-methyl-1,2,4-oxadiazol-5-yl)-acetamido]-3-acetoxymethyl-3-cephem-4-carboxylic acid Compound F—disodium 7-[(3-carboxymethyl-1,2,4-oxadiazol-5-yl)-acetamido]-3[1-methyl-tetrazol-5-yl-mercaptomethyl] 3-cephem-4-carboxylate.

Compound G—sodium-7[(3-methyl-1,2,4-oxadiazol-5-yl)-acetamido] 3 [1-methyl-tetrazol-5-yl-mercaptomethyl] 3-cephem-4-carboxylate.

| test compound→ | benzyldesacetoxy ceph. (K-salt) | Cefalexin (acid) | Penicillin G | Penicillin V | Ampicillin | Cephalosporin G (K-salt) | Cephalotin (acid) | Cephazolin (Na-salt) |
|---|---|---|---|---|---|---|---|---|
| Bac.Subt.ATCC 6633 | 0.5 | 0.5 | (0.006) | (0.002) | 0.03 | 0.09 | 0.12 | 0.25 |
| Staph.aureus A 321 | 1 | 1.5 | (0.03) | (0.045) | 0.12 | 1.5 | 0.5 | 0.25 |
| A355¹ | 25 | 12.5 | (10) | (25) | 6 | 1.5 (1.8) | 0.5 | 1.5 (0.6) |
| A2000 | 12.5 | 12.5 | — | — | 1.5 | 1.5 | 0.5 | 0.75(0.9) |
| A2001 | — | — | — | — | 1 | (0.9) | — | 0.5(0.45) |
| Strep.haem. A 266 | 1 | 0.25 | (0.013) | (0.2) | <0.015 | 0.03 | 0.06 | |
| Strep. faec. L 80 | >100 | 100 | (4) | (5) | 1.0 | 25 | 25 | 12.5 |
| Dipl.pneum. L 54 | 3 | 3 | (0.13) | (1) | 0.06 | 0.06 | 0.5 | 0.25 |
| Haem.infl. A 1030 | (>125) | (125) | (0.5) | (1.0) | <125(0.5) | (125) | — | |
| Pruc.melit. A 488 | 100 | 6 | (0.25) | (1) | 1.0 | 2 | 6 | |
| Past.Multo. A 723 | 25 | 3 | (0.2) | (0.75) | 0.25 | 1 | 0.7 | 1.5 |
| Kleb.pneum. A 809 | 100 | 3 | (100) | (100) | 25 | 1 | 0.7 (0.37) | 1.5 |
| Salm.dubl. P 43 | >100 | 6 | (5) | (>100) | 1.5 | 6 | 1.5 | 1.5 |
| Salm.typh. R 127 | — | (6) | — | — | — | — | (3) | 3 |
| Esch.coli U 20 | >100 | 12.5 | (40) | (100) | 3 | 50 | 3 | 1.5 |
| Shig.Equir. T 3 | 100 | 1.5 | (0.25) | (5) | 1.0 | 25 | 1.5 | |
| Pseud.aerug. H 10 | >100 | >100 | (>100) | (>100) | 125 | >100 | >100 | >100 |
| 2396 | >100 | >100 | (>100) | (®100) | 12.5 | >100 | >100 | >100 |
| Wyeth A 1058 | >100 | >100 | (100) | (>100) | >100 | >100 | >100 | >100 |
| Prot.rettg. A 821 | >100 | 12.5 | (25) | (100) | 3 | 25 | 12.5 | (1.2) |
| Prot.mirab. H 3 | >100 | 25 | (7.5) | (100) | 0.9 | 25 | 12.5 | 6 |
| L 93 | 50 | 12.5 | (0.5) | (10) | 0.15 | 2 | 0.6 | 1.5 |
| A1200 | — | — | — | — | — | — | — | 6 |
| Prot.morg. 2241 | >100 | >100 | (>100) | (>100) | 12.5 | >100 | >100 | 25 |

| test compound→ | Compound A | Compound B | Compound C | Compound D | Compound E | Example 6 | Example 7 | Example 9 | Example 10 | Example 11A | Example 11B |
|---|---|---|---|---|---|---|---|---|---|---|---|
| Bac.Subt.ATCC 6633 | 0.06 | 0.25 | 0.25 | 0.12 | 6 | 0.03 | 3 | 0.06 | 0.25 | 0.06 | 0.03 |
| Staph.aureus A 321 | 0.5 | 0.5 | 0.25 | 0.5 | 6 | 0.25 | 3 | 0.12 | 0.25 | 0.06 | 0.12 |
| A 355¹ | 6(60) | 1.5(1.2) | 0.75(0.6) | 0.5(0.6) | 12.5(8) | 25(125) | 100(8) | 1(0.15) | 1(0.6) | 3 | 50(>12) |
| A 2000 | 6(90) | 1.5(1.2) | 0.25(0.3) | 0.75(1.0) | 12.5(8) | 1.5(23) | 25(4) | 1 | 1(0.9) | 3 | 50(>12) |
| A 2001 | 1.5(3.7) | 1.5(1.2) | 0.25(0.6) | 0.75(0.6) | 12.5(4) | 1(2.5) | 6(5) | (0.11) | 1(0.3) | — | 3(2.5) |
| Strep.haem. A 266 | 0.03 | 0.5 | 0.5 | — | — | — | 25 | 0.03 | 0.03 | 1.0 | 0.03 |
| Strep.faem. L 80 | 6 | 50 | 12.5 | 50 | >100 | 1.0 | 100 | 6 | 50 | 25 | 6 |
| Dipl.pneum. L 54 | 0.25 | 1 | 0.5 | 0.75 | 12.5 | 0.06 | 4 | 0.25 | — | 3 | 0.25 |
| Haem.infl. A 1030 | (4) | (1.2) | (125) | (30) | (>125) | (1.2) | (30) | (125) | (125) | 100 | (125) |
| Bruc.melit. A 488 | 0.5 | 1.5 | — | — | — | 1 | 25 | 100 | 6 | 3 | — |
| Past.multo. A 723 | 1 | 0.5 | 1 | 1.5 | 6 | 1 | 25 | 50 | 1.5 | 3 | 1.0 |
| Kleb.pneum. A 809 | >100 | 6 | 12.5 | 3 | 25 | 100 | 100 | 50 | — | >100 | >100 |
| Salm.dubl. P 43 | 12.5 | >100 | >100 | 3 | >100 | 100 | 100 | 3 | >100 | 12.5 | | while the reaction temperature was kept below −90° C. The resulting solution was then stirred for 60 minutes at −90° C. A solution of 7 mmol of trimethylsilyl 7-isocyanatocephalosporanate in 9 ml of toluene was added dropwise at −90° to −95° C. and the resulting reaction mixture was stirred for 45 minutes at temperatures slowly rising to −75° C. With simultaneous addition of 4 N HCl, the reaction mixture was poured into a mixture of 25 ml of iced water and 25 ml of diethyl ether and after the mixture had attained a constant pH 4.0, the pH was raised to 7.0 whereupon the layers were separated and the organic layer discarded. The water-layer was extracted with 25 ml of ethyl acetate at pH 6.0 and the extract was discarded. The desired cephalosporin (about 1:1 mixture of the D-form and the L-form) was obtained by means of repeated extraction of the water-layer with ethyl acetate at pH 4.5 to 4.0 to obtain 1.1 g (about 34%) of 7-[3-methyl-α-carbomethoxy-1,2,4-oxadiazol-5-yl-acetamido]-cephalosporanic acid, contaminated with less than 5 mol % of N,N'-dicephalosporanyl-urea.

IR (KBr-disc, values in cm$^{-1}$): ±3500 and ±2600, about 3150 to 3270, 2950, 1785, 1740, 1710 (sh), 1670, 1625, 1520–1560, 1440, 1425 (sh), 1390, 1360, 1300, 1240, (with shoulders), 1170, 1120, 1080, 1050, 805, 725.

PMR (about 3:1 mixture of d$_6$-DMSO and DCO$_2$D, 60 Mc, DSS, δ-values in ppm): 2.07 (s, 3H), 2.33 (s, 3H), about 3.6 (center of unresolved AB-q, 2H), 3.60 (s, 3H), from about 4.65 to 5.25 (AB-q, J≈13 cps) and 5.17 (center of doublet, J≈4.7 cps) together 3H, 5.78 (center of doublet, J≈4.5 cps, about 0.5H), 6.00 (center of doublet, J≈4.7 cps, about 0.5H). Because of exchange phenomena, C$_\alpha$-H and N-H are not seen in this spectrum. These signals appeared in the more complex spectra in d$_6$DMSO alone, respectively at 5.5 ppm (somewhat broad s, about 1H) and 9.55 ppm (doublets, about 0.8H).

By an analogous procedure 7-[3-methyl-α-(morpholino-carbonyl)-1,2,4-oxadiazol-5-yl-acetamido]-cephalosporanic acid were prepared in about 75% yield starting from 3-methyl-1,2,4-oxadiazol-5-yl-acetmorpholide, etc. (extraction of the desired cephalosporin at pH 4.0 to 2.5 with ethyl acetate).

IR (ibidem): ±3500 and ±2600, about 3230 to 3330, ±3050, ±2980, ±2940, ±2870, 1785, ±1735, ±1700, 1640–1660, 1585, 1530–1555, 1450, 1390, ±1240 (with shoulders), 1165, 1125, 1080, 1045, 720.

PMR (about 4:1 mixture of d$_6$-DMSO and DCO$_2$D, 60 Mc, DSS δ-values in ppm): 2.05 (s, 3H), 2.39 (s, 3H), about 3.6 (10H), from about 4.65 to 5.2 (AB-q, J≈13 cps) and 5.15 (d, J≈4.6 cps) together 3H, 5.60 (d,δν=0.7 cps, about 0.2H), 5.78 (center of 2 doublets, J≈4.6 cps and δν≈1.2 cps, 1H). The complex spectrum of the compound in d$_6$-DMSO alone showed a full C$_\alpha$-H singlet at 5.6 ppm and two superimposed NH doublets at 9.4 ppm (J'≈7.5 to 8.0 cps).

EXAMPLE 39

1,2,4-oxadiazole-3,5-diyl-bisacetic acid

Under anhydrous conditions, a solution of approximately 1 mole of n-butyl lithium in n-hexane was added dropwise to a solution of 50 g (0.51 mole) of 3,5-dimethyl-1,2,4-oxadiazole and 150 ml (1 mole) of TMEDA in 1400 ml of toluene. The period of time of the addition was expanded to 105 minutes to maintain the reaction temperature between −71° and −76° C. The reaction mixture was stirred for 90 minutes at −78° C. and was poured into a mixture of finely powdered carbon dioxide and a small volume of diethyl ether. After a few hours standing, the formed precipitate was collected by filtration through a glass filter under a blanket of dry air and the cake on the filter was washed with ethyl acetate and diethyl ether. The solid was suspended in a mixture of 250 ml of iced water and 10 ml of diethyl ether and concentrated phosphoric acid was added slowly and carefully to the stirred suspension till a clear brown solution was reached with a pH of 2.0. The solution was saturated with sodium chloride, cooled externally with ice and continuously extracted with dichloromethane. In the beginning of this extraction, the water-layer was heavier and the extraction was stopped after about 2 hours when the two layers became equally heavy. The organic extract containing much valeric acid, much 3-methyl-1,2,4-oxadiazol-5-yl-acetic acid, a relatively small amount of a rearranged product and also a considerable part of the desired bisacetic acid derivative, was evaporated in vacuo. The residue (58 g) which solidified in part was stirred three times with 50 ml volumes of n-hexane containing 2 vol % of diethyl ether to remove the present valeric acid which caused a slight loss of oxadiazole acetic acids. The solid residue (product 1) was temporarily stored in the refrigerator and the remaining water-layer was placed in crushed ice and continuously extracted with diethyl ether till practically all the 3-methyl-1,2,4-oxadiazol-5-yl-acetic acid had been removed from the water-layer. However, a slight amount of the rearranged product and a considerable amount of the bisacetic acid derivative also were present in the ethereal extract.

The remaining amount of the bisacetic acid derivative was completely removed from the cooled water-layer by continuous extraction with ethyl acetate at reduced pressure (ethyl acetate boiling at 35°–40° C.) and the obtained extract and the ethereal extract were combined and evaporated in vacuo. The residual solid material (product 2) was combined with product 1 and dissolved in about 250 ml of water. A few drops of concentrated phosphoric acid (till pH 2.0) and a slight amount of sodium chloride were added to this solution and the solution was cooled with an ice bath for 18 hours of continuous extraction with dichloromethane (heavier than the water-layer). This practically pure extract of 3-methyl-1,2,4-oxadiazol-5-yl-acetic acid was evaporated in vacuo and the slightly yellow, crystalline residue (product 4) weighed 27.5 g (about 37% of the used 3,5-dimethyl-1,2,4-oxadiazole). 24.0 g of completely pure material could be obtained by recrystallization of the residue.

The remaining water-layer, from which 3-methyl-1,2,4-oxadiazol-5-yl-acetic acid was completely removed, was submitted to continuous extraction with ethyl acetate as described above and the extract was treated with activated carbon and completely evaporated. The almost colorless crystalline residue weighed 23 g (product 5). In order to remove the rearranged by-product, this residue was stirred for several hours in a mixture of 60 ml of dichloromethane and 40 ml of ether. The undissolved, colorless crystalline mass was collected by filtration, washed with dichloromethane and n-hexane, and dried to constant weight to obtain 18.9 g (20%) of pure 1,2,4-oxadiazol-3,5-diyl-bisacetic acid with a m.p. of 109°–111° C. (partial decarboxylation sets in from about 100° C.).

IR (KBr-disc, values in cm$^{-1}$): very intensive absorptions at ±2900–3200, 1700–1720, 1430 and 1240. A number of other, less intensive absorptions at ±3400, 2500–2700, 1595, 1410 (sh), 1375, 1320, 1290, 1200, 1170, 945, 920, ±890, 850, 730 occurred.

PMR (about 1:1 mixture of $CDCl_3$ and $d_6$-DMSO, 60 Mc, TMS, δ-values in ppm): 3.75 (s, 2H), 4.02 (s, 2H), about 9 (broad s, about 2H).

Stability of 1,2,4-oxadiazol-3,5-diyl-bisacetic acid: A small sample was dissolved in slightly moist diethyl ether and the solution was refluxed for 24 hours. With thin-layer chromatography, it was found that less than 5% of destruction to 5-methyl-1,2,4-oxadiazol-3-yl-acetic acid had taken place.

The above described procedure is meant as an illustration only of problems as to reaction conditions and the isolation procedures in the preparation of 1,2,4-oxadiazol-3,5-diyl-bisacetic acids. It was found that the second lithiation which takes place in the position lateral to $C_3$ of the oxadiazole ring (when no additional, activating substituents such as phenyl are present) proceeds much more slowly in many cases than the often very fast and complete first lithiation lateral to $C_5$. In the example given above, the second lithiation did not progress further than at best 30–35% since no more than unimportant amounts of rearranged products were formed and loss of bisacetic acid was small, mainly or virtually exclusively occurring by the not optimalized purification of product 5 (see above), since its product of decarboxylation, 5-methyl-1,2,4-oxadiazol-3-yl-acetic acid, could not be isolated nor its presence indicated by thin-layer chromatography. The product balance indicated by the isolated crude reaction products (about 60%) suggests pronounced decarboxylation of the product of single lithiation under the circumstances applied in the isolation thus of 3-methyl-1,2,4-oxadiazol-5-yl-acetic acid which is considerably less stable than the bisacetic acid.

As shown by Example 4, the extent of dilithiation can be increased. If applied to the present example, this can be achieved by choosing from two alternatives. First, the addition of the second equivalent of n-butyl lithium as well as a short additional stirring period can be performed at somewhat higher temperatures of about $-60°$ to $-65°$ C. This procedure would, on the other hand, also result in a somewhat more pronounced formation of rearranged product(s), which in the present case would not impair a satisfactory isolation of the desired bisacetic acid. Second, the additional stirring period at low temperature can be extended considerably. In general, it depends on the additional substitution pattern of the starting 1,2,4-oxadiazol which yield increasing procedure is possible or more favorable. Relatively lower reaction temperatures of about $-75°$ to $-80°$ C. at the addition of the reagent and during the expanded additional stirring period are imperative in cases involving appreciable danger of more pronounced formation of rearranged products. This situation may prevail in cases wherein both lithiations proceed relatively slowly and thus in general when introduction of lithium lateral to $C_5$ is slowed down. This occurs when the $C_5$-substituent is not methyl but a longer alkyl chain such as ethyl.

Double lithiation often requires the use of a powerful agent and therefore, often but not always, the very powerful complex n-BuLi:TMEDA is the reagent of choice. Other agents which are of somewhat different nature and/or are less reactive sometimes produce better results such as when the lithiation lateral to $C_3$ is relatively more facile. Such a situation prevails when the $C_3$-substituent is benzyl and here the use of diisopropyl lithiumamide results in almost quantitative isolation of the almost pure dilithium salt of the corresponding bisacetic acid.

An expedient isolation procedure is an equally important asset for a successful preparation. Even if good conversions are realized, isolations in correspondingly fair yields are difficult to achieve since these bisacetic acids are relatively strong acids and are very soluble in water. Moreover, notwithstanding the fact that these compounds, relatively speaking, are usually appreciably more stable than could have been expected, they can still be termed to be sensitive compounds. Therefore, a suitable isolation procedure is somewhat at variance with regard to the substitution pattern and the composition of the reaction medium. As indicated by this Example and by Example 4, there are two ways to deal with the crude reaction mixture obtained after the reaction with carbon dioxide. The entire reaction mixture can be mixed with water, but this usually requires much water before solution is reached and also a number of manipulations afterwards which to a considerable extent can be omitted when it is possible to isolate first by filtration the double lithium salt of the bisacetic acid since then only a fraction of the volume of water is necessary to dissolve the double lithium salt. Depending on the individual case [the nature of the bisacetic acid and the relative extent of its formation, the nature of by-product(s) and the relative extent(s) of their formation as well as the nature of the reaction medium], it is often advantageous or necessary to submit solutions of the reaction product in water to a number of purifying operations before the actual extraction of the bisacetic acid is performed. Such operations can be in vacuo concentrations at pH values of about 8 or 5.5 or continuous extractions with n-pentane at pH 5.0 in order to remove by-products or constituents such as valeric acid, TMEDA and diisopropylamine.

By taking such factors into consideration, a number of bisacetic acids were prepared and isolated. Some data will be listed for two examples, which illustrate also the possibility of having an extra substituent in one of both possible sites:

A. α-(3)-phenyl-1,2,4-oxadiazol-3,5-diyl-bisacetic acid

Starting from 3-benzyl-5-methyl-1,2,4-oxadiazol and employing n-BuLi:TMEDA, the said compound was obtained in about 30% yield taking into account that the compound crystallized with approximately 0.5 mole of diethyl ether. The product in this state was a solid at room temperature.

PMR ($CDCl_3$ with a trace of $d_6$-DMSO, 60 Mc, TMS, δ-values in ppm): 3.9 (s, 2H), 5.3 (s, 1H), about 7.35 (center of a multiplet covering about 0.5 ppm, 5H), about 10.5 (slightly broad s, 2H).

Additional chemical proof of its structure was obtained by conversion to its dimethyl ester and to its bis-acet (4-fluoro) anilide.

B.
α-(5)-carbomethoxy-1,2,4-oxadiazol-3,5-diyl-bisacetic acid

Starting from methyl 3-methyl-1,2,4-oxadiazol-5-yl-acetate and employing n-BuLi:TMEDA, the nearly pure said compound was isolated in about 25% yield and the product was a slightly yellow, hygroscopic, crystalline solid.

IR (KBr-disc, values in $cm^{-1}$): ±3500, 2950–3130 (intensive), 1710–1745 (very intensive), 1600, 1450, 1245 (intensive), 1420, 1390, 1330, 1300, 1210, 1180, 860, 745.

-continued

| | | | | | | | | | | |
|---|---|---|---|---|---|---|---|---|---|---|
| Salm.typh. R 127 | 25 | >100 | >100 | 12.5 | >100 | >100 | >100 | — | 3 | — | 12.5 |
| Esch.coli U 20 | 50 | >100 | >100 | 12.5 | >100 | 100 | >100 | >100 | 6 | >100 | 50 |
| Shig.equir. T 3 | 1.5 | >100 | 25 | 6 | >100 | 12.5 | >100 | >100 | 3 | 25 | 3 |
| Pseud.aerug. H10 | >100 | >100 | >100 | >100 | >100 | >100 | >100 | >100 | >100 | >100 | >100 |
| 2396 | >100 | >100 | >100 | >100 | >100 | >100 | >100 | >100 | >100 | >100 | >100 |
| Wyeth A 1058 | >100 | >100 | >100 | >100 | >100 | >100 | >100 | >100 | >100 | >100 | >100 |
| Prot.rettg. A 821 | 6 | 3 | 50 | 1.5 | 3 | 3 | >100 | >100 | 3 | >100 | 50 |
| Prot.mirab. H 3 | >100 | >100 | >100 | 25 | >100 | 100 | >100 | >100 | 12.5 | >100 | 50 |
| L 93 | 12.5 | 25 | 25 | 12.5 | 100 | 12.5 | >100 | >100 | 1.5 | >100 | 3 |
| A 1200 | 100 | >100 | >100 | 25 | >100 | 100 | >100 | >100 | 6 | — | >100 |
| Prot.morg. 2241 | >100 | >100 | >100 | >100 | >100 | >100 | >100 | >100 | 50 | >100 | >100 |

| test compound | Example 11C | Example 11D | Example 11E | Example 11F | Example 11G | Example 11H | Example 11I | Example 11K | Example 11L | Example 11M |
|---|---|---|---|---|---|---|---|---|---|---|
| Bac.Subt.ATCC 6633 | 0.12 | 0.5 | 1 | 6 | 0.03 | 0.06 | 0.12 | 0.25 | 0.12 | 0.06 |
| Staph.aureus A 321 | 0.12 | 1 | 0.5 | 6 | 0.12 | 0.25 | 1 | 1.5 | 0.25 | 0.12 |
| A 335[1] | 0.5(0.69) | 6(6) | 0.75(0.25) | 50(15) | 3(30) | 12.5 | 3(1.2) | 1.5(0.9) | 1 | 12.5 |
| A2000 | 0.5(0.18) | 3(1.2) | 0.75(3.7) | 50(15) | 1.5(23) | 6 | 1.5(1.2) | 1.5(1.2) | 1 | 6 |
| A2001 | 0.5(0.25) | 3(0.6) | 1(0.25) | 12.5(8) | 1 (3.7) | 3 | 1.5(1.2) | 1 (0.9) | 1 | 6 |
| Strep.haem. A 266 | 0.03 | 0.5 | 0.25 | 6 | (0.5) | 0.5 | 0.25 | 0.06 | 0.25 | 0.5 |
| Strep.faec. L 80 | 1.5 | 100 | 12.5 | >100 | 3 | 6 | 75 | 100 | 50 | 6 |
| Dipl.pneum. L 54 | 0.06 | 1.5 | — | 50 | 0.25 | 0.25 | — | 1 | 1 | 0.5 |
| Haem.infl. A 1030 | (23) | (90) | (125) | (125) | (125) | (3.7) | (>125) | (125) | (≧125) | (3.7) |
| Bruc.melit. A 488 | 6 | 10 | 50 | 6 | 1.5 | 0.25 | 6 | 12.5 | 6 | 0.5 |
| Past.multo. A 723 | 6 | 6 | 25 | 100 | 1 | 1.5 | 1.5 | 1.5 | 2 | 1 |
| Kleb.pneum. A 809 | 12.5 | 6 | 100 | 100 | >100 | >100 | 6 | 6 | 1.5 | >100 |
| Salm.dubl. P 43 | >100 | 12.5 | >100 | 100 | 12.5 | 50 | 12.5 | 100 | 3 | 50 |
| Salm.typh. R 127 | >100 | 12.5 | >100 | >100 | 25 | 100 | 25 | >100 | 6 | >100 |
| Esch.coli U 20 | >100 | 12.5 | >100 | >100 | 100 | ≧100 | 50 | >100 | 6 | >100 |
| Shig. equir. T 3 | 25 | 1.5 | >100 | 12.5 | 10 | 25 | 12.5 | 25 | 3 | 50 |
| Pseud.aerug. H 10 | >100 | >100 | >100 | >100 | >100 | >100 | >100 | >100 | >100 | >100 |
| 2396 | >100 | >100 | >100 | >100 | >100 | >100 | >100 | >100 | >100 | >100 |
| Wyeth A1058 | >100 | >100 | >100 | >100 | >100 | >100 | >100 | >100 | >100 | >100 |
| Prot.rettg. A 821 | 3 | 40 | >100 | >100 | 3 | 12.5 | 6 | 12.5 | 1 | 3 |
| Prot.mirab. H 3 | >100 | 6 | >100 | >100 | >100 | >100 | 12.5 | >100 | 50 | >100 |
| L 93 | 100 | 6 | >100 | >100 | 12.5 | 6 | 12.5 | 12.5 | 3 | 25 |
| A 1200 | >100 | 12.5 | >100 | >100 | 100 | >100 | 25 | >100 | 25 | >100 |
| Prot.morg. 2241 | >100 | >100 | >100 | >100 | >100 | >100 | >100 | >100 | >100 | >100 |

| test compound→ | Example 13 | Example 18 | Example 19 | Example 31 | Example 37 | Example 38 |
|---|---|---|---|---|---|---|
| Bac.subt. ATCC 6633 | 0.03 | 1 | 0.5 | 1 | 0.12 | 6 |
| Staph.aureus A 321 | 0.12 | 1 | 6 | 1.5 | 0.5 | 25 |
| A 355[1] | 10 | 1.5(1.2) | 12.5(15) | 6(1.9) | 1.5(0.9) | 25 (23) |
| A2000 | 1.5 | 1.5(1.2) | 6 (5) | 3(1.2) | 1.5(0.6) | 25 (23) |
| A2001 | 1.5 | 1 (0.9) | 6 (6) | 3(1.2) | 0.75(0.45) | 25 (15) |
| Strep.haem. A 266 | 0.03 | 0.25 | 0.5 | (2.5) | 0.12 | — |
| Strep. faec. L 80 | 6 | >100 | >100 | 25 | 50 | >100 |
| Dipl.pneum. L 54 | 1.0 | 3 | 3 | 1.5 | 0.75 | 12.5 |
| Haem.infl. A 1030 | (125) | (6) | (23) | (≧125) | (125,23) | (125) |
| Bruc.melit. A 488 | 3 | 6 | 6 | — | — | — |
| Past. multo. A 723 | 1 | 10 | 25 | 1.5 | 1 | 12.5 |
| Kleb.pneum. A 809 | >100 | 6 | 50 | 6 | 3 | 50 |
| Salm.dubl. P 43 | 3 | 6 | 25 | 6 | 3 | 100 |
| Salm.typh. R 127 | 25 | 12.5 | 100 | 12.5 | 12.5 | 100 |
| Esch.coli U 20 | 50 | 12.5 | 100 | 12.5 | 12.5 | >100 |
| Shig. equir. T 3 | 3 | 3 | 6 | 12.5 | 3, 6 | 50 |
| Pseud.aerug. H 10 | >100 | >100 | >100 | >100 | >100 | >100 |
| 2396 | — | >100 | >100 | >100 | >100 | >100 |
| Wyeth A 1058 | >100 | >100 | >100 | >100 | >100 | >100 |
| Prot. rettg. A 821 | 6 | 12.5 | 6 | 12.5 | 3, 12.5 | 25 |
| Prot. mirab. H 3 | 100 | 25 | 50 | 25 | 25 | 100 |
| L 93 | 3 | 6 | 25 | 6 | 6, 12.5 | 50 |
| A 1200 | 25 | 25 | >100 | 25 | 50, 100 | >100 |
| Prot. morg. 2241 | 100 | >100 | >100 | >100 | >100 | >100 |

| Test compound | F | G | 41 B | 41 A |
|---|---|---|---|---|
| Bac. Subt. ATCC 6633 | 1.5 | 0.25 | 0.5 | 0.25 |
| Staph. aureus A 321 | 3 | 0.25 | 0.25 | 0.25 |
| A 355 | 6(6) | 1(0.9) | 1(0.9) | 0.75(0.3) |
| A 2000 | 6(4) | 0.75(0.6) | 1(0.6) | 0.5(0.23) |
| A 2001 | 6(3.7) | 0.5(0.6) | 0.5(0.6) | 0.5(0.15) |
| Strep.haem A 1088 | 3 | 0.25 | 0.5 | 0.06 |
| Strep.faec. L 80 | >100 | 50 | >100 | 50 |
| Dipl.pneum. L 54 | 1 | 0.5 | 1.5 | 0.75 |
| Sarc. lutea ATCC 9341 | (3.7) | 0.5 | 0.5 | — |
| Haem.Suis A 2096 | (0.23) | (0.23) | — | (15) |
| Bruc. Suis A 2126 | 1 | 1 | 1 | 6 |
| Past.multo. A 723 | 1 | 1 | 1.5 | 1.5 |
| Kleb.pneum. A 809 | 0.5 | 0.5 | 1 | 6 |
| Salm.dublin P 43 | 0.5 | 1.5 | 1.5 | 12.5 |
| Salm.typh. R 172 | 0.75 | 1.5 | 1.5 | 50 |

| | | | | |
|---|---|---|---|---|
| Esch.coli U 20 | 0.75 | 0.75 | 1.5 | 3 |
| Actinob.equ. T 3 | 0.5 | 0.5 | 0.5 | 12.5 |
| Pseud.aerug. H 10 | | | | |
| Salm.dublin P 43 | 0.5 | 1.5 | 1.5 | 12.5 |
| Salm.typh. R 172 | 0.75 | 1.5 | 1.5 | 50 |
| Esch.coli U 20 | 0.75 | 0.75 | 1.5 | 3 |
| Actinob.equ. T 3 | 0.5 | 0.5 | 0.5 | 12.5 |
| Pseud.aerug. H 10 | 100 | 100 | 100 | 100 |
| 2396 | 100 | 100 | 100 | 100 |
| Wyeth a 1058 | 100 | 100 | 100 | 100 |
| Prot.rettg. A 821 | 0.25 | 0.25 | 0.5 | 1.5 |
| Prot.mirab. H 3 | 1.5 | 25 | 12.5 | 100 |
| L 93 | 1.5 | 3 | 12.5 | 6 |
| A 1200 | 3(1.2) | 25(15) | 25(5) | 100 |
| Prot.morg. 2241 | 25 | 100 | 100 | 100 |

[1]Penicillinase-producing strain

Initial in vivo experiments with some of the penicillanic acid and cephalosporanic acid derivatives gave the following results:

(a) For sodium 7-[(3-methyl-1,2,4-oxadiazol-5-yl)-acetamido]-cephalosporanate (as prepared in Example 10), the acute toxicity was determined in mice (Swiss) with one intraperitoneal administration. The $LD_{50}$ appeared to be $>6000$ mg/kg (Cephalotin-$LD_{50}>6000$ mg/kg).

In a protection test $ED_{50}$ values for this compound were found as listed in the Table below:

and a strong urine activity against pathogenic germs. The compound may preferably be used parenterally.

(c) The $ED_{50}$ values of sodium 7-[(3-methyl-1,2,4-oxadiazol-5-yl)-acetamido]-3-[1-methyl-tetrazol-5-yl-mercaptomethyl]-3-cephem-4-carboxylate (indicated as compound G) and of disodium 7-[(3-carboxymethyl-1,2,4-oxadiazol-5-yl)acetamido]-3-[1-methyl-tetrazol-5-yl-mercaptomethyl]-3-cephem-4-carboxylate (indicated as Compound F) and the potency ratios with reference to cefalotin as reference compound were determined in a protection test, as listed below:

| Protectiontest by i.p. infection | adminis- tration | Compound G | | Compound F | |
|---|---|---|---|---|---|
| | | $ED_{50}$ mg/kg | Potency ratio | $ED_{50}$ mg/kg | Potenoy ratio |
| Klebsiella pneumoniae A 265 | i.p. | 86,0 | 1,09 Cefalotin | 16,0 | 5,7 Cefalotin |
| Proteus mirabilis A 1200 | s.c. | 8,7 | 1,4 Cefalotin | 2,2 | 6,9 Cefalotin |
| | | | | 1,35 | 6,5 Cefazolin |
| Proteus rettgeri A 821 | s.c. | | | 0,023 | >5 Cefalotin |

| | | $ED_{50}$ (mg/kg) | | | |
|---|---|---|---|---|---|
| Compound | Ad- minis- tration | Staph. aureus pen.resis- tant | Proteus rett- geri | Kleb- siella pneum- onlae | Escheri- chia coli |
| Compound of Example 10 | s.c. | 31.0 | 1.25 | — | — |
| | i.p. | — | — | 2.3 | 120.0 |
| Cephalotin | s.c. | 37.6 | 4.34 | — | — |
| | i.p. | — | — | 0.8 | >300 |

Blood levels of the above mentioned test compound and of cephalotin were determined after an intramuscular administration of 50 mg/kg of these compounds in an aqueous solution in rabbits. After half an hour for the compound of Example 10, a value of 38.3 μg/ml was found and for cephalotin 33.9 μg/ml. In urine, 35.9% of the administered compound of Example 10 was retrieved, while in the case of cephalotin 22.2% was retrieved within six hours.

(b) The $ED_{50}$-value of sodium 7-[(3-methoxymethyl-1,2,4-oxadiazol-5-yl)-acetamido]-cephalosporanate of Example 37 was found to be 1.2 mg/kg in a protection test against a penicillin resistant Staphylococcus aureus strain after subcutanal administration, while for cephalotin a value of 1.3 mg/kg was found. The compound of Example 37 gave in tests with mice good blood levels (d) the blood and urine contents of the above-indicated compound G and of monosodium 7-[(3-carboxymethyl-1,2,4-oxadiazol-5-yl)acetamido]-3-acetoxymethyl-3-cephem-4-carboxylate (as prepared in example 35) were determined after intramuscular administration of these compounds in an aqueous solution in rabbits, as listed below:

test animals: rabbits "Nieuw Zeelander" ♀♀
weight: 2.3–2.9 kg.
The rabbits did not receive any food during 20 hours and were afforded water ad libitum. Each testgroup consisted of 3 rabbits.
Dose: 50 mg/kg
Vehiculum: Physiol. saline solution
Bloodsamples were taken after ¼—½—1—2—4 hours
Urinesamples were taken after 1—3—6—24—27 hours (in practice only the secreted amounts after 6 and 24 hours were used).
Testorganisms: Bacillus subtilis ATCC 6633 and Bacillus callidolactis E 16.
The contents of the compounds in the samples were determined microbiologically.
(Only microbiologically detected concentrations, i.e. anti-bacterially active concentrations only have been indicated and determined in relation to the original administered compound).

| | | | | STATISTICAL ANALYSIS | |
|---|---|---|---|---|---|
| | | Ex. 35 | Compound G | significant + | t value |
| Serumlevel in mcg/ml | ¼ hr | 119,3 | 156,7 | — | 1,68 |
| | ½ hr | 93,7 | 136,7 | — | 1,58 |

| | Ex. 35 | Compound G | STATISTICAL ANALYSIS significant + | t value |
|---|---|---|---|---|
| after 1 hr | 56 | 49 | — | 0,41 |
| 2 hr | 15,4 | 25 | — | 1,57 |
| 4 hr | 1,8 | 6,7 | + | 6,04 |
| Secretion of compound in urine in 6 hr | 35,9 | 51,3 | — | 1,13 |
| % of the administered dose after 24 hr | 51,4 | 55,5 | — | 0,34 |

COMPOSITION EXAMPLE A

From the penicillins and cephalosporins of the invention, syrups were prepared by mixing the following ingredients:

| active compound | 1.5–6 | g |
|---|---|---|
| sodium carboxymethylcellulose | 0.06–0.600 | g |
| sodium saccharinate | 0.1–1 | g |
| methyl p-hydroxybenzoate | 0.06 | g |
| strawberry flavor | 0.1–5 | g |
| amaranth | 0.010 | g |
| saccharose | 30 | g |
| water added to a volume of | 60 | ml |

These prepared syrups may be used for oral administration.

COMPOSITION EXAMPLE B

Capsules containing as active ingredient a penicillin or cephalosporin of the invention were prepared in the usual way. The components of these capsules are listed below:

| active compound | 150–500 mg |
|---|---|
| potassium bicarbonate | 100–300 mg |
| magnesium stearate | 2–10 mg |
| lactose | q.s. for 1 capsule. |

These capsules may be used for oral administration.

COMPOSITION EXAMPLE C

Tablets containing as active ingredient a penicillin or cephalosporin of the invention were prepared in the usual way. The components of the tablets are listed below:

| active compound | 125–500 mg |
|---|---|
| polyvinylpyrrolidone | 5–30 mg |
| amylum maidis | 100–300 mg |
| magnesium stearate | 1–20 mg |
| lactose | q.s. for 1 tablet |

These tablets may be used for oral administration.

COMPOSITION EXAMPLE D

From the penicillins and cephalosporins of the invention, a dry powder for injection was prepared in the usual way. A quantity of 100 to 2000 mg of the sterile sodium salt of the said compound was aseptically introduced into a vial suitable for injectable compositions under a nitrogen atmosphere. The vials were closed with rubber plates, which were fixed in their position by aluminium joint rings to eliminate the exchange of gases or the penetration of microorganisms. Before use, the powder was dissolved in a suitable amount of sterile and pyrogen-free water.

Various modifications of the compositions and methods of the invention may be made without departing from the spirit or scope thereof and it is to be understood that the invention is to be limited only as defined in the appended claims.

We claim:

1. A cephalosporanic acid derivative of the formula

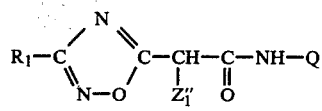

wherein Q is selected from the group consisting of

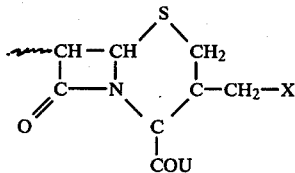

wherein U is a group OE', wherein E' is selected from the group consisting of hydrogen, a non-toxic, pharmaceutically acceptable salt forming cation and a non-toxic, pharmaceutically acceptable lower alkyl optionally substituted with lower alkanoyloxy, X is selected from the group consisting of acetoxy and S—Q', wherein Q' is selected from the group consisting of a tetrazolyl, triazolyl, imidazolyl or thiadiazolyl optionally substituted with alkyl of 1 to 6 carbon atoms, $R_1$ is carboxyl methyl optionally transformed into a non-toxic, pharmaceutically acceptable ester or salt and $Z_1''$ is selected from the group consisting of hydrogen and alkyl of 1 to 6 carbon atoms and

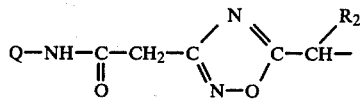

wherein Q is as defined above and $R_2$ is selected from the group consisting of hydrogen and alkyl of 1 to 6 carbon atoms.

2. A compound of claim 1 selected from the group consisting of 7-[3-carboxymethyl-1,2,4-oxadiazol-5-yl-acetamido]-3-[1-methyl-tetrazol-5-yl-mercaptomethyl]-3-cephem-4-carboxylic acid and its non-toxic, pharmaceutically acceptable salts and esters.

3. A method of killing bacteria comprising contacting bacteria with a bactericidal amount of at least one compound of claim 1.

4. An antibacterial composition comprising a bactericidially effective amount of at least one compound of claim 1 and a pharmaceutical carrier.

5. A method of combatting bacterial infections in warm-blooded animals comprising administering to warm-blooded animals a bactericidally effective amount of at least one compound of claim 1.

6. The method of claim 5 selected from the group consisting of 7-[3-carboxymethyl-1,2,4-oxadiazol-5-yl-acetamido]-3-[1-methyl-tetrazol-5-yl-mercaptomethyl]-3-cephem-4-carboxylic acid and its non-toxic, pharmaceutically acceptable salts and esters.

* * * * *

UNITED STATES PATENT AND TRADEMARK OFFICE
CERTIFICATE OF CORRECTION

PATENT NO. : 4,160,829                 Page 1 of 2
DATED : July 10, 1979
INVENTOR(S) : ROBERT HEIJBOER, ANTOON van HARREWIJN and PETER W. HENNIGER It is certified that error appears in the above-identified patent and that said Letters Patent are hereby corrected as shown below:

| Col. | Line | | |
|---|---|---|---|
| 2 | 14 | "$\geqslant$1" should be | --$\geqslant$1-- |
| 2 | 44 | "5-yla" should be | --5-yl-acetic-- |
| 8 | 24 | "triezolyl" should be | --triazolyl-- |
| 17 | 60 | "(S,2H)" should be | --(s, 2H)-- |
| 26 | 47 | "$\pm$2600" should be | --$+$ 2600-- |
| 26 | 58 | "(d, J$\sim$8.5 cps.. 0.9H)" should be --(d, J$\approx$ 8.5 cps. 0.9H)-- | |
| 40 | 1 | "2H9" should be | --2H)-- |
| 49 | 38 | "were" should be | --was-- |
| 57 | Col. 7 | "$\geqslant$100" should be | -- $\geqslant$100-- |
| 57 | Col. 5 | "($\geqslant$125)" should be | --($\geqslant$125)-- |
| 58 | Col. 10 | " $\geqslant$125" should be | -- $\geqslant$125-- |

UNITED STATES PATENT AND TRADEMARK OFFICE
CERTIFICATE OF CORRECTION

PATENT NO. : 4,160,829

DATED : July 10, 1979

INVENTOR(S) : ROBERT HEIJBOER, ANTOON van HARREWIJN and PETER W. HENNIGER

It is certified that error appears in the above-identified patent and that said Letters Patent are hereby corrected as shown below:

| Col. | Line | |
|---|---|---|
| 2 | 14 | "$\geqslant 1$" should be --$\geqslant 1$-- |
| 2 | 44 | "5-yla" should be --5-yl-acetic-- |
| 8 | 24 | "triezolyl" should be --triazolyl-- |
| 17 | 60 | "(S,2H)" should be --(s, 2H)-- |
| 26 | 47 | "$\pm 2600$" should be --$\pm$ 2600-- |
| 26 | 58 | "(d, J$\sim$8.5 cps.. 0.9H)" should be --(d, J$\approx$ 8.5 cps. 0.9H)-- |
| 40 | 1 | "2H9" should be --2H)-- |
| 49 | 38 | "were" should be --was-- |
| 57 | Col. 7 | "$\geqslant 100$" should be -- $\geqslant 100$-- |
| 57 | Col. 5 | "($\geqslant 125$)" should be --($\geqslant 125$)-- |
| 58 | Col. 10 | " $\geqslant 125$" should be -- $\geqslant 125$-- |

UNITED STATES PATENT AND TRADEMARK OFFICE
CERTIFICATE OF CORRECTION

PATENT NO. : 4,160,829  
DATED : July 10, 1979  
INVENTOR(S) : ROBERT HEIJBOER, ANTOON van HARREWIJN and PETER W. HENNIGER Page 2 of 2

It is certified that error appears in the above-identified patent and that said Letters Patent are hereby corrected as shown below:

| Col. | Line<br>Cols | |
|---|---|---|
| 59 | 1 to 5 | Delete the first 6 lines to Salm.typh. R 172 |
| Claim<br>62 | 55 | 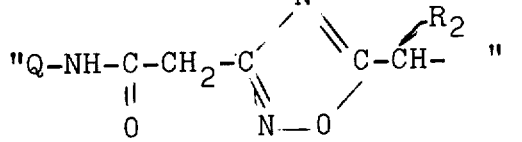 should be |

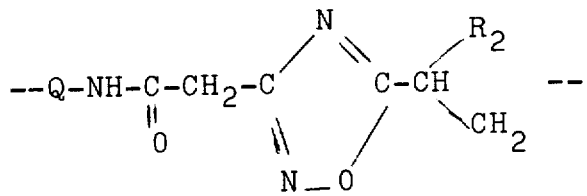

Signed and Sealed this

Twenty-second Day of April 1980

[SEAL]

Attest:

SIDNEY A. DIAMOND

Attesting Officer

Commissioner of Patents and Trademarks